US012673096B2

(12) United States Patent  
Miller et al.

(10) Patent No.: US 12,673,096 B2  
(45) Date of Patent: Jul. 7, 2026

(54) VACCINES AGAINST VIRAL PATHOGENS

(71) Applicant: Hexamer Therapeutics, Inc., Pullman, WA (US)

(72) Inventors: Keith Douglas Miller, Moscow, ID (US); Robert Bogden, Viola, ID (US)

(73) Assignee: Hexamer Therapeutics, Inc., Pullman, WA (US)

( * ) Notice: Subject to any disclaimer, the term of this patent is extended or adjusted under 35 U.S.C. 154(b) by 701 days.

(21) Appl. No.: 17/997,886

(22) PCT Filed: May 4, 2021

(86) PCT No.: PCT/US2021/030579  
§ 371 (c)(1),  
(2) Date: Nov. 3, 2022

(87) PCT Pub. No.: WO2021/226026  
PCT Pub. Date: Nov. 11, 2021

(65) Prior Publication Data  
US 2023/0346920 A1 Nov. 2, 2023

Related U.S. Application Data

(60) Provisional application No. 63/019,654, filed on May 4, 2020.

(51) Int. Cl.

| | |
|---|---|
| *A61K 39/215* | (2006.01) |
| *A61K 39/385* | (2006.01) |
| *A61P 31/14* | (2006.01) |
| *C07K 14/005* | (2006.01) |
| *C07K 14/165* | (2006.01) |
| *A61K 39/00* | (2006.01) |

(52) U.S. Cl.  
CPC .......... *A61K 39/215* (2013.01); *A61K 39/385* (2013.01); *A61P 31/14* (2018.01); *C07K 14/005* (2013.01); *A61K 2039/55572* (2013.01); *A61K 2039/6012* (2013.01); *C07K 2319/40* (2013.01); *C12N 2770/20022* (2013.01); *C12N 2770/20034* (2013.01); *C12N 2770/20071* (2013.01)

(58) Field of Classification Search  
None  
See application file for complete search history.

(56) References Cited

U.S. PATENT DOCUMENTS

| | | | |
|---|---|---|---|
| 5,972,659 A | 10/1999 | Haynes et al. | |
| 2021/0275665 A1* | 9/2021 | Cho ..................... | C07K 14/165 |

FOREIGN PATENT DOCUMENTS

| | | |
|---|---|---|
| CN | 114599387 A | 6/2022 |
| WO | WO2015164798 A1 | 10/2015 |

| | | |
|---|---|---|
| WO | WO2018027252 A1 | 2/2018 |
| WO | WO2020014609 A2 | 1/2020 |
| WO | WO2021050722 A1 | 3/2021 |

OTHER PUBLICATIONS

Zeigler et al. Epitope targeting with self-assembled peptide vaccines. npj Vaccines (2019) 4:30.*  
Grifoni et al., A Sequence Homology and Bioinformatic Approach Can Predict Candidate Targets for Immune Responses to SARS-CoV-2, Cell Host & Microbe 27, 671-680. Apr. 8, 2020.*  
Miller et al. Novel Anti-Nicotine Vaccine Using a Trimeric Coiled-Coil Hapten Carrier. PLoS One. Dec. 10, 2014; 9(12):e114366.*  
Invitation to Pay Fees dtd Aug. 19, 2021 for PCT Application No. PCT/US2021/030579, mailed Aug. 19, 2021, 3 pages.  
International Search Report and Written Opinion for PCT Application No. PCT/US2021/030579, mailed Oct. 29, 2021, 12 pages.  
Canadian Office Action mailed Jan. 8, 2024 for Canadian Application No. 3,173,307, a foreign counterpart to U.S. Appl. No. 17/997,886, 3 pages.  
Search Report and Written Opinion for European Application No. 21800217.8, Dated Jun. 18, 2024, 11 pages.  
Grifoni, et. al, "A Sequence Homology and Bioinformatic Approach Can Predict Candidate Targets for Immune Responses to SARS-CoV-2," Cell Host & Microbe, vol. 27, Apr. 2020, pp. 671-680.  
Robson, "COVID-19 Coronavirus Spike Protein Analysis for Synthetic Vaccines, a Peptidomimetic Antagonist, and Therapeutic Drugs, and Analysis of a Proposed Achilles' Heel Conserved Region to Minimize Probability of Escape Mutations and Drug Resistance," Computers in Biology and Medicine, vol. 121, 103749, Jun. 2020, 79 pages.  
Office Action for Chinese Application No. 202180044483.3, Dated Nov. 29, 2024, 20 pages.  
Ahmed, et al., "Preliminary Identification of Potential Vaccine Targets for the COVID-19 Coronavirus (SARS-CoV-2) Based on SARS-CoV Immunological Studies," Viruses, vol. 12, No. 254, Feb. 2020, pp. 1-15.

(Continued)

*Primary Examiner* — Nianxiang Zou  
(74) *Attorney, Agent, or Firm* — Lee & Hayes, P.C.

(57) ABSTRACT

The present disclosure describes a unique viral peptide (VP) vaccine for preventing or treating viral diseases. The vaccine is produced synthetically and includes no production steps in biological cells (e.g. *E. coli*, CHO cells, yeast cells) that would require subsequent endotoxin assays/removal or viral clearance procedures. The hC peptide is synthesized separately from the VP, and following self-assembly of the hC, the VP is covalently coupled to form the VP-hC conjugate which can serve as a vaccine for preventing or treating viral diseases. The hC includes heptad repeats following a specific pattern. Optionally, the VP-hC conjugate further includes one or more T-cell epitopes at the N- and/or C-terminus of the one or more amphipathic alpha-helices. The present disclosure also describes compositions comprising immunogenic compositions including VP-hC conjugate.

29 Claims, 16 Drawing Sheets  
Specification includes a Sequence Listing.

(56)　　　　　　　References Cited

OTHER PUBLICATIONS

Bhattacharya, et al., "Development of Epitope-Based Peptide Vaccine Against Novel Coronavirus 2019 (SARS-COV-2): Immunoinformatics Approach," Journal of Medical Virology, vol. 92, 2020, pp. 618-631.

Office Action for Canadian Application No. 3,173,307, Dated Apr. 23, 2025, 5 pages.

Office Action for Japanese Application No. 2022-567385, Dated May 20, 2025, 23 pages.

Walls, et al., "Structure, Function, and Antigenicity of the SARS-CoV-2 Spike Glycoprotein," Cell, vol. 180, Apr. 2020, pp. 281-292.

Zheng, et al., "Novel Antibody Epitopes Dominate the Antigenicity of Spike Glycoprotein in SARS-CoV-2 Compared to SARS-CoV," Cellular & Molecular Immunology, vol. 17, Mar. 2020, pp. 536-538.

Examination Report for Australian Application No. 2021268621, Dated Dec. 4, 2025, 3 pages.

Office Action for Japanese Application No. 2022-567385, Dated Jan. 13, 2026, 14 pages.

* cited by examiner

Many of the Vaccine Constructs+Adjuvant Induce Predominantly
IgG1 Isotype 28 Days Post-Prime Some of the Vaccine Constructs+Adjuvant Induce Isotype Switching 42 Days Post-Prime (14 Days Post Boost)

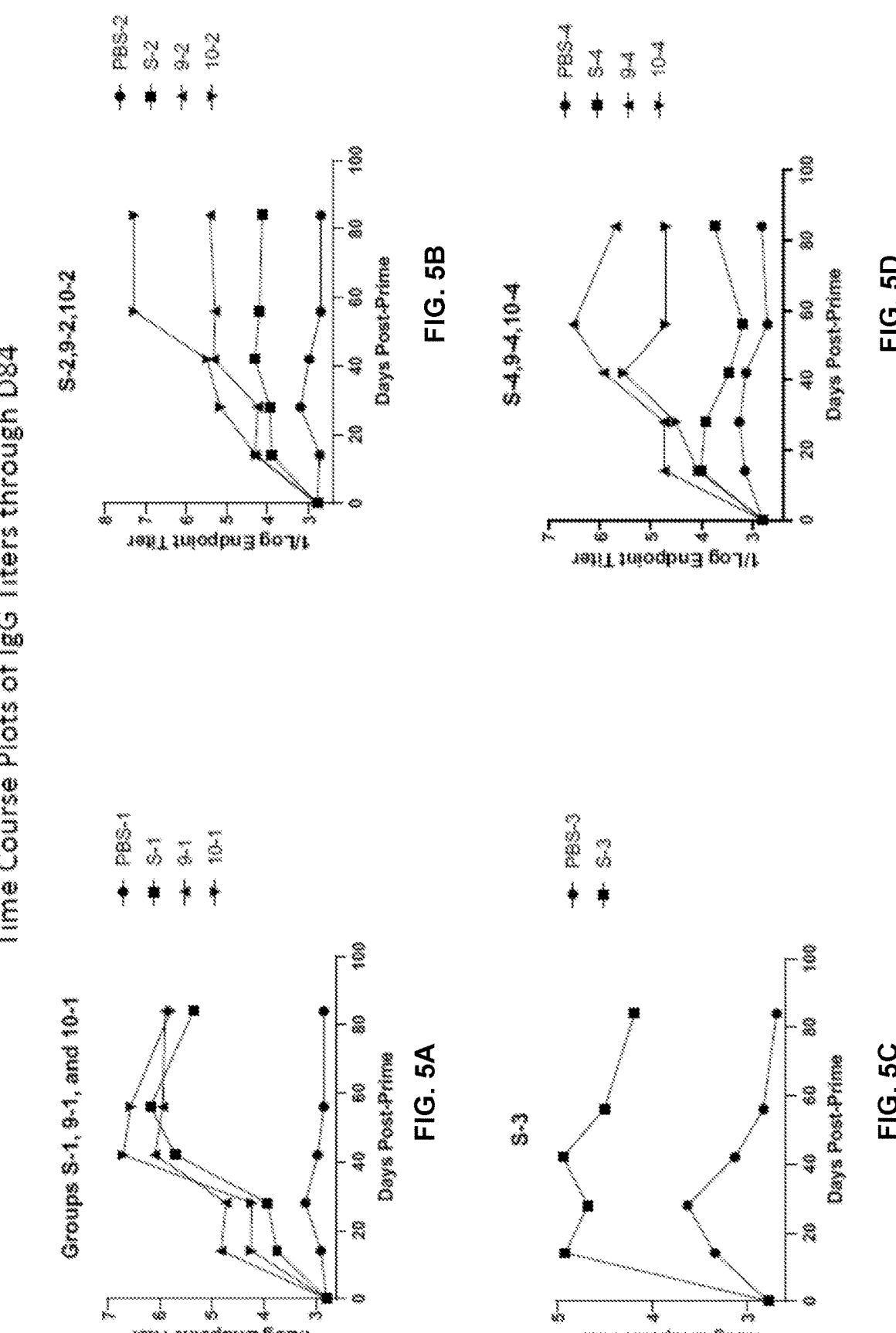
Time Course Plots of IgG Titers through D84

D56 sera antibody binding to commercially obtained S-Protein

Binding of d56 IgGs to the Spike Holoprotein
(S1+S2, active trimer, prefusion conformation)

SEQUENCE LISTING

<160> NUMBER OF SEQ ID NOS: 140

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a hydrophobic or non-polar residue
<220> FEATURE:
<221> NAME/KEY: MISC_FEATURE
<222> LOCATION: (2)..(2)
<223> OTHER INFORMATION: Xaa is a positively charged, negatively
      charged, polar uncharged, or non-polar aliphatic residue
<220> FEATURE:
<221> NAME/KEY: MISC_FEATURE
<222> LOCATION: (3)..(3)
<223> OTHER INFORMATION: Xaa is a negatively charged, positively
      charged, non-polar aliphatic, polar uncharged residue or any
      natural or non-natural residue for epitope coupling to a hapten or
      any other molecule
<220> FEATURE:
<221> NAME/KEY: MISC_FEATURE
<222> LOCATION: (4)..(4)
<223> OTHER INFORMATION: Xaa is a hydrophobic or non-polar residue
<220> FEATURE:
<221> NAME/KEY: MISC_FEATURE
<222> LOCATION: (5)..(5)
<223> OTHER INFORMATION: Xaa is a negatively charged, positively
      charged, non-polar aliphatic, polar uncharged residue, or any
      natural or non-natural residue for epitope coupling to a hapten or
      any other molecule
<220> FEATURE:
<221> NAME/KEY: MISC_FEATURE
<222> LOCATION: (6)..(6)
<223> OTHER INFORMATION: Xaa is any natural or non-natural residue for
      epitope coupling to a hapten or any other molecule
<220> FEATURE:
<221> NAME/KEY: MISC_FEATURE
<222> LOCATION: (7)..(7)
<223> OTHER INFORMATION: Xaa is a negatively charged, positively
      charged, polar uncharged, non-polar aliphatic residue, or any
      natural or non-natural residue for epitope coupling to a hapten or
      any other molecule

<400> SEQUENCE: 1

Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: The sequence as a whole repeats n times,
      wherein n is an integer greater than 1
<220> FEATURE:
<221> NAME/KEY: MISC_FEATURE
<222> LOCATION: (1)..(1)
<223> OTHER INFORMATION: Xaa is a hydrophobic or non-polar residue
<220> FEATURE:
<221> NAME/KEY: MISC_FEATURE
<222> LOCATION: (2)..(2)
<223> OTHER INFORMATION: Xaa is a positively charged, negatively
      charged, polar uncharged, or non-polar aliphatic residue
<220> FEATURE:
<221> NAME/KEY: MISC_FEATURE
<222> LOCATION: (3)..(3)
<223> OTHER INFORMATION: Xaa is a negatively charged, positively

```
        charged, non-polar aliphatic, or polar uncharged residue
<220> FEATURE:
<221> NAME/KEY: MISC_FEATURE
<222> LOCATION: (4)..(4)
<223> OTHER INFORMATION: Xaa is a hydrophobic or non-polar residue
<220> FEATURE:
<221> NAME/KEY: MISC_FEATURE
<222> LOCATION: (5)..(5)
<223> OTHER INFORMATION: Xaa is a negatively charged, positively
        charged, non-polar aliphatic, or polar uncharged residue
<220> FEATURE:
<221> NAME/KEY: MISC_FEATURE
<222> LOCATION: (6)..(6)
<223> OTHER INFORMATION: Xaa is any natural or non-natural residue for
        epitope coupling
<220> FEATURE:
<221> NAME/KEY: MISC_FEATURE
<222> LOCATION: (7)..(7)
<223> OTHER INFORMATION: Xaa is a negatively charged, positively
        charged, polar uncharged, or non-polar aliphatic residue
<220> FEATURE:
<221> NAME/KEY: MISC_FEATURE
<222> LOCATION: (7)..(7)
<223> OTHER INFORMATION: Xaa is Ala, Asp, His, Ser, Glu, Arg, Asn, Gln,
        Lys, or Gly

<400> SEQUENCE: 2

Xaa Xaa Xaa Xaa Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Leu Arg Ser Ile Gly Lys Asp
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Leu Arg Ser Ile Gly Arg Asp
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Ile Arg Glu Ile Ser Arg Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6
```

```
Ile Arg Glu Val Ala Gln Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ile Arg Asp Ile Ala Lys Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Ile Arg Asp Ile Gly Arg Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Ile Arg Asp Val Gly Gln Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Ile Arg Asp Leu Ala Lys Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Val Lys Asp Val Ala Arg Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12
```

```
Ile Arg Asp Ile Gly Asn Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Ile Lys Asp Leu Ala Arg Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Ile Lys Lys Leu Lys Lys Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Ile Arg Ser Ile Gly Lys Glu
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Ile Arg Ser Ile Gly Arg Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Ile Lys Ser Ile Gly Arg Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Ile Arg Ser Ile Gly Arg Gly
```

-continued

```
1               5

<210> SEQ ID NO 19
<211> LENGTH: 28
<212> TYPE: PRT
<213> ORGANISM: Artificial Sequence
<220> FEATURE:
<223> OTHER INFORMATION: Synthetic peptide

<400> SEQUENCE: 19

Leu Arg Ser Ile Gly Lys Asp Leu Arg Ser Ile Gly Lys Asp Leu Arg
1               5               10              15

Ser Ile Gly Lys Asp Leu Arg Ser Ile Gly Lys Asp
            20              25

<210> SEQ ID NO 20
<211> LENGTH: 29
<212> TYPE: PRT
<213> ORGANISM: Artificial Sequence
<220> FEATURE:
<223> OTHER INFORMATION: Synthetic peptide

<400> SEQUENCE: 20

Leu Arg Ser Ile Gly Lys Asp Leu Arg Ser Ile Gly Lys Asp Leu Arg
1               5               10              15

Ser Ile Gly Lys Asp Leu Arg Ser Ile Gly Lys Asp Ser
            20              25

<210> SEQ ID NO 21
<211> LENGTH: 28
<212> TYPE: PRT
<213> ORGANISM: Artificial Sequence
<220> FEATURE:
<223> OTHER INFORMATION: Synthetic peptide

<400> SEQUENCE: 21

Leu Arg Ser Ile Gly Lys Asp Leu Arg Ser Ile Gly Arg Asp Leu Arg
1               5               10              15

Ser Ile Gly Lys Asp Leu Arg Ser Ile Gly Arg Asp
            20              25

<210> SEQ ID NO 22
<211> LENGTH: 28
<212> TYPE: PRT
<213> ORGANISM: Artificial Sequence
<220> FEATURE:
<223> OTHER INFORMATION: Synthetic peptide

<400> SEQUENCE: 22

Ile Arg Glu Ile Ser Arg Ala Ile Arg Glu Val Ala Gln Ser Ile Arg
1               5               10              15

Asp Ile Ala Lys Ala Ile Arg Glu Ile Gly Lys Ser
            20              25

<210> SEQ ID NO 23
<211> LENGTH: 28
<212> TYPE: PRT
<213> ORGANISM: Artificial Sequence
<220> FEATURE:
<223> OTHER INFORMATION: Synthetic peptide

<400> SEQUENCE: 23

Ile Arg Asp Ile Gly Arg Ala Ile Arg Asp Val Gly Gln Ser Ile Arg
1               5               10              15
```

-continued

Asp Leu Ala Lys Gly Ile Arg Asp Ile Ser Lys Gly
            20                  25

<210> SEQ ID NO 24
<211> LENGTH: 28
<212> TYPE: PRT
<213> ORGANISM: Artificial Sequence
<220> FEATURE:
<223> OTHER INFORMATION: Synthetic peptide

<400> SEQUENCE: 24

Val Lys Asp Val Ala Arg Gly Ile Arg Asp Ile Gly Asn Ser Ile Lys
1               5                   10                  15

Asp Leu Ala Arg Gly Ile Arg Asp Ile Gly Arg Gly
            20                  25

<210> SEQ ID NO 25
<211> LENGTH: 28
<212> TYPE: PRT
<213> ORGANISM: Artificial Sequence
<220> FEATURE:
<223> OTHER INFORMATION: Synthetic peptide

<400> SEQUENCE: 25

Leu Arg Ser Ile Gly Lys Asp Leu Arg Ser Ile Gly Arg Asp Leu Arg
1               5                   10                  15

Ser Ile Gly Lys Asp Leu Arg Ser Ile Gly Arg Asp
            20                  25

<210> SEQ ID NO 26
<211> LENGTH: 28
<212> TYPE: PRT
<213> ORGANISM: Artificial Sequence
<220> FEATURE:
<223> OTHER INFORMATION: Synthetic peptide

<400> SEQUENCE: 26

Ile Arg Glu Ile Ser Arg Ala Ile Arg Glu Val Ala Gln Ser Ile Arg
1               5                   10                  15

Asp Ile Ala Lys Ala Ile Arg Glu Ile Gly Lys Ser
            20                  25

<210> SEQ ID NO 27
<211> LENGTH: 28
<212> TYPE: PRT
<213> ORGANISM: Artificial Sequence
<220> FEATURE:
<223> OTHER INFORMATION: Synthetic peptide

<400> SEQUENCE: 27

Ile Arg Asp Ile Gly Arg Ala Ile Arg Asp Val Gly Gln Ser Ile Arg
1               5                   10                  15

Asp Leu Ala Lys Gly Ile Arg Asp Ile Ser Lys Gly
            20                  25

<210> SEQ ID NO 28
<211> LENGTH: 28
<212> TYPE: PRT
<213> ORGANISM: Artificial Sequence
<220> FEATURE:
<223> OTHER INFORMATION: Synthetic peptide

<400> SEQUENCE: 28

Val Lys Asp Val Ala Arg Gly Ile Arg Asp Ile Gly Asn Ser Ile Lys
1               5                   10                  15

-continued

Asp Leu Ala Arg Gly Ile Arg Asp Ile Gly Arg Gly
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide

<400> SEQUENCE: 29

Ile Arg Ser Ile Gly Lys Glu Ile Arg Ser Ile Gly Arg Glu Ile Lys
1               5                   10                  15

Ser Ile Gly Arg Glu Ile Arg Ser Ile Gly Arg Gly
            20                  25

<210> SEQ ID NO 30
<211> LENGTH: 28
<212> TYPE: PRT
<213> ORGANISM: Artificial Sequence
<220> FEATURE:
<223> OTHER INFORMATION: Synthetic peptide

<400> SEQUENCE: 30

Ile Arg Ser Ile Gly Lys Glu Ile Arg Ser Ile Gly Arg Glu Ile Arg
1               5                   10                  15

Ser Ile Gly Lys Glu Ile Arg Ser Ile Gly Arg Glu
            20                  25

<210> SEQ ID NO 31
<211> LENGTH: 28
<212> TYPE: PRT
<213> ORGANISM: Artificial Sequence
<220> FEATURE:
<223> OTHER INFORMATION: Synthetic peptide

<400> SEQUENCE: 31

Ile Arg Ser Ile Gly Lys Glu Ile Arg Ser Ile Gly Arg Glu Ile Arg
1               5                   10                  15

Ser Ile Gly Arg Glu Ile Arg Ser Ile Gly Arg Glu
            20                  25

<210> SEQ ID NO 32
<211> LENGTH: 15
<212> TYPE: PRT
<213> ORGANISM: Clostridium botulinum

<400> SEQUENCE: 32

Leu Leu Val Leu Val Phe Thr Phe Ser Leu Ile Ile Ser Ala Ser
1               5                   10                  15

<210> SEQ ID NO 33
<211> LENGTH: 15
<212> TYPE: PRT
<213> ORGANISM: Clostridium botulinum

<400> SEQUENCE: 33

Phe Ser Leu Ile Ile Ser Ala Ser Ser Ala Asn Gln Val Tyr Ala
1               5                   10                  15

<210> SEQ ID NO 34
<211> LENGTH: 15
<212> TYPE: PRT
<213> ORGANISM: Clostridium perfringens -continued

<400> SEQUENCE: 34

```
Arg Leu Ile Thr Ala Met Ile Leu Ala Gly Ala Ile Ser Ile Gly
1               5                   10                  15
```

<210> SEQ ID NO 35
<211> LENGTH: 15
<212> TYPE: PRT
<213> ORGANISM: Staphylococcus aureus

<400> SEQUENCE: 35

```
Asn Arg Asn Phe Leu Gln Arg Ile Trp Asp Ala Ile Val Ala Phe
1               5                   10                  15
```

<210> SEQ ID NO 36
<211> LENGTH: 15
<212> TYPE: PRT
<213> ORGANISM: Artificial Sequence
<220> FEATURE:
<223> OTHER INFORMATION: Mycobacterium

<400> SEQUENCE: 36

```
Thr Pro Ser Thr Asp Ser Thr Ala Phe Thr Ala Val Ala Gln Glu
1               5                   10                  15
```

<210> SEQ ID NO 37
<211> LENGTH: 15
<212> TYPE: PRT
<213> ORGANISM: Artificial Sequence
<220> FEATURE:
<223> OTHER INFORMATION: Mycobacterium

<400> SEQUENCE: 37

```
Arg Gly Gln Phe Asp Arg Phe Thr Arg Asp Thr Gly Ile Ala Val
1               5                   10                  15
```

<210> SEQ ID NO 38
<211> LENGTH: 15
<212> TYPE: PRT
<213> ORGANISM: Artificial Sequence
<220> FEATURE:
<223> OTHER INFORMATION: Mycobacterium

<400> SEQUENCE: 38

```
Gly Gln Phe Asp Arg Phe Thr Arg Asp Thr Gly Ile Ala Val Asn
1               5                   10                  15
```

<210> SEQ ID NO 39
<211> LENGTH: 15
<212> TYPE: PRT
<213> ORGANISM: Artificial Sequence
<220> FEATURE:
<223> OTHER INFORMATION: Mycobacterium

<400> SEQUENCE: 39

```
Phe Thr Arg Asp Thr Gly Ile Ala Val Asn Leu Val Glu Ala Gly
1               5                   10                  15
```

<210> SEQ ID NO 40
<211> LENGTH: 15
<212> TYPE: PRT
<213> ORGANISM: Artificial Sequence
<220> FEATURE:
<223> OTHER INFORMATION: Mycobacterium

<400> SEQUENCE: 40

-continued

```
Val Ile Gly Leu Ala Ala Val Thr Ile Ala Ala Ala Ala Thr Ala
1               5                   10                  15

<210> SEQ ID NO 41
<211> LENGTH: 15
<212> TYPE: PRT
<213> ORGANISM: Clostridium tetani

<400> SEQUENCE: 41

Ile Glu Ile Ile Asp Ser Leu Gln Trp Asp Arg Asn Leu Arg Ile
1               5                   10                  15

<210> SEQ ID NO 42
<211> LENGTH: 15
<212> TYPE: PRT
<213> ORGANISM: Clostridium tetani

<400> SEQUENCE: 42

Glu Ile Ile Asp Ser Leu Gln Trp Asp Arg Asn Leu Arg Ile Asn
1               5                   10                  15

<210> SEQ ID NO 43
<211> LENGTH: 15
<212> TYPE: PRT
<213> ORGANISM: Clostridium tetani

<400> SEQUENCE: 43

Ile Ile Asp Ser Leu Gln Trp Asp Arg Asn Leu Arg Ile Asn Leu
1               5                   10                  15

<210> SEQ ID NO 44
<211> LENGTH: 15
<212> TYPE: PRT
<213> ORGANISM: Mycobacterium tuberculosis

<400> SEQUENCE: 44

Glu Ile Ser Thr Asn Ile Arg Gln Ala Gly Val Gln Tyr Ser Arg
1               5                   10                  15

<210> SEQ ID NO 45
<211> LENGTH: 20
<212> TYPE: PRT
<213> ORGANISM: Mycobacterium tuberculosis

<400> SEQUENCE: 45

Ser Glu Phe Ala Tyr Gly Ser Phe Val Arg Thr Val Ser Leu Pro Val
1               5                   10                  15

Gly Ala Asp Glu
            20

<210> SEQ ID NO 46
<211> LENGTH: 15
<212> TYPE: PRT
<213> ORGANISM: Mumps virus

<400> SEQUENCE: 46

Gly Thr Tyr Arg Leu Ile Pro Asn Ala Arg Ala Asn Leu Thr Ala
1               5                   10                  15

<210> SEQ ID NO 47
<211> LENGTH: 16
<212> TYPE: PRT
<213> ORGANISM: Plasmodium falciparum

<400> SEQUENCE: 47
```

```
Glu Glu Asn Val Glu Glu Asn Val Glu Glu Asn Val Glu Glu Asn Val
1               5                   10                  15

<210> SEQ ID NO 48
<211> LENGTH: 20
<212> TYPE: PRT
<213> ORGANISM: Human immunodeficiency virus type 1

<400> SEQUENCE: 48

Ala Phe Ser Pro Glu Val Ile Pro Met Phe Ser Ala Leu Ser Glu Gly
1               5                   10                  15

Ala Thr Pro Gln
            20

<210> SEQ ID NO 49
<211> LENGTH: 21
<212> TYPE: PRT
<213> ORGANISM: Hepatitis C virus

<400> SEQUENCE: 49

Gly Glu Gly Ala Val Gln Trp Met Asn Arg Leu Ile Ala Phe Ala Ser
1               5                   10                  15

Arg Gly Asn His Val
            20

<210> SEQ ID NO 50
<211> LENGTH: 11
<212> TYPE: PRT
<213> ORGANISM: Influenza A virus

<400> SEQUENCE: 50

Phe Val Phe Thr Leu Thr Val Pro Ser Glu Arg
1               5                   10

<210> SEQ ID NO 51
<211> LENGTH: 20
<212> TYPE: PRT
<213> ORGANISM: Influenza A virus

<400> SEQUENCE: 51

Leu Val Val Pro Arg Tyr Ala Phe Ala Met Glu Arg Asn Ala Gly Ser
1               5                   10                  15

Gly Ile Ile Ile
            20

<210> SEQ ID NO 52
<211> LENGTH: 7
<212> TYPE: PRT
<213> ORGANISM: Artificial Sequence
<220> FEATURE:
<223> OTHER INFORMATION: TLR-4 agonist

<400> SEQUENCE: 52

Ala Pro Pro His Ala Leu Ser
1               5

<210> SEQ ID NO 53
<211> LENGTH: 4
<212> TYPE: PRT
<213> ORGANISM: Artificial Sequence
<220> FEATURE:
<223> OTHER INFORMATION: Synthetic peptide

<400> SEQUENCE: 53
```

Gly Glu Asp Cys
1

<210> SEQ ID NO 54
<211> LENGTH: 35
<212> TYPE: PRT
<213> ORGANISM: Artificial Sequence
<220> FEATURE:
<223> OTHER INFORMATION: Synthetic peptide

<400> SEQUENCE: 54

Val Ser Val Leu Tyr Asn Ser Ala Ser Phe Ser Thr Phe Lys Ser Tyr
1               5                   10                  15

Gly Val Ser Pro Thr Lys Leu Asn Asp Leu Ser Phe Thr Asn Asp Asp
            20                  25                  30

Glu Asp Cys
        35

<210> SEQ ID NO 55
<211> LENGTH: 38
<212> TYPE: PRT
<213> ORGANISM: Artificial Sequence
<220> FEATURE:
<223> OTHER INFORMATION: Synthetic peptide

<400> SEQUENCE: 55

Val Asn Tyr Asn Tyr Leu Tyr Arg Leu Phe Arg Lys Ser Asn Leu Lys
1               5                   10                  15

Pro Phe Glu Arg Asp Ile Ser Thr Glu Ile Tyr Gln Ala Gly Ser Thr
            20                  25                  30

Pro Asp Asp Glu Asp Cys
        35

<210> SEQ ID NO 56
<211> LENGTH: 31
<212> TYPE: PRT
<213> ORGANISM: Artificial Sequence
<220> FEATURE:
<223> OTHER INFORMATION: Synthetic peptide

<400> SEQUENCE: 56

Val Asn Gly Val Glu Gly Phe Asn Cys Tyr Phe Pro Leu Gln Ser Tyr
1               5                   10                  15

Gly Phe Gln Pro Thr Asn Gly Val Gly Tyr Gln Gly Gly Gly Cys
            20                  25                  30

<210> SEQ ID NO 57
<211> LENGTH: 27
<212> TYPE: PRT
<213> ORGANISM: Artificial Sequence
<220> FEATURE:
<223> OTHER INFORMATION: Synthetic peptide

<400> SEQUENCE: 57

Val Ser Tyr Gln Thr Gln Thr Asn Ser Pro Arg Arg Ala Arg Ser Val
1               5                   10                  15

Ala Ser Gln Ser Ile Ile Asp Asp Glu Asp Cys
            20                  25

<210> SEQ ID NO 58
<211> LENGTH: 42
<212> TYPE: PRT
<213> ORGANISM: Artificial Sequence
<220> FEATURE:
<223> OTHER INFORMATION: Synthetic peptide

<400> SEQUENCE: 58

Val Cys Gly Pro Lys Lys Ser Thr Asn Leu Val Lys Asn Lys Cys Val
1               5                   10                  15

Asn Phe Asn Phe Asn Gly Leu Thr Gly Thr Gly Val Leu Thr Glu Ser
            20                  25                  30

Asn Lys Lys Phe Leu Asp Asp Glu Asp Cys
        35                  40

<210> SEQ ID NO 59
<211> LENGTH: 34
<212> TYPE: PRT
<213> ORGANISM: Artificial Sequence
<220> FEATURE:
<223> OTHER INFORMATION: Synthetic peptide

<400> SEQUENCE: 59

Val Pro Phe Gln Gln Phe Gly Arg Asp Ile Ala Asp Thr Thr Asp Ala
1               5                   10                  15

Val Arg Asp Pro Gln Thr Leu Glu Ile Leu Asp Ile Thr Asp Asp Glu
            20                  25                  30

Asp Cys

<210> SEQ ID NO 60
<211> LENGTH: 14
<212> TYPE: PRT
<213> ORGANISM: Artificial Sequence
<220> FEATURE:
<223> OTHER INFORMATION: Synthetic peptide

<400> SEQUENCE: 60

Val Ala Ile His Ala Asp Gln Leu Thr Asp Asp Glu Asp Cys
1               5                   10

<210> SEQ ID NO 61
<211> LENGTH: 29
<212> TYPE: PRT
<213> ORGANISM: Artificial Sequence
<220> FEATURE:
<223> OTHER INFORMATION: Synthetic peptide

<400> SEQUENCE: 61

Val Glu Val Pro Val Ala Ile His Ala Asp Gln Leu Thr Pro Thr Trp
1               5                   10                  15

Arg Val Tyr Ser Thr Gly Ser Asn Asp Asp Glu Asp Cys
            20                  25

<210> SEQ ID NO 62
<211> LENGTH: 27
<212> TYPE: PRT
<213> ORGANISM: Artificial Sequence
<220> FEATURE:
<223> OTHER INFORMATION: Synthetic peptide

<400> SEQUENCE: 62

Val Arg Pro Gln Gly Leu Pro Asn Asn Thr Ala Ser Trp Phe Thr Ala
1               5                   10                  15

Leu Thr Gln His Gly Lys Asp Asp Glu Asp Cys
            20                  25

<210> SEQ ID NO 63

```
<211> LENGTH: 26
<212> TYPE: PRT
<213> ORGANISM: Artificial Sequence
<220> FEATURE:
<223> OTHER INFORMATION: Synthetic peptide

<400> SEQUENCE: 63

Val Asn Asn Asn Ala Ala Thr Val Leu Gln Leu Pro Gln Gly Thr Thr
1               5                   10                  15

Leu Pro Lys Gly Phe Asp Asp Glu Asp Cys
            20                  25

<210> SEQ ID NO 64
<211> LENGTH: 31
<212> TYPE: PRT
<213> ORGANISM: Artificial Sequence
<220> FEATURE:
<223> OTHER INFORMATION: Synthetic peptide

<400> SEQUENCE: 64

Val Asn Lys His Ile Asp Ala Tyr Lys Thr Phe Pro Pro Thr Glu Pro
1               5                   10                  15

Lys Lys Asp Lys Lys Lys Lys Thr Asp Glu Asp Asp Glu Asp Cys
            20                  25                  30

<210> SEQ ID NO 65
<211> LENGTH: 28
<212> TYPE: PRT
<213> ORGANISM: Artificial Sequence
<220> FEATURE:
<223> OTHER INFORMATION: Synthetic peptide

<400> SEQUENCE: 65

Val Ala Gln Pro Leu Pro Gln Arg Gln Lys Lys Gln Pro Thr Val Thr
1               5                   10                  15

Leu Leu Pro Ala Ala Asp Met Asp Asp Glu Asp Cys
            20                  25

<210> SEQ ID NO 66
<211> LENGTH: 26
<212> TYPE: PRT
<213> ORGANISM: Artificial Sequence
<220> FEATURE:
<223> OTHER INFORMATION: Synthetic peptide

<400> SEQUENCE: 66

Val Pro Leu Leu Glu Ser Glu Leu Val Ile Gly Ala Val Ile Leu Arg
1               5                   10                  15

Gly His Leu Arg Ile Asp Asp Glu Asp Cys
            20                  25

<210> SEQ ID NO 67
<211> LENGTH: 30
<212> TYPE: PRT
<213> ORGANISM: Artificial Sequence
<220> FEATURE:
<223> OTHER INFORMATION: Synthetic peptide

<400> SEQUENCE: 67

Val Met Ala Asp Ser Asn Gly Thr Ile Thr Val Glu Glu Leu Lys Lys
1               5                   10                  15

Leu Leu Glu Gln Trp Asn Leu Val Ile Asp Asp Glu Asp Cys
            20                  25                  30
```

<210> SEQ ID NO 68
<211> LENGTH: 27
<212> TYPE: PRT
<213> ORGANISM: Artificial Sequence
<220> FEATURE:
<223> OTHER INFORMATION: Synthetic peptide

<400> SEQUENCE: 68

Val Pro Val Ala Ile His Ala Asp Gln Leu Thr Pro Thr Trp Arg Val
1               5                   10                  15

Tyr Ser Thr Gly Ser Asn Asp Asp Glu Asp Cys
            20                  25

<210> SEQ ID NO 69
<211> LENGTH: 24
<212> TYPE: PRT
<213> ORGANISM: Artificial Sequence
<220> FEATURE:
<223> OTHER INFORMATION: Synthetic peptide

<400> SEQUENCE: 69

Val Phe Ser Gln Ile Leu Pro Asp Pro Ser Lys Pro Ser Lys Arg Ser
1               5                   10                  15

Phe Ile Glu Asp Asp Glu Asp Cys
            20

<210> SEQ ID NO 70
<211> LENGTH: 23
<212> TYPE: PRT
<213> ORGANISM: Artificial Sequence
<220> FEATURE:
<223> OTHER INFORMATION: Synthetic peptide

<400> SEQUENCE: 70

Val Thr Glu Ser Ile Val Arg Phe Pro Asn Ile Thr Asn Leu Cys Pro
1               5                   10                  15

Phe Gly Asp Asp Glu Asp Cys
            20

<210> SEQ ID NO 71
<211> LENGTH: 37
<212> TYPE: PRT
<213> ORGANISM: Artificial Sequence
<220> FEATURE:
<223> OTHER INFORMATION: Synthetic peptide

<400> SEQUENCE: 71

Val Gln Asn Val Leu Tyr Glu Asn Gln Lys Leu Ile Ala Asn Gln Phe
1               5                   10                  15

Asn Ser Ala Ile Gly Lys Ile Gln Asp Ser Leu Ser Ser Thr Ala Ser
            20                  25                  30

Asp Asp Glu Asp Cys
        35

<210> SEQ ID NO 72
<211> LENGTH: 21
<212> TYPE: PRT
<213> ORGANISM: Artificial Sequence
<220> FEATURE:
<223> OTHER INFORMATION: Synthetic peptide

<400> SEQUENCE: 72

Val Tyr Val Pro Ala Gln Glu Lys Asn Phe Thr Thr Ala Pro Ala Ile
1               5                   10                  15

```
Asp Asp Glu Asp Cys
            20

<210> SEQ ID NO 73
<211> LENGTH: 24
<212> TYPE: PRT
<213> ORGANISM: Artificial Sequence
<220> FEATURE:
<223> OTHER INFORMATION: Synthetic peptide

<400> SEQUENCE: 73

Val Ser Phe Ile Glu Asp Leu Leu Phe Asn Lys Val Thr Leu Ala Asp
1               5                   10                  15

Ala Gly Phe Asp Asp Glu Asp Cys
            20

<210> SEQ ID NO 74
<211> LENGTH: 41
<212> TYPE: PRT
<213> ORGANISM: Artificial Sequence
<220> FEATURE:
<223> OTHER INFORMATION: Synthetic peptide

<400> SEQUENCE: 74

Val Cys Asp Asp Glu Asp Asp Phe His Phe Glu Val Phe Asn Phe Val
1               5                   10                  15

Pro Cys Ser Ile Cys Ser Asn Asn Pro Thr Cys Trp Ala Ile Cys Lys
            20                  25                  30

Arg Ile Pro Asn Lys Lys Pro Gly Lys
        35                  40

<210> SEQ ID NO 75
<211> LENGTH: 29
<212> TYPE: PRT
<213> ORGANISM: Artificial Sequence
<220> FEATURE:
<223> OTHER INFORMATION: Synthetic peptide

<400> SEQUENCE: 75

Val Asp Lys Gln Leu Leu Pro Ile Leu Asn Lys Gln Ser Cys Ser Ile
1               5                   10                  15

Ser Asn Ile Glu Thr Val Ile Glu Asp Asp Glu Asp Cys
            20                  25

<210> SEQ ID NO 76
<211> LENGTH: 19
<212> TYPE: PRT
<213> ORGANISM: Artificial Sequence
<220> FEATURE:
<223> OTHER INFORMATION: Synthetic peptide

<400> SEQUENCE: 76

Arg Phe Glu Ile Phe Pro Lys Thr Ser Ser Trp Pro Asn His Asp Ser
1               5                   10                  15

Asn Lys Gly

<210> SEQ ID NO 77
<211> LENGTH: 19
<212> TYPE: PRT
<213> ORGANISM: Artificial Sequence
<220> FEATURE:
<223> OTHER INFORMATION: Synthetic peptide

<400> SEQUENCE: 77
```

His Pro Ser Thr Ser Ala Asp Gln Gln Ser Leu Tyr Gln Asn Ala Asp
1               5                   10                  15

Thr Tyr Val

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide

<400> SEQUENCE: 78

Ser Asp Thr Pro Val His Asp Cys Asn
1               5

<210> SEQ ID NO 79
<211> LENGTH: 13
<212> TYPE: PRT
<213> ORGANISM: Artificial Sequence
<220> FEATURE:
<223> OTHER INFORMATION: Synthetic peptide

<400> SEQUENCE: 79

Ser Val Asn Leu Leu Glu Asp Lys His Asn Gly Lys Leu
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic peptide

<400> SEQUENCE: 80

Ile Ser Asp Thr Pro Val His Asp Cys Asn Thr Thr
1               5                   10

<210> SEQ ID NO 81
<211> LENGTH: 19
<212> TYPE: PRT
<213> ORGANISM: Artificial Sequence
<220> FEATURE:
<223> OTHER INFORMATION: Synthetic peptide

<400> SEQUENCE: 81

Lys Lys Gly Asn Ser Tyr Pro Lys Leu Ser Lys Ser Tyr Ile Asn Asp
1               5                   10                  15

Lys Gly Glu

<210> SEQ ID NO 82
<211> LENGTH: 8
<212> TYPE: PRT
<213> ORGANISM: Artificial Sequence
<220> FEATURE:
<223> OTHER INFORMATION: Synthetic peptide

<400> SEQUENCE: 82

Cys Pro His Ala Gly Ala Lys Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide

<400> SEQUENCE: 83

Ser Leu Ser Thr Ala Ser Ser
1               5

<210> SEQ ID NO 84
<211> LENGTH: 34
<212> TYPE: PRT
<213> ORGANISM: Artificial Sequence
<220> FEATURE:
<223> OTHER INFORMATION: Synthetic peptide

<400> SEQUENCE: 84

Trp Gly Asp Gly Ile Leu Glu Ser Asp Leu Ile Ile Pro Val Thr Leu
1               5                   10                  15

Ala Gly Pro Arg Ser Asn His Asn Arg Arg Pro Gly Tyr Lys Thr Gln
            20                  25                  30

Asn Gln

<210> SEQ ID NO 85
<211> LENGTH: 37
<212> TYPE: PRT
<213> ORGANISM: Artificial Sequence
<220> FEATURE:
<223> OTHER INFORMATION: Synthetic peptide

<400> SEQUENCE: 85

Cys Pro Thr Met Gly Glu Ala His Asn Asp Lys Arg Ala Asp Pro Ala
1               5                   10                  15

Phe Val Cys Arg Gln Gly Val Val Asp Arg Gly Trp Gly Asn Gly Cys
            20                  25                  30

Gly Leu Phe Gly Lys
        35

<210> SEQ ID NO 86
<211> LENGTH: 27
<212> TYPE: PRT
<213> ORGANISM: Artificial Sequence
<220> FEATURE:
<223> OTHER INFORMATION: Synthetic peptide

<400> SEQUENCE: 86

Pro Pro Phe Gly Asp Ser Tyr Ile Val Val Gly Arg Gly Glu Gln Gln
1               5                   10                  15

Ile Asn His His Trp His Lys Ser Gly Ser Ser
            20                  25

<210> SEQ ID NO 87
<211> LENGTH: 18
<212> TYPE: PRT
<213> ORGANISM: Artificial Sequence
<220> FEATURE:
<223> OTHER INFORMATION: Synthetic peptide

<400> SEQUENCE: 87

Glu Phe Glu Glu Pro His Ala Thr Lys Gln Ser Val Ile Ala Leu Gly
1               5                   10                  15

Ser Gln

<210> SEQ ID NO 88
<211> LENGTH: 23
<212> TYPE: PRT
<213> ORGANISM: Artificial Sequence
<220> FEATURE:
<223> OTHER INFORMATION: Synthetic peptide

<400> SEQUENCE: 88

Met Ser Phe Val Lys Asn Pro Thr Asp Thr Gly His Gly Thr Val Val
1               5                   10                  15

Met Gln Val Lys Val Pro Lys
            20

<210> SEQ ID NO 89
<211> LENGTH: 24
<212> TYPE: PRT
<213> ORGANISM: Artificial Sequence
<220> FEATURE:
<223> OTHER INFORMATION: Synthetic peptide

<400> SEQUENCE: 89

Val Leu Thr His Val Lys Ile Asn Asp Lys Cys Pro Ser Thr Gly Glu
1               5                   10                  15

Ala His Leu Ala Glu Glu Asn Glu
            20

<210> SEQ ID NO 90
<211> LENGTH: 23
<212> TYPE: PRT
<213> ORGANISM: Artificial Sequence
<220> FEATURE:
<223> OTHER INFORMATION: Synthetic peptide

<400> SEQUENCE: 90

Asn Ala Cys Lys Arg Thr Tyr Ser Asp Arg Gly Trp Gly Asn Gly Cys
1               5                   10                  15

Gly Leu Phe Gly Lys Gly Ser
            20

<210> SEQ ID NO 91
<211> LENGTH: 19
<212> TYPE: PRT
<213> ORGANISM: Artificial Sequence
<220> FEATURE:
<223> OTHER INFORMATION: Synthetic peptide

<400> SEQUENCE: 91

Glu Pro Pro His Ala Ala Thr Ile Arg Val Leu Ala Leu Gly Asn Gln
1               5                   10                  15

Glu Gly Ser

<210> SEQ ID NO 92
<211> LENGTH: 24
<212> TYPE: PRT
<213> ORGANISM: Artificial Sequence
<220> FEATURE:
<223> OTHER INFORMATION: Synthetic peptide

<400> SEQUENCE: 92

Lys Phe Asp Asp Thr Glu Thr Ser Asn Arg Tyr Pro Ala Gln Pro Gly
1               5                   10                  15

Ser Asp Asn Arg Glu Cys Leu Ser
            20

<210> SEQ ID NO 93
<211> LENGTH: 23
<212> TYPE: PRT
<213> ORGANISM: Artificial Sequence

```
<220> FEATURE:
<223> OTHER INFORMATION: Synthetic peptide

<400> SEQUENCE: 93

Ala Val Gly Glu Asn Val Pro Asp Asp Leu Tyr Ile Lys Gly Ser Gly
1               5                   10                  15

Ser Thr Ala Asn Leu Ala Ser
            20

<210> SEQ ID NO 94
<211> LENGTH: 15
<212> TYPE: PRT
<213> ORGANISM: Artificial Sequence
<220> FEATURE:
<223> OTHER INFORMATION: Synthetic peptide

<400> SEQUENCE: 94

Lys Gly Thr Gln Ser Ser Asn Thr Ser Val Gln Asn Gly Asp Cys
1               5                   10                  15

<210> SEQ ID NO 95
<211> LENGTH: 12
<212> TYPE: PRT
<213> ORGANISM: Artificial Sequence
<220> FEATURE:
<223> OTHER INFORMATION: Synthetic peptide

<400> SEQUENCE: 95

Ser Ile Lys Lys Val Asn Lys Thr Val Val Pro Lys
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Synthetic peptide

<400> SEQUENCE: 96

Ala Ser Val Ser Lys Ser Ala Thr Tyr Thr Asn Ser Asp
1               5                   10

<210> SEQ ID NO 97
<211> LENGTH: 19
<212> TYPE: PRT
<213> ORGANISM: Artificial Sequence
<220> FEATURE:
<223> OTHER INFORMATION: Synthetic peptide

<400> SEQUENCE: 97

Thr Asn Thr Thr Thr Glu Ser Arg Cys Pro Thr Gln Gly Glu Pro Ser
1               5                   10                  15

Leu Asn Glu

<210> SEQ ID NO 98
<211> LENGTH: 21
<212> TYPE: PRT
<213> ORGANISM: Artificial Sequence
<220> FEATURE:
<223> OTHER INFORMATION: Synthetic peptide

<400> SEQUENCE: 98

Met Val Asp Arg Gly Trp Gly Asn Gly Cys Gly Leu Phe Gly Lys Gly
1               5                   10                  15

Gly Ile Val Thr Cys
```

```
                20

<210> SEQ ID NO 99
<211> LENGTH: 10
<212> TYPE: PRT
<213> ORGANISM: Artificial Sequence
<220> FEATURE:
<223> OTHER INFORMATION: Synthetic peptide

<400> SEQUENCE: 99

Asp Lys Glu Met Ala Glu Thr Gln His Gly
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic peptide

<400> SEQUENCE: 100

Ile Ile Gly Val Glu Pro Gly Gln Leu Lys Leu Asn
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic peptide

<400> SEQUENCE: 101

Tyr Glu Gly Asp Gly Ser Pro Cys Lys Ile Pro Phe Glu Ile
1               5                   10

<210> SEQ ID NO 102
<211> LENGTH: 8
<212> TYPE: PRT
<213> ORGANISM: Artificial Sequence
<220> FEATURE:
<223> OTHER INFORMATION: Synthetic peptide

<400> SEQUENCE: 102

Ser Met Cys Thr Gly Lys Phe Lys
1               5

<210> SEQ ID NO 103
<211> LENGTH: 4
<212> TYPE: PRT
<213> ORGANISM: Artificial Sequence
<220> FEATURE:
<223> OTHER INFORMATION: Synthetic peptide

<400> SEQUENCE: 103

Gly Gly Gly Cys
1

<210> SEQ ID NO 104
<211> LENGTH: 5
<212> TYPE: PRT
<213> ORGANISM: Artificial Sequence
<220> FEATURE:
<223> OTHER INFORMATION: Synthetic peptide

<400> SEQUENCE: 104

Gly Pro Gly Pro Gly
1               5
```

```
<210> SEQ ID NO 105
<211> LENGTH: 9
<212> TYPE: PRT
<213> ORGANISM: Artificial Sequence
<220> FEATURE:
<223> OTHER INFORMATION: Synthetic peptide

<400> SEQUENCE: 105

Ala Ser Asn Glu Asn Met Glu Thr Met
1               5

<210> SEQ ID NO 106
<211> LENGTH: 14
<212> TYPE: PRT
<213> ORGANISM: Artificial Sequence
<220> FEATURE:
<223> OTHER INFORMATION: Synthetic peptide

<400> SEQUENCE: 106

Gln Tyr Ile Arg Ala Asn Ser Arg Phe Ile Gly Ile Thr Glu
1               5                   10

<210> SEQ ID NO 107
<211> LENGTH: 15
<212> TYPE: PRT
<213> ORGANISM: Artificial Sequence
<220> FEATURE:
<223> OTHER INFORMATION: Synthetic peptide

<400> SEQUENCE: 107

Phe Gln Asp Ala Tyr Asn Ala Ala Gly Gly His Asn Ala Val Phe
1               5                   10                  15

<210> SEQ ID NO 108
<211> LENGTH: 9
<212> TYPE: PRT
<213> ORGANISM: Artificial Sequence
<220> FEATURE:
<223> OTHER INFORMATION: Synthetic peptide

<400> SEQUENCE: 108

Arg Leu Asn Glu Leu Leu Ala Tyr Val
1               5

<210> SEQ ID NO 109
<211> LENGTH: 4
<212> TYPE: PRT
<213> ORGANISM: Artificial Sequence
<220> FEATURE:
<223> OTHER INFORMATION: Synthetic peptide

<400> SEQUENCE: 109

Gly Pro Gly Pro
1

<210> SEQ ID NO 110
<211> LENGTH: 6
<212> TYPE: PRT
<213> ORGANISM: Artificial Sequence
<220> FEATURE:
<223> OTHER INFORMATION: Synthetic peptide

<400> SEQUENCE: 110

Gly Pro Gly Pro Gly Cys
1               5
```

<210> SEQ ID NO 111
<211> LENGTH: 6
<212> TYPE: PRT
<213> ORGANISM: Artificial Sequence
<220> FEATURE:
<223> OTHER INFORMATION: Synthetic peptide

<400> SEQUENCE: 111

Ser Gly Pro Gly Pro Gly
1               5

<210> SEQ ID NO 112
<211> LENGTH: 64
<212> TYPE: PRT
<213> ORGANISM: Artificial Sequence
<220> FEATURE:
<223> OTHER INFORMATION: mouse scaffold peptide

<400> SEQUENCE: 112

Val Ala Ser Asn Glu Asn Met Glu Thr Met Gly Pro Gly Pro Gly Asp
1               5                   10                  15

Ile Arg Ser Ile Gly Lys Glu Ile Arg Ser Ile Gly Arg Glu Ile Arg
                20                  25                  30

Ser Ile Gly Lys Glu Ile Arg Ser Ile Gly Arg Glu Gly Pro Gly Pro
        35                  40                  45

Gly Phe Gln Asp Ala Tyr Asn Ala Ala Gly Gly His Asn Ala Val Phe
    50                  55                  60

<210> SEQ ID NO 113
<211> LENGTH: 58
<212> TYPE: PRT
<213> ORGANISM: Artificial Sequence
<220> FEATURE:
<223> OTHER INFORMATION: human scaffold peptide

<400> SEQUENCE: 113

Val Gln Tyr Ile Arg Ala Asn Ser Arg Phe Ile Gly Ile Thr Glu His
1               5                   10                  15

Ala Ala Asp Ile Arg Ser Ile Gly Lys Glu Ile Arg Ser Ile Gly Arg
                20                  25                  30

Glu Ile Arg Ser Ile Gly Lys Glu Ile Arg Ser Ile Gly Arg Glu Tyr
        35                  40                  45

Arg Arg Leu Asn Glu Leu Leu Ala Tyr Val
    50                  55

<210> SEQ ID NO 114

<400> SEQUENCE: 114

000

<210> SEQ ID NO 115
<211> LENGTH: 32
<212> TYPE: PRT
<213> ORGANISM: Artificial Sequence
<220> FEATURE:
<223> OTHER INFORMATION: Synthetic peptide

<400> SEQUENCE: 115

Val Asn Gly Val Glu Gly Phe Asn Ser Tyr Phe Pro Leu Gln Ser Tyr
1               5                   10                  15

Gly Phe Gln Pro Thr Asn Gly Val Gly Tyr Gln Asp Asp Glu Asp Cys
        20                  25                  30

-continued

```
<210> SEQ ID NO 116
<211> LENGTH: 5
<212> TYPE: PRT
<213> ORGANISM: Artificial Sequence
<220> FEATURE:
<223> OTHER INFORMATION: Synthetic peptide

<400> SEQUENCE: 116

Asp Asp Glu Asp Cys
1               5

<210> SEQ ID NO 117
<211> LENGTH: 29
<212> TYPE: PRT
<213> ORGANISM: SARS-CoV2

<400> SEQUENCE: 117

Ser Val Leu Tyr Asn Ser Ala Ser Phe Ser Thr Phe Lys Cys Tyr Gly
1               5                   10                  15

Val Ser Pro Thr Lys Leu Asn Asp Leu Cys Phe Thr Asn
            20                  25

<210> SEQ ID NO 118
<211> LENGTH: 32
<212> TYPE: PRT
<213> ORGANISM: SARS-CoV2

<400> SEQUENCE: 118

Asn Tyr Asn Tyr Leu Tyr Arg Leu Phe Arg Lys Ser Asn Leu Lys Pro
1               5                   10                  15

Phe Glu Arg Asp Ile Ser Thr Glu Ile Tyr Gln Ala Gly Ser Thr Pro
            20                  25                  30

<210> SEQ ID NO 119
<211> LENGTH: 26
<212> TYPE: PRT
<213> ORGANISM: SARS-CoV2

<400> SEQUENCE: 119

Asn Gly Val Glu Gly Phe Asn Cys Tyr Phe Pro Leu Gln Ser Tyr Gly
1               5                   10                  15

Phe Gln Pro Thr Asn Gly Val Gly Tyr Gln
            20                  25

<210> SEQ ID NO 120
<211> LENGTH: 21
<212> TYPE: PRT
<213> ORGANISM: SARS-CoV2

<400> SEQUENCE: 120

Ser Tyr Gln Thr Gln Thr Asn Ser Pro Arg Arg Ala Arg Ser Val Ala
1               5                   10                  15

Ser Gln Ser Ile Ile
            20

<210> SEQ ID NO 121
<211> LENGTH: 36
<212> TYPE: PRT
<213> ORGANISM: SARS-CoV2

<400> SEQUENCE: 121

Cys Gly Pro Lys Lys Ser Thr Asn Leu Val Lys Asn Lys Cys Val Asn
```

-continued

```
1               5                    10                   15

Phe Asn Phe Asn Gly Leu Thr Gly Thr Gly Val Leu Thr Glu Ser Asn
                20                   25                   30

Lys Lys Phe Leu
        35

<210> SEQ ID NO 122
<211> LENGTH: 28
<212> TYPE: PRT
<213> ORGANISM: SARS-CoV2

<400> SEQUENCE: 122

Pro Phe Gln Gln Phe Gly Arg Asp Ile Ala Asp Thr Thr Asp Ala Val
1               5                    10                   15

Arg Asp Pro Gln Thr Leu Glu Ile Leu Asp Ile Thr
                20                   25

<210> SEQ ID NO 123
<211> LENGTH: 8
<212> TYPE: PRT
<213> ORGANISM: SARS-CoV2

<400> SEQUENCE: 123

Ala Ile His Ala Asp Gln Leu Thr
1               5

<210> SEQ ID NO 124
<211> LENGTH: 23
<212> TYPE: PRT
<213> ORGANISM: SARS-CoV2

<400> SEQUENCE: 124

Glu Val Pro Val Ala Ile His Ala Asp Gln Leu Thr Pro Thr Trp Arg
1               5                    10                   15

Val Tyr Ser Thr Gly Ser Asn
                20

<210> SEQ ID NO 125
<211> LENGTH: 21
<212> TYPE: PRT
<213> ORGANISM: SARS-CoV2

<400> SEQUENCE: 125

Arg Pro Gln Gly Leu Pro Asn Asn Thr Ala Ser Trp Phe Thr Ala Leu
1               5                    10                   15

Thr Gln His Gly Lys
                20

<210> SEQ ID NO 126
<211> LENGTH: 20
<212> TYPE: PRT
<213> ORGANISM: SARS-CoV2

<400> SEQUENCE: 126

Asn Asn Asn Ala Ala Thr Val Leu Gln Leu Pro Gln Gly Thr Thr Leu
1               5                    10                   15

Pro Lys Gly Phe
                20

<210> SEQ ID NO 127
<211> LENGTH: 25
<212> TYPE: PRT
```

-continued

<213> ORGANISM: SARS-CoV2

<400> SEQUENCE: 127

Asn Lys His Ile Asp Ala Tyr Lys Thr Phe Pro Pro Thr Glu Pro Lys
1               5                   10                  15

Lys Asp Lys Lys Lys Lys Thr Asp Glu
            20                  25

<210> SEQ ID NO 128
<211> LENGTH: 22
<212> TYPE: PRT
<213> ORGANISM: SARS-CoV2

<400> SEQUENCE: 128

Ala Gln Pro Leu Pro Gln Arg Gln Lys Lys Gln Pro Thr Val Thr Leu
1               5                   10                  15

Leu Pro Ala Ala Asp Met
            20

<210> SEQ ID NO 129
<211> LENGTH: 20
<212> TYPE: PRT
<213> ORGANISM: SARS-CoV2

<400> SEQUENCE: 129

Pro Leu Leu Glu Ser Glu Leu Val Ile Gly Ala Val Ile Leu Arg Gly
1               5                   10                  15

His Leu Arg Ile
            20

<210> SEQ ID NO 130
<211> LENGTH: 24
<212> TYPE: PRT
<213> ORGANISM: SARS-CoV2

<400> SEQUENCE: 130

Met Ala Asp Ser Asn Gly Thr Ile Thr Val Glu Glu Leu Lys Lys Leu
1               5                   10                  15

Leu Glu Gln Trp Asn Leu Val Ile
            20

<210> SEQ ID NO 131
<211> LENGTH: 21
<212> TYPE: PRT
<213> ORGANISM: SARS-CoV2

<400> SEQUENCE: 131

Pro Val Ala Ile His Ala Asp Gln Leu Thr Pro Thr Trp Arg Val Tyr
1               5                   10                  15

Ser Thr Gly Ser Asn
            20

<210> SEQ ID NO 132
<211> LENGTH: 18
<212> TYPE: PRT
<213> ORGANISM: SARS-CoV2

<400> SEQUENCE: 132

Phe Ser Gln Ile Leu Pro Asp Pro Ser Lys Pro Ser Lys Arg Ser Phe
1               5                   10                  15

Ile Glu

<210> SEQ ID NO 133
<211> LENGTH: 17
<212> TYPE: PRT
<213> ORGANISM: SARS-CoV2

<400> SEQUENCE: 133

Thr Glu Ser Ile Val Arg Phe Pro Asn Ile Thr Asn Leu Cys Pro Phe
1               5                   10                  15

Gly

<210> SEQ ID NO 134
<211> LENGTH: 31
<212> TYPE: PRT
<213> ORGANISM: SARS-CoV2

<400> SEQUENCE: 134

Gln Asn Val Leu Tyr Glu Asn Gln Lys Leu Ile Ala Asn Gln Phe Asn
1               5                   10                  15

Ser Ala Ile Gly Lys Ile Gln Asp Ser Leu Ser Ser Thr Ala Ser
            20                  25                  30

<210> SEQ ID NO 135
<211> LENGTH: 15
<212> TYPE: PRT
<213> ORGANISM: SARS-CoV2

<400> SEQUENCE: 135

Tyr Val Pro Ala Gln Glu Lys Asn Phe Thr Thr Ala Pro Ala Ile
1               5                   10                  15

<210> SEQ ID NO 136
<211> LENGTH: 18
<212> TYPE: PRT
<213> ORGANISM: SARS-CoV2

<400> SEQUENCE: 136

Ser Phe Ile Glu Asp Leu Leu Phe Asn Lys Val Thr Leu Ala Asp Ala
1               5                   10                  15

Gly Phe

<210> SEQ ID NO 137
<211> LENGTH: 5
<212> TYPE: PRT
<213> ORGANISM: Artificial Sequence
<220> FEATURE:
<223> OTHER INFORMATION: Synthetic peptide

<400> SEQUENCE: 137

Asp Gly Glu Gly Cys
1               5

<210> SEQ ID NO 138
<211> LENGTH: 4
<212> TYPE: PRT
<213> ORGANISM: Artificial Sequence
<220> FEATURE:
<223> OTHER INFORMATION: Synthetic peptide

<400> SEQUENCE: 138

Arg Arg Lys Arg
1

<210> SEQ ID NO 139

-continued

```
<211> LENGTH: 26
<212> TYPE: PRT
<213> ORGANISM: Artificial Sequence
<220> FEATURE:
<223> OTHER INFORMATION: Synthetic peptide

<400> SEQUENCE: 139

Asn Gly Val Glu Gly Phe Asn Ser Tyr Phe Pro Leu Gln Ser Tyr Gly
1               5                   10                  15

Phe Gln Pro Thr Asn Gly Val Gly Tyr Gln
            20                  25

<210> SEQ ID NO 140
<211> LENGTH: 29
<212> TYPE: PRT
<213> ORGANISM: Artificial Sequence
<220> FEATURE:
<223> OTHER INFORMATION: Synthetic peptide

<400> SEQUENCE: 140

Ser Val Leu Tyr Asn Ser Ala Ser Phe Ser Thr Phe Lys Ser Tyr Gly
1               5                   10                  15

Val Ser Pro Thr Lys Leu Asn Asp Leu Ser Phe Thr Asn
            20                  25
```

VACCINES AGAINST VIRAL PATHOGENS

CROSS REFERENCE TO RELATED APPLICATIONS

This application is a U.S. National Phase Application of International Application No. PCT/US2021/030579, filed May 4, 2021, which claims the benefit of U.S. Provisional Patent Application 63/019,654, filed on May 4, 2020, which is hereby incorporated by reference in its entirety.

SEQUENCE LISTING INFORMATION

A computer readable textfile, entitled "H197-0006PCT_ST25.txt," created on or about May 3, 2021, with a file size of about 64.4 KB, contains the sequence listing for this application and is hereby incorporated by reference in its entirety.

TECHNICAL FIELD

The present disclosure describes vaccines against viral pathogens.

BACKGROUND

A pathogen is an infectious agent that causes a disease. The infectious agent can be a microorganism such as a virus. Viruses are small particles of about 20 to 300 nanometers in length containing RNA or DNA. They infect all types of life forms including humans, animals, plants, and other microorganisms such as bacteria and archaea. They replicate only inside the living cells of an organism and cause infectious diseases ranging from common cold, flu, arts to severe diseases such as smallpox, influenza, mumps, measles, chickenpox, polio, and rubella.

Vaccines have been developed for a number of infectious diseases and have successfully reduced the incidence of influenza, for example, mumps, measles, small pox, chicken pox, polio, and rubella. Recombinant protein expression in hosts such as bacteria (predominantly *E. coli*), yeast, insect cells, and mammalian cells is currently the most common method of producing subunit vaccines, such a method has been very successful and will remain an important method of vaccine production. Typically, an infectious agent protein is identified by genomics analysis, functional assays, in silico analyses (e.g. functional prediction, structural analysis, epitope identification, etc.), or a combination of the three. Expression trials are initiated to assess yield and solubility for immunogenicity trials. Subunits producing high-titer antibodies to the disease target are then carried forward for protection studies where the vaccine is tested for its ability to protect hosts against infection and/or disease manifestation and progression. Subunits meeting all these criteria are then moved forward for vaccine production optimization, stability, and toxicity/safety/dosage studies. Expression optimization studies are also important to determine production scale and feasibility. The entire process is time-consuming, laborintensive, and very costly.

Therefore, there is also a need to develop a more efficient and cost-effective method for producing vaccines for treating and/or preventing viral diseases and infections.

SUMMARY

This Summary is provided to introduce a selection of concepts in a simplified form that is further described below in the Detailed Description. This Summary is not intended to identify all key features or essential features of the claimed subject matter, nor is it intended to be used alone as an aid in determining the scope of the claimed subject matter.

The present disclosure describes a hMP polypeptide including a hapten (h) attached to a monomeric peptide (MP). The present disclosure also describes a conjugate including a hapten conjugated to a hapten carrier (hC). The hapten can be a target protein or target antigen. In embodiments, the hapten is a viral peptide (VP); the hMP polypeptide includes a viral peptide (VP) and a MP (VPMP); and the conjugate is VP-hC. In embodiments, the hMP can function as a hC or an oligomer hC, such as HhC (hexamer hC), after self-assembly, because it can adopt the same secondary, tertiary or quaternary structure. In embodiments, when T-cell epitopes are attached to the MP in addition to a viral peptide, the VMP can function similar to a VP-hC conjugate, but without the conjugated viral peptide. The VP is a peptide from viruses such as SARS-CoV-2 virus, Respiratory Syncytial virus, Influenza A virus, West Nile Virus, Yellow Fever Virus, Human Papilloma Virus, and Dengue Virus. In embodiments, the VP is the 51, S2, S3, S4, S5, S6, or M1 peptide from the SAR2-CoV-2 virus. In embodiments, the VP includes an amino acid sequence as set forth in SEQ ID NO: 136, 120, 132, 119, 118, 117, 130, 139, 140, 73, 57, 69, 115, 55, 54, or 67.

The hC described herein includes monomeric peptides that are amphipathic alpha-helices comprising two or more heptad repeats that self-assemble into a dimer, trimer, tetramer, pentamer, hexamer, heptamer, octamer, nanomer, or decamer. Each of the heptads comprises an amino acid sequence as set forth in SEQ ID NO: 1. In embodiments, the monomeric peptides self-assemble into a hexameric hapten carrier (HhC). The hC can also include a target peptide, such as a VP, in which case the hC is VPMP that has self-assembled into an oligomer (VPhC oligomer). In embodiments, the VPMP self-assembles into a hexamer, for example, a hC including a VP joined to a HhC (VPHhC). In embodiments, the conjugate described herein includes a VP conjugated to the HhC (VP-HhC).

Moreover, the present disclosure describes VPhC oligomer or conjugates of VP-hC containing T-cell epitopes at the N- and/or C-termini of the amphipathic alpha-helices of the hC that are part of the monomeric peptide, or that were covalently attached to either VPhC or VP-hC.

In embodiments, the present disclosure describes compositions comprising the VP-hC conjugates or VPhC oligomers described herein and an excipient. In embodiments, the composition is a pharmaceutical composition, which can be used to treat subjects in need thereof, such as to prevent or reduce the risk of a subject from developing a viral disease. The subject could be susceptible to being infected by a virus. The pharmaceutical composition can also be administered to a subject prior to a viral infection to prevent a subject from developing a severe or fatal viral disease and/or by alleviating the symptoms of the viral disease. The VP-hC oligomer or VP-hC conjugate in the pharmaceutical composition can generate antibodies in the subject to inhibit or reduce the function of the virus and protects the subject from developing a severe or fatal viral disease or infection. The pharmaceutical composition can also be administered to a subject in need thereof to generate antibodies to neutralize the virus and alleviate symptoms of a viral infection or disease. In embodiments, the pharmaceutical compositions comprising the VPhC oligomer and VP-hC conjugate can be used as vaccines for preventing and/or treating viral disease or infection.

In embodiments, the present disclosure describes methods of using the VP-hC oligomers or VP-hC conjugates described herein as therapeutics or vaccines, such as an immunogen, for inducing a robust and long-lasting immune response in subjects.

In embodiments, the VP is a SARS-CoV-2 (CoV) peptide, in which case the hC is CoVMP that has self-assembled into an oligomer (CoVhC oligomer). In embodiments, the CoVMP self-assembles into a hexamer, for example, a hC including a CoV peptide joined to a HhC (CoVHhC). In embodiments, the conjugate described herein includes CoV conjugated to the HhC (CoV-HhC).

In embodiments, the viral infection or disease to be treated and/or prevented is SARS-CoV-2.

BRIEF DESCRIPTION OF THE DRAWINGS

FIGS. 3A-3E show IgG titers on d14, d28, d42, d56, and d84, respectively. Prime was on d0 and boosts were on d14 and d28. These results show that each of the vaccine candidates tested produced increased titers relative to controls to varying degrees. Mice immunized with HS2, HS3, HS4, or HM1 consistently produced lower titers than HS1, HS5, and HS6 or sera from Groups 9 and 10. The results from Group 9 mice clearly show that covalent coupling to the scaffold is not necessary to produce a robust immune response.

FIGS. 5A, 5B, 5C, 5D, 5E, 5F, 5G, and 5H show time course plots of IgG titers through d84. The induced immune response was robust and durable up to d84 showing that a combination of T-cell epitopes on the scaffold in combination with adjuvant has the capacity for long-term immunity to SARS-CoV-2

DETAILED DESCRIPTION

Figure 1:
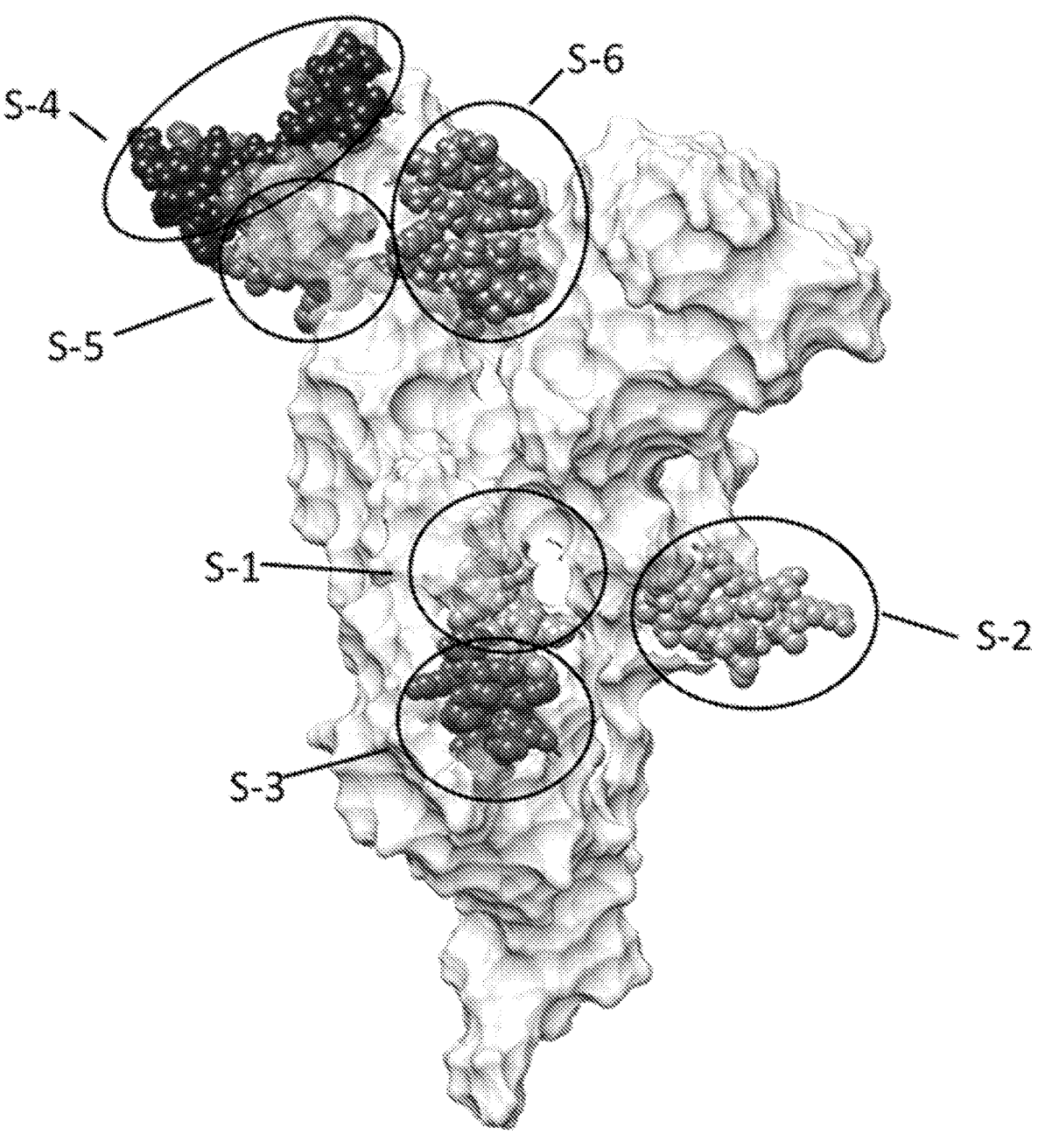
FIG. 1 shows a subunit of the Spike glycoprotein (S-protein) of SARS-CoV-2. The location of the candidate antigenic peptide in the S-protein is shown.

Viral diseases or infections are caused by viruses infecting a subject. Examples of viral diseases include AIDs caused by the Human Immunodeficiency virus (HIV), Hepatitis B caused by the Hepatitis B virus (HBV), Dengue Fever caused by Dengue virus, Influenza caused by the Influenza virus, Yellow Fever caused by the Yellow Fever virus (YFV), Small Pox caused by the Small Pox virus, Severe Acute Respiratory Syndrome (SARS) caused by the SARS Coronavirus, Covid-19 (SARS-CoV-2) caused by the SARS-CoV-2 virus, Respiratory Syncytial Virus (RSV) infection caused by the RSV, Zika fever caused by the Zika virus, Chikungunya infection caused by the Chikungunya virus, West Nile fever caused by West Nile virus (WNV), and Human Papillomavirus infection caused by the Human Papillomavirus (HPV). Vaccines have been developed against some of these viral diseases, but not for all of them. One way to develop a vaccine against a viral disease is to take a peptide from a viral protein or a viral polypeptide and conjugate it to a carrier. However, often the viral peptide or polypeptide is not sufficiently antigenic.

Haptens are molecules that lack antigenic determinants, usually because they are small molecules. In order to become antigenic, they must be coupled to a carrier protein. As used herein, the term "hapten" refers to any molecule that lacks antigenic determinants until it is covalently or non-covalently attached to a carrier protein or a molecule whose antigenicity is increased by covalently or non-covalently coupling to a carrier protein. Similar to haptens, small peptides (i.e. usually those less than 5,000 Daltons) also lack antigenic determinants to induce a robust immune response, so they too must be coupled to a larger carrier protein to be immunogenic.

The present disclosure describes hapten carrier (hC) for peptides, such as viral peptides (VPs). Depending on their size, the VPs are haptens. When a VP is attached to a hC described herein, the VP can induce a robust immune response. VPs are obtained from viral proteins. VPs include small peptides or polypeptides. If the VP is long enough, for example, 15-20 or more residues, co-immunization with a hC without being covalently attached to the hC could be sufficient to induce a robust and long-lasting immune response as long as the hC contains T-cell epitopes able to recruit T-cell help.

In embodiments, the present disclosure also describes a vaccine including a VP-hC conjugate comprising VP covalently attached to the hC and a VPhC oligomer comprising a VP and a monomeric peptide. The vaccine described herein is for preventing and/or treating a viral infection or viral disease. The VPhC oligomer can also include T-cell epitopes. In this manner, the VP vaccines, which include VP-hC conjugate and VPhC oligomer, can induce a robust and long-lasting immune response via both the innate and adaptive pathways to make high titer and high-affinity antibodies targeting endogenous VP. As an example, the VP can induce a robust and long-lasting immune response through T-cell activation, dendritic cell maturation, B-cell activation, proliferation, maturation, establishment of a robust memory response, and other pathways.

After an initial prime/boost, it is expected that antibody titers will be >105. Booster shots could be used to maintain or increase the vaccine's therapeutic efficacy. The side effects of the vaccine will be minimal due to the presence of a precise number of well-characterized and safe T-cell epitopes, the lack of immunodominant epitopes on the hC, and the completely synthetic (non-biological) production of the vaccine. The precise spatial and stoichiometric placement of multiple conformational and linear VP B-cell epitopes on the carrier will result in a potent vaccine capable of preventing and/or treating a viral disease or infection.

Moreover, the present disclosure describes a novel method for producing a VP vaccine comprising a VP-hC conjugate or VPhC oligomer. The method eliminates many of the costliest and time-consuming steps of traditional subunit vaccine development. Instead of producing subunits in recombinant expression hosts, the flexible and modular system uses hC and viral components produced synthetically by solid-phase peptide synthesis (SPPS). The method described herein includes designing a hC component including monomeric peptides that self-assemble into amphipathic alpha-helices to form a carrier complex large enough to induce a robust immune response after one or more VPs are coupled to the hC. In embodiments, the monomeric peptides self-assemble into a hexameric hC (HhC) core, and the VPs can be covalently attached to the HhC core. In embodiments, the HhC core can also include T-cell epitopes at the N- and/or C-terminus of the amphipathic alpha-helices.

The HhC (hexameric oligomer) described herein contains a central region that forms the hexamer core following hydration, and lysines in this region function as a conjugation site for any antigenic peptide or hapten, such as VP to form VP-HhC The size of the HhC can vary according to T-cell epitope length. Upon hexamer formation, the unconjugated hexamer is 38.5 kDa. The conjugated hexamer will be larger depending on the length and size of the conjugated hapten.

The present disclosure describes a core region of the hC that includes a peptide of at least 14 amino acid residues long and comprising at least two heptad repeats, each heptad having the pattern hwxhxyz (SEQ ID NO: 1), wherein
h is a hydrophobic or non-polar residue;
w is a positively charged, negatively charged, polar uncharged, or non-polar aliphatic residue;
x is negatively charged, positively charged, non-polar aliphatic, polar uncharged residue, or any natural or non-natural residue for epitope coupling to a hapten or any other molecule;
y is any natural or non-natural residue for epitope coupling to a hapten or any other molecule; and
z is a negatively charged, positively charged, polar uncharged, non-polar aliphatic residue, or any natural or non-natural residue for epitope coupling to a hapten or any other molecule.

In embodiments, the hC core region includes a peptide having the pattern (hwxhxyz)n (SEQ ID NO: 2), wherein
h is I, L, V, F, W, Y, M, G, or A;
w is G, R, A, N, Q, H, S, D, E, K, or T;
x is R, S, N, Q, A, G, T, D, E, K, H, or C;
y is K, H, C, D, E, R, W, Y, Q, N, or a non-natural amino acid or molecule containing reactive groups amenable to covalent coupling;
Z is A, D, H, S, E, R, N, Q, K, or G; and
n is an integer greater than 1

In embodiments, the exemplary heptads described herein have the following amino acid sequences:

|  | |
|---|---|
| LRSIGKD; | (SEQ ID NO: 3) |
| LRSIGRD; | (SEQ ID NO: 4) |
| IREISRA; | (SEQ ID NO: 5) |
| IREVAQS; | (SEQ ID NO: 6) |
| IRDIAKA; | (SEQ ID NO: 7) |
| IRDIGRA; | (SEQ ID NO: 8) |
| IRDVGQS; | (SEQ ID NO: 9) |
| IRDLAKG; | (SEQ ID NO: 10) |
| VKDVARG; | (SEQ ID NO: 11) |
| IRDIGNS; | (SEQ ID NO: 12) |
| IKDLARG; | (SEQ ID NO: 13) |
| IKKLKKK; | (SEQ ID NO: 14) |
| IRSIGKE; | (SEQ ID NO: 15) |
| IRSIGRE; | (SEQ ID NO: 16) |
| IKSIGRE;<br>or | (SEQ ID NO: 17) |
| IRSIGRG. | (SEQ ID NO: 18) |

In embodiments, the core region of the hC includes one or more heptads described herein, wherein n is 2, 3, 4, 5, 6, 7, 8, 9, 10, or 11.

The present disclosure describes a core region of the hC that includes a peptide of at least 14 residues. In embodiments, the peptide includes 14 residues to 80 residues in length and includes two to 11 heptad repeats. In embodiments, the hC core region includes a peptide comprising 20 to 70 residues, 25 to 60 residues, 28 to 50 residues, 28 to 40 residues, or 28 to 30 residues. The peptides including 14 residues to 80 residues in length are monomers.

The terms "monomeric peptide (MP)" and "monomeric hC (MhC) peptide" are used interchangeably to refer to the monomeric peptides described herein. In embodiments, the exemplary monomeric peptides or monomeric hC peptides described herein include the following amino acid sequences:

```
                                    (SEQ ID NO: 19)
LRSIGKDLRSIGKDLRSIGKDLRSIGKD (SEQ ID NO: 20)
LRSIGKDLRSIGKDLRSIGKDLRSIGKDS;

(SEQ ID NO: 21)
LRSIGKDLRSIGRDLRSIGKDLRSIGRD;

(SEQ ID NO: 22)
IREISRAIREVAQSIRDIAKAIREIGKS;

(SEQ ID NO: 23)
IRDIGRAIRDVGQSIRDLAKGIRDISKG;

(SEQ ID NO: 24)
VKDVARGIRDIGNSIKDLARGIRDIGRG;

(SEQ ID NO: 25)
LRSIGKDLRSIGRDLRSIGKDLRSIGRD;

(SEQ ID NO: 26)
IREISRAIREVAQSIRDIAKAIREIGKS;

(SEQ ID NO: 27)
IRDIGRAIRDVGQSIRDLAKGIRDISKG;

(SEQ ID NO: 28)
VKDVARGIRDIGNSIKDLARGIRDIGRG;

(SEQ ID NO: 29)
IRSIGKEIRSIGREIKSIGREIRSIGRG;

(SEQ ID NO: 30);
IRSIGKEIRSIGREIRSIGKEIRSIGRE;
or (SEQ ID NO: 31)
IRSIGKEIRSIGREIRSIGREIRSIGRE.
```

The peptides described herein can be modified to include one or more substitutions, insertions, and/or deletions and maintain the pattern of hwxhxyz (SEQ ID NO: 1), described above. The modification at each position within the heptad repeat or the peptide must maintain the amphipathic alpha-helical structure, stability, and oligomerization state of the peptide.

In embodiments, the peptides described herein include peptides that comprise an amino acid sequence having at least 70%, 75%, 80%, 85%, 90%, 95%, 96%, 97%, 98%, 99%, or 100% sequence identity to (SEQ ID NO: 3)n, (SEQ ID NO: 4)n, (SEQ ID NO: 5)n (SEQ ID NO: 6)n, (SEQ ID NO: 7)n, (SEQ ID NO: 8)n, (SEQ ID NO: 9)n, (SEQ ID NO: 10)n, (SEQ ID NO: 11)n, (SEQ ID NO: 12)n (SEQ ID NO: 13)n, (SEQ ID NO: 14)n, (SEQ ID NO: 15)n, (SEQ ID NO: 16)n, (SEQ ID NO: 17)n, (SEQ ID NO: 18)n, (SEQ ID NO: 19)n, (SEQ ID NO: 20)n, (SEQ ID NO: 21)n, (SEQ ID NO: 22)n, (SEQ ID NO: 23)n, (SEQ ID NO: 24)n, (SEQ ID NO: 25)n, (SEQ ID NO: 26)n, (SEQ ID NO: 27)n, (SEQ ID NO: 28)n, (SEQ ID NO: 29)n, (SEQ ID NO: 30)n, or (SEQ ID NO: 31)n, wherein n is an integer from 2 to 11. In embodiments, the peptides described herein include peptides that comprise an amino acid sequence having at least 70%, 75%, 80%, 85%, 90%, 95%, 96%, 97%, 98%, 99%, or 100% sequence identity to SEQ ID NO: 19, 20, 21, 22, 23, 24, 25, 26, 27, 28, 29, 30, or 31. Sequence identity refers to the degree of correspondence of two sequences in an alignment, often expressed as a percentage. Differences between two sequences may be determined by methods routinely practiced in the art to determine identity, which is designed to give the greatest match between the sequences tested. Methods to determine sequence identity can be determined by using publicly available computer programs. Computer program methods to determine identity between two sequences include BLASTP. The BLAST family of programs is publicly available from NCBI and other sources.

In embodiments, one or more residues can be added to the N- or C-terminus of the monomer peptides described herein to increase the stability of the peptides in vivo. For example, V (valine), M (methionine), G (glycine), I (isoleucine), D (aspartic acid), or P (proline) or a combination of these residues can be added to the N- or C-terminus of the peptides. Moreover, protective groups can be added to residues to protect the peptides from degradation and increase their stability, especially in vivo. Examples of such protective groups include acetyl, acryl, 9-fluorenylmethoxy-carbonyl, tert-butyloxycarbonyl, allyloxycarbonyl, benzy-loxycarbonyl, and PEG (polyethyleneglycol), and amide on the N- or C-terminus. In embodiments, the amide group protects the C-terminus.

The peptides described herein can be a monomeric hC peptide, but since the monomeric hC peptide is self-assembling, it can self-assemble into a hC that is an oligomer composed of a dimer, trimer, tetramer, pentamer, hexamer, heptamer, octamer, nanomer, or decamer. In embodiments, the monomeric peptide self-assembles into a hexamer, which has six amphipathic alpha-helices. In embodiments, the hC is a hexameric oligomer.

In embodiments, the present disclosure describes a hC that includes one or more residues for conjugating a hapten, such as a VP. The optimal site on the hC for conjugating to hapten is the y residue in the heptad repeat, but VP coupling could also take place at the w, x, and z residues if they contain a reactive side-chain since they are solvent accessible, and the VP can be covalently attached using any residue that can covalently join the VP to the hC, including the HhC. In embodiments, the y residue is K, H, C, D, E, R, W, Y, Q, N, or a non-natural amino acid containing reactive groups amenable to covalent coupling. In embodiments, there are two to four y residues on one side of each of the six amphipathic alpha-helices to provide a coupling site. In embodiments, the y residue is lysine (K).

In embodiments, one or more VP peptides can be conjugated to the MP during SPPS or after MP has assembled into an oligomer, such as a hexamer, using the y residue. The VP conjugated to the hC is conjugate and is referred to as the VP-hC conjugate or VP-oligomer conjugate. In embodiments, the hC is linked to one to 100, 10 to 90, 20 to 80, 30 to 70, 40 to 60, or 50 viral peptides (VPs). In embodiments, the hC is HhC, and the conjugate is the VP-HhC.

In embodiments, the VP can be added during SPPS to the N- and/or C-terminus of the monomeric peptide (prior to self-assembly) to form a VPMP. The VPMP can then self-assemble into an oligomer, such as a VP oligomer or more specifically a VP HhC (VP hexameric hC or VPHhC).

In embodiments, a hMP (hapten attached to a monomeric peptide) can self-assemble into a hhC (hapten attached at the N- or C-terminus of a hapten carrier). When the hapten is VP, the hMP is VPMP, which self-assembles into a VPhC oligomer, for example, a VPHhc (VP joined to a hexameric hapten carrier).

The VPs for producing a vaccine for preventing and/or treating SARS-CoV-2 infection include one or more antigenic peptides of the SARS-CoV-2 virus. The antigenic peptides from SAR-CoV-2 virus can comprise amino acid sequence SEQ ID NO: 117, 118 119, 120, 121, 122, 123, 124, 125, 126, 127, 128, 129, 130, 131, 132, 133, 134, 135, or 136. The antigenic peptides are antigenic peptides from the S glycoprotein (spike glycoprotein), for example, peptide 51, S2, S3, S4, S5, or S6, from the SARS-CoV-2 virus. The antigenic peptide can also include the membrane protein, M1, from the SARS-CoV-2 virus. The antigenic peptides for producing the vaccine against SARS-CoV-2 include 51 (SEQ ID NO: 136), S2 (SEQ ID NO: 120), S3 (SEQ ID NO: 132), S4 (SEQ ID NO: 119), S5 (SEQ ID NO: 118), S6 (SEQ ID NO: 117), and/or M1 (SEQ ID NO: 130). In embodiments, the antigenic peptides include 51 (SEQ ID NO: 136), S5 (SEQ ID NO: 118), and/or S6 (SEQ ID NO: 117).

The VPs for producing a vaccine for preventing and/or treating RSV infection include one or more amino acid sequences SEQ ID NOs: 74 or 75, which are from the RSV.

The VPs for producing a vaccine for preventing and/or treating Influenza caused by Influenza A virus include one or more amino acid sequences SEQ ID NOs: 76, 77, 78, 79, 80, 81, 82, and/or 83, which are from the Influenza A virus.

The VPs for producing a vaccine for preventing or treating West Nile fever include one or more amino acid sequences SEQ ID NOs: 84, 85, 86, and/or 87, which are from the WNV.

The VPs for producing a vaccine for preventing or treating Yellow fever include one or more amino acid sequences SEQ ID NOs: 88, 89, 90, and/or 91, which are from the YFV.

The VPs for producing a vaccine for preventing or treating Human Papilloma infection include one or more amino acid sequences SEQ ID NOs: 92, 93, 94, 95, and/or 96, which are from the HPV.

The VPs for producing a vaccine for preventing or treating Dengue fever include one or more amino acid sequences SEQ ID NOs: 97, 98, 99, 100, 101, and/or 102, which are from the Dengue fever virus.

In embodiments, the wild-type VPs described herein can be modified to produce a useful peptide immunogen. The wild-type VPs can be modified by substitution, deletion, or insertion to include residues that make the peptide more useful and more easily used as a peptide immunogen. The modification does not change the functional property of the VP, such that it can still be used as a peptide immunogen. As an example, C (cysteine) residues can be replaced with an S (serine) residue, as S has similar polarity and shape as C, but its hydroxyl group will not react with the maleimide activated hC, making it easier for conjugation to the hC. In embodiments, modified VP of SARS-CoV2 peptides include the S4 peptide (SEQ ID NO: 139) and S6 peptide (SEQ ID NO: 140).

In embodiments, the one or more VPs that can be attached to the hC can be the same VP or different VPs. As an example, one or more S peptides, such as 51, S2, S3, S4, S5, S6, or M1 can be attached to the same hC. As another example, VPs from different viral strains of SARS-CoV-2 can be attached to the same hC for generating a SARS-CoV-2 vaccine. The different VPs can be attached to the hC simultaneously or separately and then combined.

In the context of the conjugate or oligomer, the term "attached" or "joined" or "coupled" are used interchangeably to refer to conjugated to the self-assembled oligomer (hC) or added to or incorporated into the monomeric peptide during SPPS prior to self-assembly into an oligomer hC.

One or more residues can be added to the N- or C-terminus of the VPs described herein. The one or more residues can make the VP more stable. For example, the one or more residues increase the in vivo half-life of the VP. In embodiments, adding one or more residues to the N-terminus of the VP can increase the in vivo half-life of the VP more than about 5 times to more than about 100 times longer than the half-life of a VP peptide without one or more added residues at its N- or C-terminus. In embodiments, one or more residues can increase the in vivo half-life of the VP more than 5 times, 10 times, 15 times, 20 times, 25 times, 30 times, 35 times, 40 times, 45 times, 50 times, 60 times, 70 times, 80 times, 90 times, or 100 times, times longer than the in vivo half-life of a VP without an added residue at its N- or C-terminus. In embodiments, residues such as G (glycine), V (valine), M (methionine), or A (alanine), or a combination thereof can be added to the N- or C-terminus of the VP for stability. In embodiments, V is added to the N-terminus of the VP to improve its in vivo half-life from about 60 minutes to 100 hours.

In embodiments, the N-terminus of the VP can also be protected with an acetylated group, and/or the C-terminus can be protected with an amide group. In embodiments, adding valine to the N-terminus of the VP and protecting the valine with an acetyl group can increase the in vivo half-life to even longer than 100 hours.

Other residues also can be added to the N- or C-terminus of the one or more VPs to help with conjugation to the hC. For example, one or more residues can be added to the N- or C-terminus of the VP to reduce the pI (isoelectric point) sufficiently which decreased the electrostatic repulsion with the hC. As an example, residues GEDC (SEQ ID NO: 53), DGEGC (SEQ ID NO: 137), or DDEDC (SEQ ID NO: 116) can be added to the C-terminus or N-terminus as a linker for conjugation and to modify the pI of the VP if necessary. As an example, if the hC has a pI value greater than 7, then the DDEDC can be used to lower the pI of the VP to attenuate charge repulsion, which can significantly affect the efficiency of the conjugation. If the scaffold pI is acidic (around 4 or 5), DDEDC would be changed to RRKR (SEQ ID NO: 138) to increase the pI of the peptide. The residues to be added will depend on the sequence of the core region as well as T-cell epitopes on the N- and C-termini, as they will affect the pI of the hC. When there isn't a need to modify the pI of the VP, a linker comprising G residues such as GGGC (SEQ ID NO: 103) is added.

Optionally, other molecules can be conjugated directly to the hC oligomer, such as the HhC, along with the VP. Other molecules also can be attached to the VP and then conjugated to the hC. Moreover, as mentioned herein, VP can be attached to the N- or C-terminus of the hC monomeric peptide during SPPS to form VPMP prior to self-assembly into a VPhC oligomer, such as a VPHhC. One or more other molecules in addition to VP can also be attached to the N- or C-terminus of the hC monomeric (MhC) peptide during SPPS prior to self-assembly into a hC oligomer.

Other molecules that can be attached to the hC oligomer or the MP include any agent that can elicit the production of antibodies which are useful for treating, preventing, alleviating the symptoms of viral disease or infection, or reducing the risk of developing a viral disease or infection in a subject. Examples of other molecules in addition to VP include immunomodulators and haptens. Examples of immunomodulators including adjuvant molecules comprise T-cell epitope peptides, nucleic acids, lipids, lipopeptides, lipoproteins, carbohydrates, and short peptides. Peptides that can be used as haptens, including VPs, and B-cell epitopes, include synthetically or recombinantly produced or native peptides or proteins comprising natural or non-natural D- or L-amino acids.

Haptens, other than the VPs described herein, can be conjugated to the hC, such as the HhC, along with the VP. As explained previously, the term "haptens" refers to molecules that are not good immunogens by themselves, but they become immunogenic when attached to another molecule, such as a larger molecule. A hapten can be a small organic molecule, a monosaccharide, disaccharide, oligosaccharide, lipid, nucleic acid, peptide, or polypeptide, for example. Although a hapten may be capable of binding to an antibody, immunization with a hapten does not usually provoke a strong antibody response. However, immunogenicity can be achieved when the hapten is covalently attached by linking or conjugating to a larger carrier molecule, such as a hapten-carrier conjugate that is greater than 5,000 Daltons.

Other haptens that can be conjugated to the hC include any agent that can elicit the production of antibodies that are useful for preventing or treating a viral infection, thereby alleviating or eliminating the symptoms of the viral disease. The haptens can also reduce the risk of a patient from developing a disease or disorder due to the viral infection. Examples of haptens in addition to VP include peptides, nucleic acids, lipids, lipopeptides, lipoproteins, carbohydrates, and small molecules. Examples of peptides that can be used as haptens include T-cell epitopes and VP B-cell epitopes. Peptides that can be used as haptens, including VPs, T-cell epitopes, and B-cell epitopes, include synthetically or recombinantly produced or native peptides or proteins comprising natural or non-natural D- or L-amino acids.

T-cell epitopes that can be used for activating a T-cell response (to provide T-cell help to B-cells) can be found in the extracellular proteins of *Clostridium botulinum, Clostridium perfringens*, and *Staphylococcus aureus*, and in the extracellular solute binding proteins of *Mycobacterium* and *Clostridium tetani*. T-cell epitopes are also present in *Mycobacterium tuberculosis, Mumps rubulavirus, Plasmodium falciparum*, Human immunodeficiency virus 1, Hepatitis C virus, and Influenza A virus. Examples of such T-cell epitopes include peptides comprising amino acid sequence SEQ ID NO: 32 or 33 (from the extracellular protein of *Clostridium botulinum*, GenBank: STC78113.1); SEQ ID NO: 34 (from the extracellular protein *Clostridium perfringens*, GenBank: SUY45886.1); SEQ ID NO: 35 (from the extracellular protein *Staphylococcus aureus*, GenBank: SA003917.1); SEQ ID NO: 36, 37, 38, 39, or 40 (from the extracellular solute-binding protein of various species of *Mycobacterium*, NCBI Reference Sequence: WP_055398728.1); SEQ ID NO: 41, 42, or 43 (from the extracellular solute-binding protein *Clostridium tetani*, GenBank: CDI50554.1; SEQ ID NO: 44 (from the ESAT-6-like protein EsxB of *Mycobacterium tuberculosis*); SEQ ID NO: 45 (from Alpha-crystallin protein of *Mycobacterium tuberculosis*); SEQ ID NO: 46 (from the mumps rubulavirus protein of Mumps rubulavirus); SEQ ID NO: 47 (from the DNAJ protein of *Plasmodium falciparum*); SEQ ID NO: 48 (from the Gag-Pol polyprotein of Human immunodeficiency virus 1); SEQ ID NO: 49 (from the Genome polyprotein of Hepatitis C virus); SEQ ID NO: 50 (from the Matrix protein 1 of Influenza A virus); and SEQ ID NO: 51 (from Hemagglutinin of Influenza A virus).

Lipids that can be attached to the hC include those that induce an innate immune response through binding to Toll-like receptors (TLR). The lipids can also serve as adjuvanting agents. Examples of such lipids include monophosphoryl lipid-A, squalene, lipopolysaccharides (LPS), lipoproteins, or lipopeptides. Carbohydrates that can serve as haptens include glucose, disaccharides, trisaccharides, and larger saccharides, including complex carbohydrates.

Examples of peptides that bind TLR, which can be used haptens, include TLR ligands, such as the TLR-4 agonist.

These peptides act as adjuvant peptides. In embodiments, the adjuvant peptide comprises the amino acid sequence APPHALS (SEQ ID NO: 52).

Other molecules can also include haptens, for example, B-cell epitopes. B-cell epitopes that can be used as haptens include those on any peptide that an immune response is desired. Also, additional VPs of the same target as the peptide immunogen can be added as other molecules. As used herein, the same target refers to treating and preventing the disease or infection caused by the same virus When haptens are small peptides, the entire peptide can be used as a hapten. When the hapten is a protein, a portion can be used as a hapten. Portions of a protein to use as a hapten can be determined using in silico prediction algorithms or peptide-based epitope mapping of the entire protein, which are well-known methods. Many T-cell and B-cell epitopes have been determined using these methods.

Haptens that can enhance the immunogenicity of the VP or enhance the duration or breadth of the immune response of the VP can be conjugated to the hC along with the VP. For example, a hapten that functions to bind a TLR can comprise an adjuvant function and enhance the immunogenicity of the VP. In embodiments, the VP-HhC conjugate can include other haptens or peptides in addition to one or more different or the same VPs.

One or more residues can be added to the N- or C-terminus of the haptens described herein to increase the stability of the peptides in vivo. For example, V (valine), M (methionine), G (glycine), I (isoleucine), D (aspartic acid), or P (proline) or a combination of these residues can be added to the N- or C-terminus of the peptides.

The present disclosure describes VP immunogen which includes VP-hC conjugates and VPhC oligomers. These conjugates and oligomers can also include other molecules. Peptides used for making the VP immunogen include monomeric peptides, the VP, other molecules including T-cell epitopes, haptens, and adjuvanting peptides, described herein. They can be chemically synthesized by manual techniques or by automated procedures. As an example, solid-phase polypeptide synthesis (SPPS) has been performed since the early 1960s. Over the years, improvements to the early SPPS have been made, and many methods have been automated.

Peptides including peptides for generating the hC, VP, and other haptens, described herein can be chemically synthesized by manual techniques or by automated procedures. As an example, solid-phase polypeptide synthesis (SPPS) has been performed since the early 1960s. Over the years, improvements to the early SPPS have been made, and many methods have been automated. Chemistries have been developed to protect terminal ends and other reactive groups. The terminal ends of the peptides described herein can be protected with acetyl, benzyloxycarbonyl, biotin, cinnamic acid, FMOC, tBOC, formyl, or N-methyl groups for example at the N-terminus and/or an amide group at the C-terminus. Linker such as proteolytic cleavage sites, spacers, and/or haptens such as T-cell epitopes, can be added to the monomeric peptide prior to the addition of the protecting groups.

Peptides, in particular, the longer peptides described herein can be generated by native chemical ligation (NCL). Using NCL, a large peptide (polypeptide) can be formed by ligating (or coupling) two or more smaller peptides. In embodiments, a polypeptide including a monomeric peptide and two or more haptens can be prepared from two or more smaller peptide fragments and assembled together using NCL technology. As an example, a polypeptide including a monomeric peptide and two haptens (one at each N- and C-terminus of the monomeric peptide) can be synthesized from two smaller peptides, which are covalently attached by NCL. Using NCL, a C (cysteine) is added to the N-terminus of one of the two smaller peptides, and a thioester functional group is added to the C-terminus of the other of the two smaller peptides, and these two peptides are subsequently ligated into the full-length polypeptide. In embodiments, residues are added to peptides described herein for ease of synthesis of longer polypeptides.

In embodiments, spacers can also be added between the monomeric peptide and VP or the one or more other haptens during synthesis. Examples of one or more residues that can be inserted as spacers include G (glycine), D (aspartic acid), S (serine), C (cysteine), or a combination thereof. In embodiments, spacers also include D, GD, or GSG.

The peptides and haptens described herein can also be produced biologically or recombinantly in a heterologous expression system. Any heterologous expression system can be used for producing the peptides described herein. In embodiments, the expression system comprises *E. coli.*, which lacks the machinery for post-translational modification, making it a suitable host for producing the peptides described herein.

Other molecules including the VP can be attached to the hC using any known method including click chemistry or homo- or heterobifunctional cross-linking reagent or peptide bond formation. In embodiments, haptens can be conjugated to the hC using EDC (1-ethyl-3-(3-dimethylaminopropyl) carbodiimide hydrochloride)/NHS (N-hydroxysuccinimide) or NHS/maleimide cross-linking chemistry, which is routinely used for conjugation reactions. The y residues, for example, lysines, are positioned to provide well-defined hapten placement and coupling stoichiometry.

Other molecules including the VP can also be attached to the hC via any suitable linker moiety. Examples of linkers include those that form amide linkages, ester linkages, and disulfide linkages. The linker can be a cleavable linker such as protease cleavable peptide linker, nuclease sensitive nucleic acid linker, lipase sensitive lipid linker, glycosidase sensitive carbohydrate linker, pH-sensitive linker, hypoxia sensitive linker, photo-cleavable linker, heat-labile linker, or enzyme cleavable linker, such as a proteolytic cleavage site. As an example, proteolytic cleavage sites can comprise amino acid sequence YR. The linker can also be noncleavable. Any known method can be used to associate a linker with the hC, for example, click chemistry, passive adsorption, multivalent chelation, high-affinity non-covalent binding, or covalent bond formation. A hapten can also be attached to the hC without a linker.

Additionally, other molecules including the VP can be conjugated to the hC through another molecule. For example, the VP or another B-cell or T-cell epitope can be first attached to a carrier for displaying an epitope of interest, and then be conjugated to the HhC. Examples of such a carrier include protein, peptide, nanoparticle, virus-like particle, or anything that can function as a carrier for displaying VPs or other epitopes of interest.

Furthermore, the present disclosure describes a VP-hC conjugate or VPhC oligomer optionally including one or more one or more other molecules, such as those described herein. The one or more other molecules include immunomodulators and/or haptens. In embodiments, the one or more other molecules include T-cell epitopes, B-cell epitopes, short peptides for example VP peptides, or a combination thereof. In embodiments, the one or more other molecules are linked to the N- and/or C-terminus of one or more of the helices in the core of the hC. In embodiments, the one or more other molecules are linked to the N-terminus of the one or more helices of the core of the hC. In embodiments, one or more molecules are linked to the C-terminus of the one or more helices of the core of the hC.

In embodiments, the T-cell epitopes at the N- and/or C-terminus of one or more of the helices in the core of the hC recruit T helper cells and induce B cells to produce maximum IgG titers for providing a robust immune response, as well as to promote affinity maturation and class switching. Methods for selecting a T-cell epitope peptide are well-known. For example, a T-cell epitope can be selected by experimental methods known in the art, identified from the scientific literature, predicted using bioinformatics tools, designed de novo, or a combination of these methods. In embodiments, the T-cell epitopes at the N-terminus and C-terminus are the same or different. In embodiments, the T-cell epitopes are, for example, CD4+ T-cell epitopes, which are known to enhance the development of memory B cells and plasma cells that produce high-affinity antibodies. In embodiments, T-cell epitopes that can be included in the N- and/or C-terminus of the one or more helices of the hC include TCE1, TCE2, TCE3, TCE4, TCE5, or a combination thereof. As examples, the T-cell epitopes comprise amino acid sequence SEQ ID NO: 44, 45, 46, 47, 48, 49, 50, 51, 105, 106, 107, or 108. In embodiments, T-cell epitopes comprising an amino acid sequence SEQ ID NO: 105 or 106 are attached to the N-terminus, and T-cell epitopes comprising an amino acid sequence SEQ ID NO: 107 or 108 are attached to the C-terminus. One or more of these T-cell epitopes can be attached to the hC or the VP.

One or more T-cell epitopes and/or B-cell epitopes can also be linked to the VP prior to conjugating to the hC. Again, these epitopes are used to recruit T helper cells and induce B-cells to produce maximum IgG titers, as well as to promote affinity maturation and class switching.

When a hapten or immunomodulator, such as T-cell and B-cell epitopes, is linked to the VP for conjugation to the hC or to the N- and/or C-terminus of monomeric peptide, one or more spacers can be inserted between the hapten and the VP or between the hapten and the monomeric peptide. Spacers are added for immunomodulators, such as T-cell epitopes, for the correct processing of the T-cell epitopes to ensure proteolytic trimming that results in a size that fits into the MHC II binding cleft. Examples of such spacers include residues D (aspartic acid), G (glycine), P (proline), S (serine), or a combination thereof. In embodiments, the spacers include one or more of D, GD, PGP, GSG, GPGP (SEQ ID NO: 109), GPGPG (SEQ ID NO: 104), GPGPGC (SEQ ID NO: 110), SGPGPG (SEQ ID NO: 111), or HAA. In embodiments, the spacer for the correct processing of the T-cell epitopes includes GPGPG (SEQ ID NO: 104).

Haptens or immunomodulators described herein that are small peptides can be linked at the N- and/or C-terminus of one or more helices of the core of the hC. They can be incorporated into the monomeric peptide, such that they are covalently attached to the N- and/or C-terminus of the monomeric peptide using solid-phase synthesis or native chemical ligation (NCL). The haptens can be covalently attached to the N- and/or C terminus using homo or heterobifunctional cross-linkers or using click chemistry reagents, which are well-known reagents for coupling molecules. In embodiments, the immunomodulators or haptens, for examples the T-cell epitopes and/or B-cell epitopes, are already attached to the N- and/or C-terminus prior to self-assembly into the hC core, such as the HhC core, and the VP can be conjugated after the self-assembly into the hC core.

The haptens or immunomodulators at the N- and/or C-terminus can also be linked or conjugated to the hC through either an intermediary functional reagent such as a reactive small molecule or a large molecule. Examples of such small molecules include a catalyst, a stable intermediate, or a salt. Examples of such large molecules include a multiple antigenic peptide, protein, or enzyme.

Further, the conjugation of haptens including the VP and/or other molecules to the core of the hC can be performed using any kind of linkers. The linkers can be cleavable or uncleavable. Cleavable linkers include protease cleavable peptide linkers, nuclease sensitive nucleic acid linkers, lipase sensitive lipid linkers, glycosidase sensitive carbohydrate linkers, pH-sensitive linkers, enzyme cleavable linkers, heat-labile linkers, photo-cleavable linker. Cross-linkers can also be used by activation of a side chain atom or terminal atom for covalent reaction with an intermediary or final molecule atom to form a covalent bond.

The present disclosure describes scaffold peptides (hapten carriers (hCs) including a hC monomeric peptide and one or more haptens and/or immunomodulators, such as one or more T-cell epitopes and/or VP, linked to its N- or C-terminus. As described herein, the scaffold peptides can also include one or more spacers, for example, one or more residues for the correct processing of T-cell epitopes or stabilizing the hapten and/or the hC monomeric peptide. Table 1 discloses exemplary scaffold peptides.

TABLE 1

Scaffold Peptides

| Name of Scaffold Peptide | Sequence* |
|---|---|
| Mouse Scaffold Peptide | VASNENMETMGPGPGDIRSIGKEIRSIGRE IRSIGKEIRSIGREGPGPGFQDAYNA AGGHNAVE (SEQ ID NO: 112) |
| Human Scaffold Peptide | VQYIRANSRFIGITEHAADIRSIGKEIR SIGREIRSIGKEIRSIGREYRRLNELLA YV (SEQ ID NO: 113) |

*The amino acid sequences for the T-cell epitopes are underlined. The linker/proteolytic cleavage sites are bolded. The monomeric peptide is double underlined (SEQ ID NO: 30). Valine (V) is added to the N-terminus of the T-epitopes for stability, and D (italicized) is added to the N-terminus of the monomeric peptide as a spacer.

The mouse scaffold peptide (hC) includes a T-cell epitope (SEQ ID NO: 105) at the N-terminus, a hC monomeric peptide (SEQ ID NO: 30), and another T-cell epitope (SEQ ID NO: 107) at the C-terminus. It also includes the stabilizing residues valine (V) and linkers (SEQ ID NO: 104) inserted between the T-cell epitopes and the hC monomeric peptide. The residue D is added as a spacer. In this example, the T-cell epitopes are attached to the hC monomeric peptide prior to self-assembly into a hexameric core for attaching VPs. The linkers (SEQ ID NO: 104) are added to augment correct T-cell epitope processing.

The human scaffold peptide includes a T-cell epitope (SEQ ID NO: 106) at the N-terminus, a hC monomeric peptide (SEQ ID NO: 30), and another T-cell epitope (SEQ ID NO: 108) at the C-terminus. It also includes one or more stabilizing residues valine (V) and aspartic acid (D) and linkers/proteolytic cleavage sites (HAA and YR) inserted between the T-cell epitopes and the hC monomeric peptide. The linker (HAA) is added to augment correct T-cell epitope processing, and the linker (YR) is a proteolytic cleavage site.

In this example, the T-cell epitopes are attached to the hC monomeric peptide prior to self-assembly into a hexameric core for attaching VPs. The human scaffold peptide (hC) can be used not only in human subjects but in other mammalian subjects including mice and rabbits.

These scaffold peptides can be protected at the N-terminus and/or C-terminus with protecting groups to prevent proteolytic degradation of the peptides. As an example, an acetyl group can be added to the N-terminus, and an amino group can be added to the C-terminus.

The exemplary scaffold peptides shown in Table 1 self-assemble to form hexameric (Hex) core or hexameric (Hex) scaffold.

The present disclosure also describes peptide immunogens comprising VPs, for conjugating to the hC to form VP-hC conjugates for the preparation of vaccines. As described herein, the peptide immunogens can also include one or more other residues for stabilizing the VP or for the correct processing of T-cell epitopes. The peptide immunogen can be based on the peptide from the virus, for example, the wild-type peptide sequence. However, the wild-type peptide sequence can also be modified to make the peptide more useful or more easily used as a peptide immunogen. Table 2 discloses exemplary peptide immunogens for conjugating or attaching to the hC.

TABLE 2

Peptide Immunogens (containing stabilizing residues)

| Name of Immunogen* | Sequence* |
|---|---|
| S1 | VSFIEDLLFNKVTLADAGFDDEDC (SEQ ID NO: 73) |
| S2 | VSYQTQTNSPRRARSVASQSIIDDEDC (SEQ ID NO: 57) |
| S3 | VFSQILPDPSKPSKRSFIEDDEDC (SEQ ID NO: 69) |
| S4 | VNGVEGFNSYFPLQSYGFQPTNGVGYQDDEDC (SEQ ID NO: 115) |
| S5 | VNYNYLYRLFRKSNLKPFERDISTEIYQAGSTP DDEDC (SEQ ID NO: 55) |
| S6 | VSVLYNSASFSTFKSYGVSPTKLNDLSFTNDDEDC (SEQ ID NO: 54) |
| M1 | VMADSNGTITVEELKKLLEQWNLVIDDEDC (SEQ ID NO: 67) |

*The peptide sequence of the respective peptide immunogen is underlined. The bolded residues are added to the peptide sequence as a linker or spacer for coupling purposes or to stabilize the peptide. The bolded and underlined residues are substituted residues.

As an example, peptide immunogens S4 and S6 have been modified by substituting the C (cysteine) in the wild-type peptide with an S (serine) because the C can interfere with conjugation to the hC.

The peptide immunogens described herein can optionally include one or more additional haptens, for example, one or more immunomodulators, such as a T-cell epitope.

These peptide immunogens can also be protected at the N-terminus and/or C-terminus with protecting groups to prevent proteolytic degradation of the peptides. As an example, an acetyl group can be added to the N-terminus, and an amide group can be added to the C-terminus.

Additionally, the present disclosure describes VP-hC conjugates. Exemplary VP-hC conjugates include: S1 peptide+scaffold peptide (S1 peptide immunogen conjugated to a hexameric scaffold (H) comprising the scaffold peptide shown in Table 1); S2 peptide+scaffold; S3 peptide+scaffold; S3 peptide+scaffold; S4 peptide+scaffold; S5 peptide+scaffold; S6 peptide+scaffold; and M1 peptide+scaffold.

In embodiments, the monomeric peptides described herein can also be used as immunogens when a peptide immunogen from a virus, such as S1, S2, S3, S4, S5, S6, or M1, is attached to (incorporated into) the scaffold peptide. One or more peptide immunogens can be inserted during the synthesis of the scaffold peptide so that the final peptide includes both the scaffold peptide and one or more peptide immunogen. The final peptide can also self-assemble into an oligomer, such as a hexamer. Examples of a scaffold containing a VP immunogen (VPHhC) include: S1HexhC, wherein S1 is the peptide immunogen and HexhC is the hexameric core; S2HexhC; S3HexhC; S4HexhC, S5HexhC, S6HexhC, and M1HexhC. Short peptides and residues as described herein can be added to create stability. Optionally, additional haptens can be conjugated to the oligomer core of these scaffold peptides.

The VP-hC conjugates and the VPhC oligomers described herein are used to prepare compositions, such as pharmaceutical compositions. Pharmaceutical compositions including one or more VP-hC conjugates and one or more VPhC oligomers can be used as therapeutics or vaccines or vaccine or therapeutic compositions. The pharmaceutical compositions described herein are also immunogenic compositions comprising immunomodulators, as they enhance the immunogenicity of VP. The pharmaceutical compositions described herein are also therapeutic compositions, as they can be used to treat patients in need thereof.

The present disclosure describes compositions including the VP-hC conjugates and the VPhC oligomers described herein and one or more excipients. In embodiments, the hC is conjugated to one or more VPs and optionally includes other haptens, such as one or more T-cell epitopes at the one or more N- and/or C termini of the amphipathic helices of the core of the hC. In embodiments, the composition is a pharmaceutical composition and the excipient is a pharmaceutically acceptable excipient. In embodiments, the hC is HhC (hexameric hapten carrier).

The term "excipient" refers to a diluent, adjuvant, or vehicle with which the hC is administered. Examples of adjuvants include complete and incomplete Freund's adjuvant, which are used with animals, particularly research animals. Pharmaceutically acceptable excipients can be sterile liquids, such as water and oils, including those of petroleum, animal, vegetable, or from synthetic origins, such as peanut oil, soybean oil, mineral oil, sesame oil, and the like. Water is a preferred excipient when the pharmaceutical composition is administered intravenously. Saline solutions and aqueous dextrose and glycerol solutions can also be employed as liquid excipients, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Pharmaceutically acceptable adjuvants include those that are based on monophosphoryl lipid-A (MPL A) mixed with oil, for example, squalene, to form a stable emulsion.

The composition or pharmaceutical composition, if desired, can also contain minor amounts of wetting or emulsifying agents, or pH buffering agents. These compositions can take the form of solutions, suspensions, emulsion, tablets, pills, capsules, powders, sustained-release formulations, and the like. Oral formulation can include standard excipients such as pharmaceutical grades of mannitol, lactose, starch, magnesium stearate, sodium saccharine, cellulose, magnesium carbonate, etc. Such formulation will contain a therapeutically effective amount of the hC, in purified form, together with a suitable amount of excipient to provide the form for proper administration to the subject. The formulation should suit the mode of administration.

The administration of the pharmaceutical compositions described herein may be carried out in any convenient manner, including by aerosol inhalation, injection, ingestion, transfusion, implantation, or transplantation. The compositions described herein also can be administered to a subject orally, topically, intranasally, enterally, rectally, buccally, vaginally, sublingually, subcutaneously, intradermally, intratumorally, intranodally, intramedullary, intramuscularly, intravenously, intracranially, intraperitoneally, or a combination thereof. The administration of the pharmaceutical composition can be in any manner that is effective to deliver a therapeutically and/or prophylactically effective amount of the conjugate described herein to the subject in need thereof.

The compositions described herein include immunogenic compositions. In embodiments, the compositions herein are therapeutics or vaccines. The present disclosure describes a method of preparing a vaccine which includes designing and preparing a monomeric peptide for the core of the hC described herein, allowing the monomeric peptide to oligomerize, and conjugating one or more VPs to the oligomerized hC to obtain a VP-hC conjugate. In embodiments, the hC is a hexameric hC (Hhc). The one or more VPs can be the same or different. Additionally, the present disclosure describes a method of preparing a vaccine or therapeutic which includes designing and preparing a monomeric peptide for the core of the hC described herein, covalently attaching a VP, to the monomeric peptide, and allowing the monomeric peptide to oligomerize to obtain a VPHhC oligomer, such as S1HhC oligomer. As described above, the monomeric peptide can be synthesized by SPPS which includes providing the prepared monomeric peptide in lyophilized form. Hydration of the lyophilized monomeric peptide allows oligomerization to take place. PBS, which includes salt and buffering capability, can be used to hydrate the lyophilized monomeric peptide. In embodiments, the oligomerized hC is a HhC.

The methods described herein include increasing the immunogenicity of the VP. The methods include conjugating one or more VPs to the hC described herein. The method can further include synthesizing a monomeric peptide with one or more other haptens or immunomodulators, for example, T-cell or B-cell epitopes at the N- and/or C-terminus of the one or more helices of the core of hC. In embodiments, the monomeric peptide is synthesized with a T-cell and/or B-cell epitope present at the N- and/or C-terminus. The increase in immunogenicity of VP is compared with the immunogenicity of VP by itself, for example, not linked to or associated with the hC or an excipient. Additionally, the methods described herein also include conjugating one or more other haptens or immunomodulators to increase the immunogenicity of VP. Examples of such haptens and immunomodulators include small molecules, lipids, lipoproteins, and TLR-4 agonists.

In embodiments, the present disclosure describes immunogenic compositions comprising the VP-hC conjugate as described above. The VP-hC conjugate optionally includes one or more T-cell and/or B-cell epitopes and/or one or more additional haptens, other than the VP. In embodiments, the hC is a HhC. The immunogenic composition includes one or more pharmaceutically acceptable excipients. The excipient can be an adjuvant that is used to improve or enhance the immune response to the VP-hC conjugate in a therapeutically effective manner. The immunogenic composition can be administered to a subject in need thereof by any route described herein for delivering a VP vaccine in an effective amount to a subject in need thereof.

The dosage for administering the pharmaceutical and immunogenic compositions described herein to a subject will vary with the precise nature of the condition being treated and the recipient of the treatment. The scaling of dosages for human administration can be performed according to art-accepted practices by a physician depending on various factors.

The pharmaceutical or immunogenic composition described herein can be a formulation. In embodiments, the pharmaceutical or immunogenic composition can be formulated for immediate release or sustained or slow release. Such formulations can be prepared using well-known technology. Sustained release formulations can contain the conjugates described herein conjugate dispersed in an excipient matrix and/or contained within a reservoir surrounded by a rate controlling membrane. Excipients for use within such formulations are biocompatible and/or biodegradable. The formulation provides a relatively constant level of active component release. The amount of conjugate contained within a sustained release formulation depends upon the site of implantation, the rate and expected duration of release, and the nature of the condition to be treated or prevented.

The present disclosure also describes kits with unit doses of conjugates described herein. Such kits may include a container containing the unit dose, an informational package insert with instructions for using the kit to treat or prevent a disease or disorder of interest, and optionally an appliance or device for delivery of the composition.

Additionally, the present disclosure describes a method of enhancing the immunogenicity of a VP. In embodiments, the method includes obtaining a monomeric peptide described herein, allowing the monomeric peptide to self-assemble into an oligomer (a hC), such as a hexamer, and conjugating the hapten, such as the VP, to the oligomer (hexamer hC) to obtain a hapten-hC, such as VP-HhC. Immunomodulators can also be conjugated to the oligomer. In embodiments, the method also includes synthesizing a monomer peptide (MP) to contain a VP peptide on the N- and/or C-terminus, and allowing the VPMP (VPMP) to self-assemble into an oligomer, such as a hexamer, to obtain a VPhC oligomer, such as the VPHhC oligomer. As described herein, the VP-hC conjugate or VPhC oligomer can include one or more additional haptens or immunomodulators such as one or more T-cell epitopes, or B-cell epitopes. As described herein, VP-hC conjugate or VPhC oligomer can further include one or more residues for stabilizing the hapten, one or more residues for proper processing of the T-cell epitopes, and/or one or more spacers inserted between the hapten and the monomeric peptide. The methods described herein can be used to prepare vaccines or therapeutics or compositions comprising vaccine or therapeutic, such as a VP immunogenic therapeutic composition, for administering to subjects in need thereof to prevent or treat the subject.

The present disclosure also describes the use of the conjugates, oligomers, pharmaceutical compositions, therapeutics, therapeutic compositions, and vaccines described herein to treat subjects in need thereof. Similar to the compositions, the vaccines comprise the conjugates or the oligomers described herein. The present disclosure also describes methods for treatment of subjects in need thereof.

The methods described herein include treating subjects such as humans, veterinary animals (dogs, cats, reptiles, birds, etc.), livestock (horses, cattle, goats, pigs, chickens, etc.), and research animals (monkeys, rats, mice, fish, etc.). Subjects in need of treatment (in need thereof) are subjects having disease or disorders that need to be treated with a VP vaccine or immunogenic composition that will induce an immune response in the subject that is sufficient or therapeutically effective to prevent or treat a subject of a disease or disorder. A subject in need thereof can also be a subject susceptible to or at risk of developing a viral disease or infection. The subject in need thereof can also be an individual infected with a virus that causes a viral disease or infection. The viral disease or infection can be a mild, severe, or fatal form of the viral disease or infection.

As an example, the antibodies induced by vaccination with the VP-hC conjugates or VPhC oligomers described herein can neutralize and prevent or treat a viral disease or infection. The immune response generated by the VP-hC conjugate or VPhC oligomer is sufficient to prevent or treat a viral disease or infection. In embodiments, methods described herein can be used to prevent a subject from developing a viral disease or treat a subject infected with a virus.

Preventing as used herein refers to preventing or reducing the risk of a subject in need thereof from developing a viral disease or infection. Prevention includes inhibiting, reducing, or attenuating the function of the virus, for example, weakening the virus making it difficult for the virus to fuse with the membrane of a host (subject's) cell and gain entry. In embodiments, the VP-hC conjugates or VPhC oligomers described herein induce an immune response in the subject to generate antibodies that reduce the capabilities of the virus to gain entry into the host cell. The antibodies remain in the subject and inhibit, reduce, attenuate the development of new virus or viral particles. In embodiments, the VP-hC conjugates or VP-hC oligomers are administered to the subject prior to infection to prevent the subject from developing the disease. In embodiments, the VP-hC conjugates or VPhC oligomers are administered to the subject described herein are administered after the infection to prevent the subject from developing a serious viral disease or infection.

Treating a subject in need thereof as used herein includes alleviating the symptoms that a viral disease or infection would usually cause in a subject if the subject were not administered the VP vaccine before or after the infection. In embodiments, the VP-hC conjugates or VPhC oligomers described herein induce an immune response in the subject to generate antibodies that neutralize the virus and alleviate the symptoms of a viral disease or infection, such that the subject does not experience a mild, severe, or fatal viral disease or infection. In embodiments, the VP-hC conjugates or VPhC oligomers can be administered after the infection as a treatment to inhibit, reduce, or attenuate the function of the virus to alleviate symptoms of a viral disease or infection.

The methods described herein also include prophylactic treatment of a subject need thereof. The methods described herein include protecting a subject from a viral disease by inducing an immune response in the subject that is sufficient or therapeutically effective to protect the subject from the viral disease or alleviate the symptoms of the viral disease.

The methods of preventions and treatments described herein include administering an effective amount of the conjugate described herein or the composition including the conjugate described in an effective amount. An "effective amount" is the amount of active agent, for example, the conjugate or composition described herein, necessary to result in a desired physiological change in vivo or in vitro. A therapeutically effective amount includes those that provide an effective amount.

An efficacious vaccine contains components able to induce both innate and adaptive immune responses following immunization. Whereas innate immunity is induced using adjuvants, in embodiments, the vaccine described herein is VP-hC conjugate or VPhC oligomer that contains the adaptive B- and T-cell epitopes. The VP-hC conjugate contains minimal extraneous sequences for a more focused and robust immune response against the VP B-cell epitopes. In embodiments, for CD4+ and CD8+ T-cell activation, the N- and C-termini of each of the six helices and/or the core of the HhC contain species-specific CD4+ and CD8+ T-cell epitopes required as part of the adaptive immune system for developing pathogen-specific memory for immune protection, recruiting T-cell help, producing long-lived plasma cells and high titer/high affinity antibodies, and directing robust and long-lasting protective memory. These epitopes are placed at the termini of the HhC so that they do not interfere with hapten coupling. They are chosen to lack lysine and cysteine residues so that they are not haptenized or uncontrollably cross-linked during the B-cell epitope coupling process. It has been shown that lysine haptenization in T-cell epitopes greatly reduces their activity and function. T-cell epitopes from many different species can be acquired from the IEDB database and are chosen based on positive T- and B-cell assays including MHC ligand binding assays, ability to recruit T-cell help, and induction of B-cell proliferation. The modular nature of the vaccine technology described herein simplifies transferring vaccine constructs between species, as it is a simple matter of replacing the T-cell epitopes and modifying the B-cell epitope if a different disease or condition is targeted.

Similar to the VP-hC conjugate, the VPhC oligomer contains minimal extraneous sequences for a more focused and robust immune response against the VP B-cell epitopes. The VPhC oligomer can include T- and/or B-cell epitopes, as these epitopes can be attached to the hC, the oligomeric core by covalent coupling.

A distinct advantage of the HhC core region described herein is its reduced immunogenicity, which minimizes the presentation of unproductive or non-protective immunodominant epitopes. Thus, the combination of presenting multiple VP B-cell epitopes with a reduction of non-productive immunodominant epitopes, and the presentation of multiple T-cell epitopes, produces a highly efficacious vaccine.

The advantages of using a completely synthetic VP-hC conjugate or VPhC oligomer vaccine are numerous. Modern SPPS routinely produces peptides up to 70-75 residues in length. The HhC described herein will range in size from 55 to 65 residues with the length of the T-cell epitopes defining how much longer than the 28-30 residue core region the HhC will be. The VP can contain extra amino acids for spacing or imparting unique chemistry, making total synthetic construction of the vaccine feasible. Producing kilogram quantities of vaccine peptides in cGMP facilities eliminates costly, time-consuming, and resource-intensive industrial production and purification of recombinant proteins and there is no need for subsequent viral clearance, endotoxin removal, or testing for the presence of infectious agents. It is usually perceived that peptide synthesis is too costly for large-scale vaccine manufacturing. However, if high nanogram to low μg doses can be used, peptide vaccines are several-fold more cost-effective than VP conjugated to recombinant subunit vaccines.

The terms "residue" and "amino acid" are used interchangeably throughout the disclosure to refer to "amino acid."

As will be understood by one of ordinary skill in the art, each embodiment disclosed herein can comprise, consist essentially of, or consist of its particularly stated element, step, ingredient, or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment. In embodiments, those that do not materially affect the embodiment are those elements, steps, ingredients, or components that do not reduce the embodiment's ability in a statistically significant manner to perform a function in vitro or in vivo, such as providing immunity to a disease or generating an immune response. In embodiments, the components of the conjugates and oligomers described herein, such as VP, hC, or T-cell epitopes, can consist essentially of or can consist of a specific sequence. In embodiments, the vaccine or vaccine composition can consist essentially of or can consist of a VP-hC conjugate or VPhC oligomer and an excipient.

In addition, unless otherwise indicated, numbers expressing quantities of ingredients, constituents, reaction conditions, and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±15% of the stated value; ±10% of the stated value; ±5% of the stated value; ±4% of the stated value; ±3% of the stated value; ±2% of the stated value; ±1% of the stated value; or ±any percentage between 1% and 20% of the stated value.

The terms "a," "an," "the" and similar referents used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The following exemplary embodiments and examples are provided herein. These exemplary embodiments and examples are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

EXEMPLARY EMBODIMENTS

1. A viral peptide (VP) conjugate (VP-hC) or a VP oligomer (VPhC) including one or more viral peptides (VPs) covalently attached to a hapten carrier (hC), the hC including an oligomer which includes a monomeric peptide comprising the following amino acid sequence:

$$(hwxhxyz)n,$$
(SEQ ID NO: 2)

wherein h is a hydrophobic or non-polar residue;

w is a positively charged, negatively charged, polar uncharged, or non-polar aliphatic residue;

x is a negatively charged, positively charged, non-polar aliphatic, or polar uncharged residue;

y is a residue for epitope coupling;

z is a negatively charged, positively charged, polar uncharged, or non-polar aliphatic residue; and n is an integer greater than 1; and wherein the VP conjugate includes one or more VPs conjugated to the hC; and wherein the VP oligomer includes one or more VP incorporated into the hC.

2. The VP conjugate or VP oligomer of embodiment 1, wherein the monomeric peptide includes amino acid sequence SEQ ID NO: 2, wherein h is I, L, V, F, W, Y, M, G, or A;

w is G, R, A, N, Q, H, S, D, E, K, or T;

x is R, S, N, Q, A, G, T, D, E, K, H, or C;

y is K, H, C, D, E, R, W, Y, Q, N, or a non-natural amino acid or molecule containing reactive groups amenable to covalent coupling;

z is A, D, H, S, E, R, N, Q, K, or G; and n is 2 to 10.

3. The VP conjugate or VP oligomer of embodiment 1 or 2, wherein the monomeric peptide includes the amino acid sequence SEQ ID NO: 3, 4, 5, 6, 7, 8, 9, 10, 11, 12, 13, 14, 15, 16, 17, or 18.

4. The VP conjugate or VP oligomer of any one of embodiments 1-3, wherein the monomeric peptide includes the amino acid sequence SEQ ID NO: 19, 20, 21, 22, 23, 24, 25, 26, 27, 28, 29, 30, or 31.

5. The VP conjugate or VP oligomer of any one of embodiments 1-4, wherein the monomeric peptide further includes residue V, M, G, I, D, P, C, S, C, or a combination thereof at the N-terminus and/or C-terminus.

6. The VP conjugate or VP oligomer of any one of embodiments 1-5, wherein the oligomer is a dimer, trimer, tetramer, pentamer, hexamer, heptamer, octamer, nanomer, or decamer.

7. The VP conjugate or VP oligomer of any one of embodiments 1-6, wherein the oligomer is a hexamer.

8. The VP conjugate or VP oligomer of any one of embodiments 1-7, wherein the one or more VPs are obtained from a Coronavirus, an Influenza virus, a Respiratory Syncytial virus (RSV), Human Papillomavirus (HPV), Dengue virus, Yellow Fever virus (YFV), or West Nile virus (WNV).

9. The VP conjugate or VP oligomer of any one of embodiments 1-8, wherein the one or more VPs are obtained from a SARS-CoV-2 virus.

10. The VP conjugate or VP oligomer of any one of embodiments 1-9, wherein the one or more VPs include one or more S peptides of the spike glycoprotein and/or the membrane protein (M) of a SARS-CoV-2 virus.

11. The VP conjugate or VP oligomer of any one of embodiments 1-10, wherein the one or more VPs include S1, S2, S3, S4, S5, S6, and/or M1.

12. The VP conjugate or VP oligomer of any one of embodiments 1-11, wherein the one or more VPs include one or more of amino acid sequences SEQ ID NO: 136, 120, 132, 119, 118, 117, and/or 130.

13. The VP conjugate or VP oligomer of any one of embodiments 1-11, wherein the one or more VP includes one or more modified peptides.

14. The VP conjugate or VP oligomer of embodiment 13, wherein the modified peptide includes one or more cysteine (C) in the sequence is replaced with serine (S).

15. The VP conjugate or VP oligomer of embodiment 14, wherein the modified peptide includes amino acid SEQ ID NO: 139 or 140.

16. The conjugate of any one of embodiments 1-8, 13, or 14, wherein the one or more VPs include one or more amino acid sequences SEQ ID NO: 76, 77, 78, 79, 80, 81, 82, or 83 (Influenza A virus) SEQ ID NO: 74 or 75 (RSV); SEQ ID NO: 82, 93, 94, 95, or 96 (HPV); SEQ ID NO: 97, 98, 99, 100, 101, or 102 (Dengue virus); SEQ ID NO: 88, 89, 90, or 91 (YFV); or SEQ ID NO: 84, 85, 86, or 87 (WNV).

17. The VP conjugate or VP oligomer of any one of embodiments 1-16, wherein the one or more VPs include additional amino acids at its N- and/or C-terminus.

18. The VP conjugate or VP oligomer of embodiment 17, wherein the additional amino acid is V (valine) and/or DDEDC (SEQ ID NO: 116).

19. The VP conjugate or VP oligomer of any one of embodiments 1-18, wherein the one or more VPs include a protecting group at its N- and/or C-terminus.

20. The VP conjugate or VP oligomer of embodiment 19, wherein the protecting group includes an acetyl group and/or an amide group.

21. The VP conjugate or VP oligomer of any one of embodiments 1-20, wherein the VP conjugate or VP oligomer includes two or more VPs and/or wherein the VPs are obtained from different sources of viruses.

22. The VP conjugate or VP oligomer of embodiment 21, wherein the two or more VPS are from different strains of SARS-CoV-2.

23. The VP conjugate or VP oligomer of any one of embodiments 1-22, wherein the one or more VPs are conjugated to the hC through the y residue on the monomeric peptide.

24. The VP conjugate or VP oligomer of any one of embodiments 1-23, wherein the one or more VPs or the monomeric peptide further includes one or more immunomodulators or additional haptens.

25. The VP conjugate or VP oligomer of any one of embodiments 1-24, wherein the one or more immuno-modulators or additional haptens are covalently fused (incorporated to) the N- and/or C-terminus of the monomeric peptide or covalently attached at one or more N- and/or C-terminus of the oligomer's helices.

26. The VP conjugate or VP oligomer of any one of embodiments 1-25, wherein the VP conjugate or VP oligomer includes one or more spacers or linkers between the hapten or immunomodulator and the monomeric peptide.

27. The VP conjugate or VP oligomer of embodiment 26, wherein the one or more spacers or linkers include G (glycine), D (aspartic acid), S (serine), C (cysteine), or a combination thereof.

28. The VP conjugate or VP oligomer of embodiment 26 or 27, wherein the one or more spacers include D, GD, and/or GSG.

29. The VP conjugate or VP oligomer of any one of embodiments 1-28, wherein the one or more haptens or immunomodulators include one or more additional VPs, one or more T-cell epitopes, and/or one or more B-cell epitopes.

30. The VP conjugate or VP oligomer of embodiment 29, wherein the one or more T-cell epitopes include CD4+ T-cell epitopes.

31. The VP conjugate or VP oligomer of embodiment 29 or 30, wherein the one or more T-cell epitopes include amino acid sequence SEQ ID NO: 44, 45, 46, 47, 48, 49, 50, 51, 105, 106, 107, and/or 108.

32. The VP conjugate or VP oligomer of any one of embodiments 24-31, wherein the VP conjugate or VP oligomer further includes one or more residues for correct processing of the one or more T-cell epitopes.

33. The VP conjugate or VP oligomer of embodiment 27, wherein the one or more residues include D, G, P, or S, or a combination thereof.

34. The VP conjugate or VP oligomer of any one of embodiments 24-33, wherein the one or more immu-nomodulators or additional haptens enhance the immu-nogenicity of the one or more VPs or enhance the duration or breadth of the immune response of the one or more VPs.

35. The VP conjugate or VP oligomer of any one of embodiments of 24-34, wherein the one or more immu-nomodulators or additional haptens include a lipid, a peptide, a nucleic acid, or a combination thereof, and wherein the one or more immunomodulators or addi-tional haptens are conjugated to the hC or covalently attached or incorporated at the one or more N- and/or C-terminus of the oligomer's helices.

36. The VP conjugate VP oligomer of any one of embodi-ments 24-35, wherein the one or more immunomodu-lators or additional haptens include monophosphoryl lipid-A, squalene, lipopolysaccharides, lipoproteins, lipopeptides, or APPHALS (SEQ ID NO: 52).

37. The VP conjugate or VP oligomer of any one of embodiments 1-36, wherein the VP conjugate or VP oligomer includes an oligomer hC (scaffold) peptide including an amino acid sequence SEQ ID NO: 112 or 113.

38. The VP conjugate or VP oligomer of any one of embodiments 1-37, wherein the one or more VP include one or more amino acid sequences SEQ ID NO: 73, 57, 69, 115, 55, 54, and/or 67, optionally the one or more VP include SEQ ID NO: 73 (51), 55(S5), and/or 54 (S6).

39. A composition including the VP conjugate or VP oligomer of any one of embodiments 1-38 and an excipient.

40. The composition of embodiment 39, wherein the composition is a pharmaceutical composition and the excipient is a pharmaceutically acceptable excipient, and optionally, wherein the pharmaceutical composi-tion includes an adjuvant, such as MPL A.

41. A method of treating a subject having a viral disease or infection and/or preventing a subject from develop-ing a viral disease or infection, wherein the method includes administering to the subject, an effective amount of the VP conjugate or VP oligomer of any one of embodiments 1-38 or the composition of embodi-ment 39 or 40, wherein the VP induces an immune response in the subject, thereby treating the subject having the viral disease or infection or preventing the subject from developing a viral disease or infection.

42. The method of embodiment 41, wherein the subject is a mammal.

43. The method of embodiment 41 or 42, wherein the subject is a human.

44. The method of any one of embodiments 41-43, wherein the viral disease or infection is caused by SARS-CoV-2.

45. A method of enhancing the immunogenicity of a VP, wherein the method includes:
   obtaining a monomeric peptide of any one of embodi-ments 1-38;

allowing the monomeric peptide to self-assemble into a hC; and conjugating the VP of any one of embodiments 1-38 to the hC to obtain a VP-hC conjugate.

46. The method of embodiment 45, wherein the VP-hC conjugate is a VP hexamer (VP-HhC) conjugate.

47. A method of enhancing the immunogenicity of a VP, wherein the method includes:

synthesizing a VP monomeric peptide (VPMP), wherein the VPMP includes a monomeric peptide (MP) of any one of embodiments 1-38 and a VPpeptide of any one of embodiments 1-38; and allowing the VPMP to self-assemble into a VPhC oligomer.

48. The method of embodiment 47, wherein the VP oligomer is a VP hexameric oligomer (VPHhC).

49. A method of preparing a VP therapeutic or vaccine, wherein the method includes obtaining a monomeric peptide of any one of embodiments 1-38;

allowing the monomeric peptide to self-assemble into a hC; and conjugating the VP of any one of embodiments 1-38 to the hC to obtain a VP-hC conjugate, thereby obtaining a VP therapeutic or vaccine.

50. The method of embodiment 49, wherein the VP-hC conjugate is a VPHhC conjugate.

51. A method of preparing a VP therapeutic or vaccine, wherein the method includes:

synthesizing a VP monomeric peptide (VPMP), wherein the VPMP includes a monomeric peptide of any one of embodiments 1-38 and a VP of any one of embodiments 1-38; and allowing the VPMP to self-assemble into a VPhC oligomer, thereby obtaining a VP therapeutic or vaccine.

52. The method of embodiment 51, wherein the VPhC oligomer is a VP hexameric oligomer (VPHhC).

53. A peptide immunogen including the VP of any one of embodiments 1-38.

54. The peptide immunogen of embodiment 53, wherein the peptide immunogen includes the S1, S2, S3, S4, S5, or S6 of the S glycoprotein of SARS-CoV-2, and optionally, wherein the peptide immunogen includes 51, S5, or S6.

55. The peptide immunogen of embodiment 53 or 54, wherein the VP includes amino acid SEQ ID NO: 73, 57, 69, 115, 55, 54, or 67, and optionally wherein the peptide immunogen includes SEQ ID NO: 73 (51), 55 (S5), or 54 (S6).

56. The peptide immunogen of any one of embodiments 53-55, wherein the N-terminus and the C-terminus of the peptide immunogen include a protecting group, and optionally, wherein the protecting group of the N-terminus is an acetyl group and the protecting group of the C-terminus is an amide group.

57. A peptide scaffold (hC) of any one of embodiments 1-38.

58. The peptide scaffold of embodiment 57, wherein the peptide scaffold includes amino acid SEQ ID NO: 112 or 113.

59. The peptide scaffold of embodiment 57 or 58, wherein the N-terminus and the C-terminus of the hC include a protecting group, and optionally, wherein the protecting group of the N-terminus is an acetyl group and the protecting group of the C-terminus is an amide group.

60. A composition including one or more peptide immunogens of any one of embodiments 53-56 and at least one peptide scaffold of any one of embodiments 57-59.

61. The composition of embodiment 60, wherein the one or more peptide immunogen is attached to the at least one peptide scaffold of any one of embodiments 57-59.

62. The composition of embodiment 60, wherein the one or more peptide immunogens are not attached to the peptide scaffold.

EXAMPLES

Example 1. Constructing a VP Vaccine

There are up to 24 coupling sites on each hexameric carrier for hapten conjugation, but due to steric hindrance, it is unlikely that conjugation will occur on all sites. It has been previously shown that saturating the carrier with haptens does not always produce the most robust immune response and there is a trade-off between coupling density, epitope spatial/steric availability for correct B-cell epitope presentation, and antibody titer. Therefore, three separate hexamer conjugation reactions are performed to obtain conjugates with different epitope loading levels. For example, one reaction is performed with 3-5 molar equivalents of VPs so that only 3 or 4 peptides are conjugated, another reaction contains 8 to 10 molar equivalents to form a conjugate with 6-10 peptides, and the third reaction is performed using 25-50 molar equivalents to conjugate as many epitopes as possible (saturating conditions).

The VP is designed so the N-terminal residue is acetylated to protect the N-terminal amine from derivatization with cross-linkers. Residues (GEDC, SEQ ID NO: 53) can be added to modulate the pI of the VP.

Tryptophan fluorescence, gel filtration chromatography, native PAGE, and SELDI-TOF (a MALDI-like MS instrument ideally suited for determining the molecular weight of protein-peptide conjugates) were methods used to quantify peptide epitope coupling efficiency. It is relatively straightforward to calculate the number of VPs conjugated to the hexameric carrier and to BSA (VP-BSA is used as a coating reagent in ELISA assays). KLH was used as a positive immunization control because it is an antigenic "gold-standard" hapten carrier. However, it is so large it may only be possible to confirm successful conjugation without calculating the exact number of peptides conjugated.

Example 2. Characterizing VP-hC Constructs

Adjuvants: To enhance adaptive B- and T-cell responses, regulate the extent of protective immunity, and maximize VP-specific antibody responses, adjuvants were used for all immunizations. The best adjuvants directly stimulate dendritic cell maturation and the most effective way to guide this is through TLR-mediated activation. Synthetic TLR4-based adjuvants are some of the most effective, so at least two of these were tested. Monophosphoryl Lipid A (MPL) is a potent TLR4 agonist that can function as the primary adjuvant. MPL was emulsified with squalene (Sq) to form MPL-Sq. Emulsions efficiently prime CD4+ T-cells, which were important for inducing both memory and long-lived VP antibody responses. The adjuvants E6020 and GLA, which were approved for use in humans, were also tested. All adjuvants can assist with CD4+ induced VP-hC uptake into dendritic cells and induce VP-hC specific Th1 CD4+ T cells for binding T-cell epitopes. To assess adjuvant function, both CD4+ T cell and IgG isotype class switching was quantified in immunized mouse sera. Another important benefit of adjuvants is the high likelihood of antigen dose-sparing which is something that will also be tested. Dose-sparing can decrease the amount of VP-hC conjugate per immunization and increase the number of doses that can be obtained from a synthetic peptide batch and is a key determinant in reducing synthetic VP-hC conjugate manufacturing costs.

For each VP-hC conjugate, at least three sets of experiments were performed. Mice received a prime-boost immunization (IM) and B- and T-cell function was measured at several times post immunization. Three dose levels of VP-hC conjugates were compared to determine at which level maximum anti-VP IgG titers are obtained. The hexamer was maximally loaded with the VP and formulated with MPL-Sq adjuvant prior to immunization. Three dose levels (e.g. 0.1, 1, and 10 µg VP-hC) were tested and optimized depending on the anti-VP IgG titers. This experiment also tested anti-VP IgG specificity by measuring IgG response to the hC alone, VP alone, and the VP+hC (unconjugated but combined).

Mouse Immunizations with VP-hC: Inbred mice received a prime/boost immunization with adjuvanted VP-hC or control (VP-KLH conjugate). The first set of studies provided the optimal VP-hC dose and measures anti-VP IgG titer at each dose level. Sera were collected 14 days after both the prime and boost (d35) immunizations and antibody mid-point titers were measured. Mouse blood was used for performing B- and T-cell assays.

B-cell function: Standard ELISA was used to measure vaccine efficacy by VP-specific antibody titer in the collected mouse sera. ELISA plates are coated with VP-BSA conjugate and 8 sequential 10-fold dilutions (from 1:103 to 1:1010) of sera in blocking buffer were made and added to the ELISA plate wells. An HRP-labeled anti-mouse secondary antibody was added and the plates developed with a colorimetric substrate and measured in an ELISA plate reader. Data were plotted, curve fitted, and statistically analyzed using Prism Graph Pad software for calculating mid- and end-point titers.

T-cell function: T-cell epitope and adjuvant functions were measured by well-established T-cell ELISA assays. Commercially available coating reagents and primary/secondary antibodies were purchased and used according to the manufacturer's protocols. IFN-γ, IL-2, IL-4, and TNF-α are quantified in mouse sera as read-outs of T-cell function in VP-hC immunized mice. These targets could easily be expanded to include other markers of T-cell function including IL-5, IL-8, IL-10, IL-12p70, and IL-13. VP-hC induced T-cell dependent isotype class switching were assayed by ELISA using reagents specific for total IgG, IgG1, and IgG2a VP-hC safety: Initial assessments of safety were performed in a non-GLP setting to ensure mice have no adverse reactions to vaccine components (VP-hC, adjuvants). This initial evaluation provides some important read-outs to guide vaccine dose, adjuvant dose, and immunization schedules. Potential local and systemic toxicities were evaluated by observing injection site reactions and signs of inflammation as well as mouse behavior (e.g. signs of lethargy). If toxicity is observed, different adjuvant and/or T-cell epitopes are evaluated.

Example 3. Generating Vaccine for SARS-CoV-2

Antigenic Peptide Selection: Antigenic peptides for testing as vaccine candidates were selected based on a combination of several criteria. The first was based on the presence of the peptides of S-protein in the sera of convalescent SARS-CoV-2 patients infected with the virus but mounting a protective immune response. The second was based on in silico analysis of the three-dimensional structure of the SARS-CoV-2 S-protein with a focus on analyzing the S1 region of the holoprotein. Because the receptor binding domain of the S-protein is especially important for binding to human cells through the ACE2 receptor and entry into the host cell, special consideration was given to this region. Other functional regions tested include two proteolytic cleavage sites that are important for converting the S-protein into a fusion competent isoform, and one non-S-protein peptide representing the SARS-CoV-2 membrane protein (M1). FIG. 1 shows peptides selected in the S-protein 51 region. Only one of the three subunits is shown here for simplicity.

Table 3 shows peptide immunogens derived from the wild-type S-peptides of SARSCoV-2. Residues and protecting groups have been added to the respective S-peptides to protect them from proteolytic degradation and increase their serum half-life in vivo. Moreover, the C of S4 and S6 peptides have been replaced with S to avoid interference with coupling to the HhC.

TABLE 3

SARS-COV-2 Immunogen Peptides Tested as Vaccine Candidates

| Peptide | Sequence |
|---------|----------|
| S1 | Acetyl-VSFIEDLLFNKVTLADAG FDDEDC-NH$_2$ (SEQ ID NO: 73) |
| S2 | Acetyl-VSYQTQTNSPRRARSVAS QSIIDDEDC-NH$_2$ (SEQ ID NO: 57) |
| S3 | Acetyl-VFSQILPDPSKPSKRSFI EDDEDC-NH$_2$ (SEQ ID NO: 69) |
| S4 | Acetyl-VNGVEGFNSYFPLQSYGF QPTNG VGYQDDEDC-NH$_2$ (SEQ ID NO: 115) |
| S5 | Acetyl-VNYNYLYRLFRKSNLKPFER DISTEIYQAGSTPDDEDC-NH$_2$ (SEQ ID NO: 55) |
| S6 | Acetyl-VSVLYNSASFSTFKSYGV SPTKLN DLSFTNDDEDC-NH$_2$ (SEQ ID NO: 54) |
| M1 | Acetyl-VMADSNGTITVEELKKLLE QWNLVIDDEDC-NH$_2$ (SEQ ID NO: 67) |

The peptide immunogens in Table 3 are conjugated to a hC (scaffold) for immunizing mice. Table 4 shows mouse and human hC. The hC includes linkers/spacers and one or more residues such as V and D. The hC also includes T-cell epitopes and protecting groups at the N-terminus and C-terminus.

TABLE 4

Scaffold Peptide

| | |
|---|---|
| Mouse Scaffold | *Acetyl-VASNENMETMGPGPGDIRSIGKEIRSI GREIRSIGKEIRSIGREGPGPGFQDAY NAAGGHNAVF-NH2 (SEQ ID NO: 112) |

Solid-Phase Peptide Synthesis: The peptides of Tables 3 and 4 were synthesized by solid-phase peptide synthesis. The peptides were synthesized with an N-terminal acetyl protecting group and a C-terminal amide group to increase stability in the serum (in vivo). Synthesized peptides were subjected to HPLC-UV and MALDI to confirm purity and identity, respectively. Peptides were delivered as a lyophilized powder and stored at −20° C. until use. Prior to use (in conjugation or immunization experiments), peptides were dissolved in water and stored at −20° C.

Figure 2A:
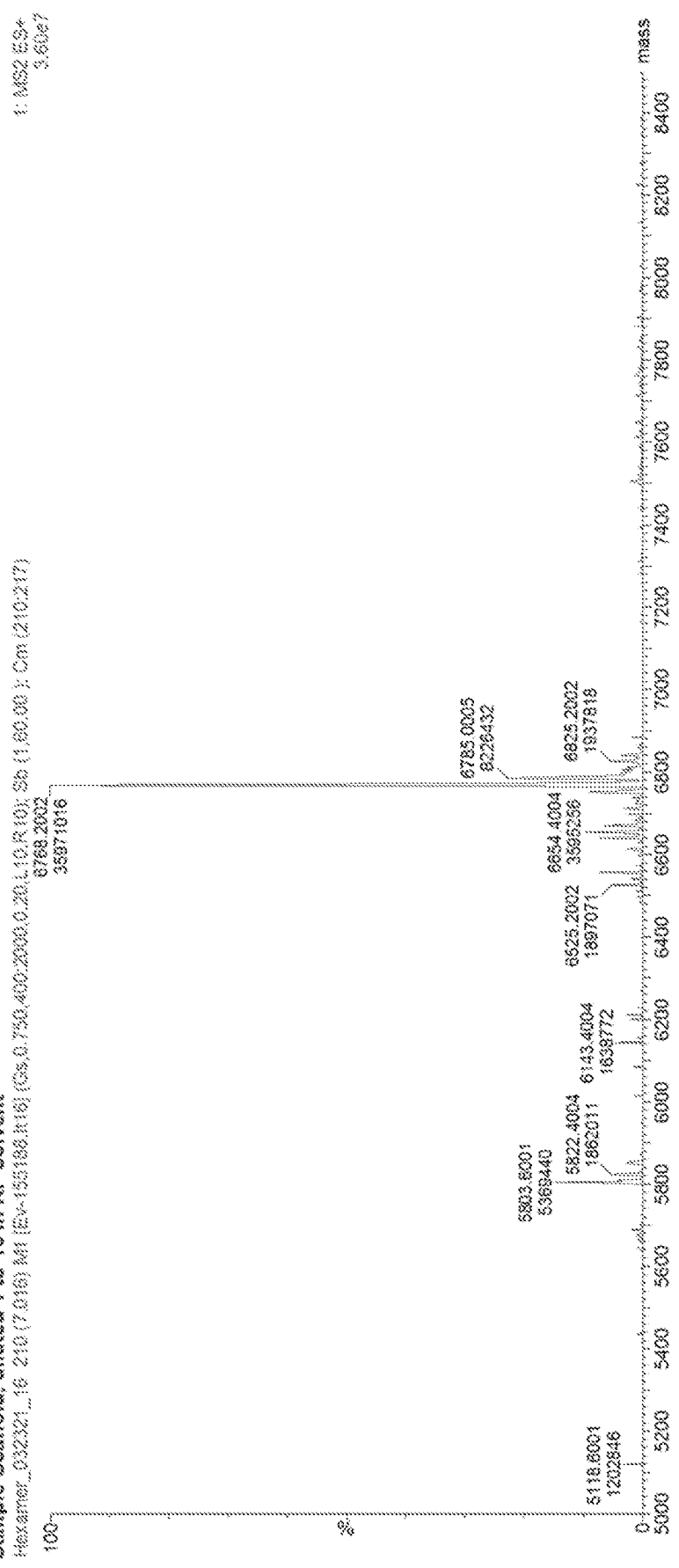
FIGS. 2A and 2B show positive ion ESI LC/MS/MS spectra of the unconjugated scaffold (2A; expected size 6,767 Da) and the scaffold+S5 peptide conjugate (HS5) (2B). The lack of an m/z=6,768 ion in 2B suggests highly efficient and near quantitative coupling of S5 to the scaffold.
Figure 2B:
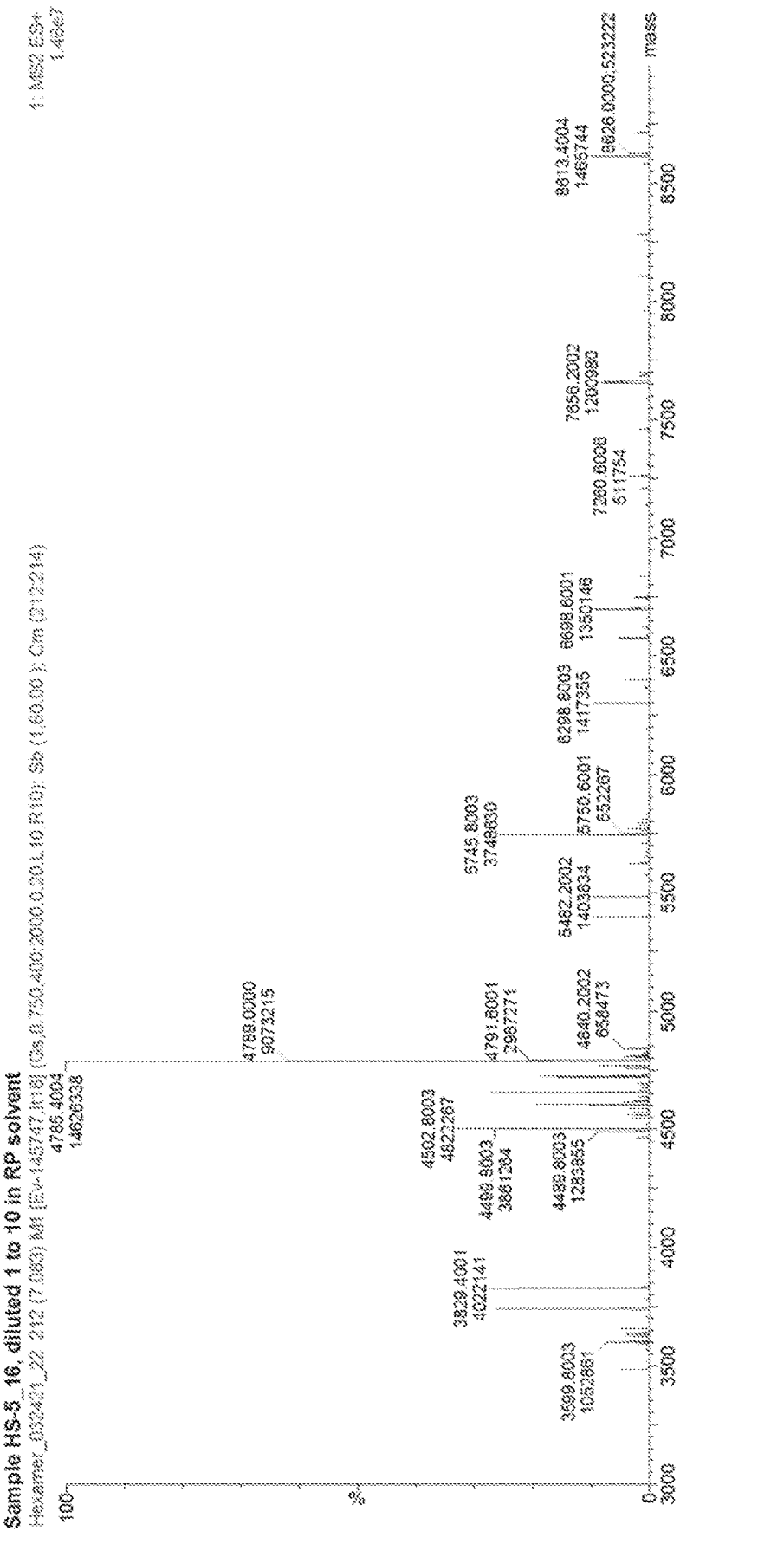
Figure 3A:
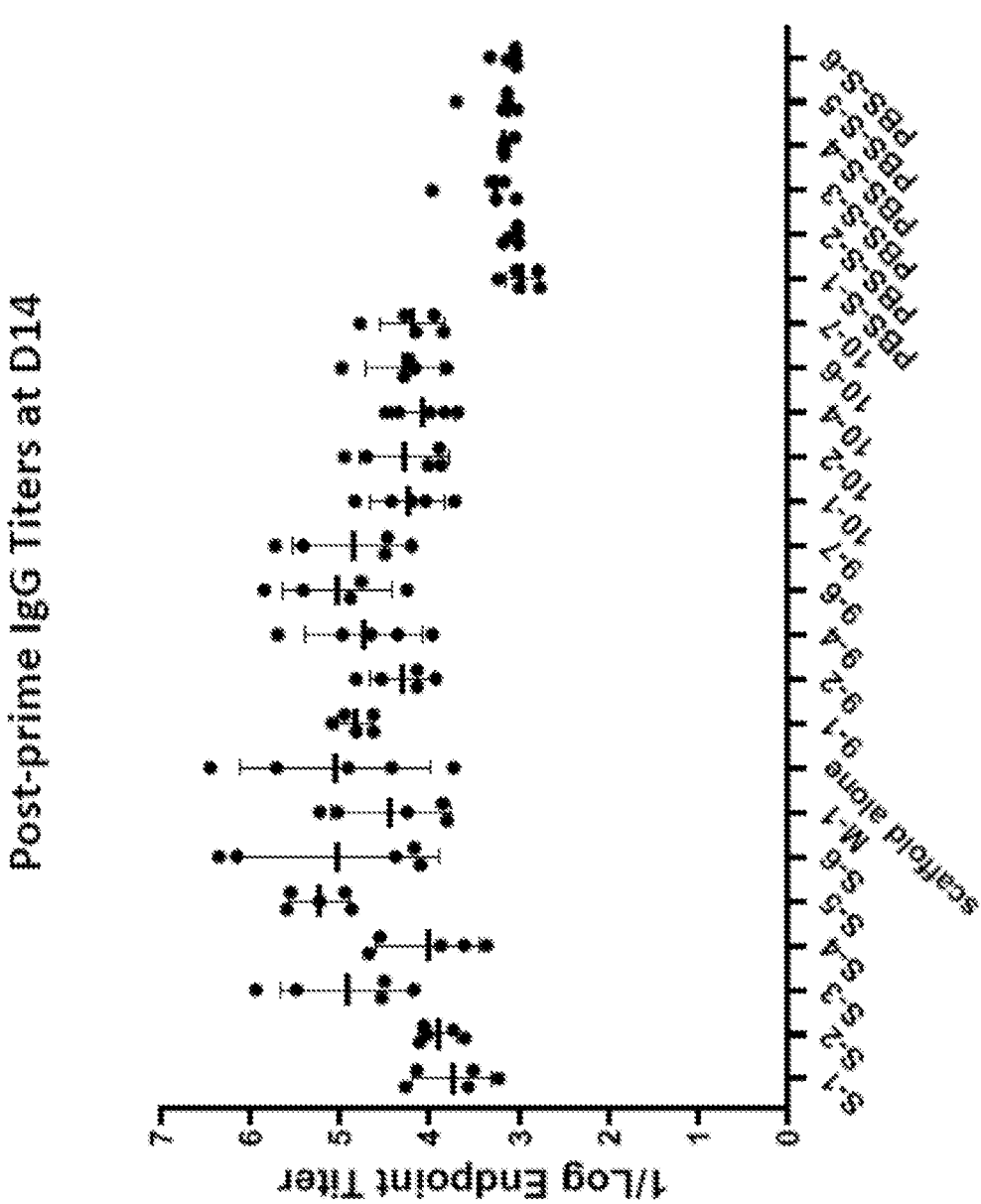
FIGS. 3A, 3B, 3C, 3D, and 3E show mouse IgG titers at d14 (day 14), d28, d42, d56, and d84, respectively, following immunizations according to Table 3. S1 (S-1), S2 (S-2), S3 (S-3), S4 (S-4), S5 (S-5), and S6 (S-6) are antigenic peptides from the S glycoprotein. S4, S5, and S6 peptides are in the receptor binding domain and the rest of the peptides include epitopes important for virus function, such as proteolytic cleavage sites (S2, S3), or sites proximal to proteolytic cleave sites (51). S6 is an epitope that is present in the sera of convalescent COVID-19 patients. M1 comprises an epitope on the SARS-CoV-2 membrane protein. These peptides were conjugated to the mouse scaffold (hC) prior to immunization of the mice. Group 9 includes mice that were immunized with equal □g quantities of the scaffold, 51, S2, S4, S6, and M1 peptides but the peptides were not covalently coupled to the scaffold. Group 9 was included to assess the requirements of covalent coupling of the antigenic peptide to the scaffold to produce an immune response. To measure immunogenicity, ELISA plates were coated separately with S1, S2, S4, S6, or M7 peptides so that binding specificity to each peptide could be measured. 9-1, 9-2, 9-4, and 9-6 and 9-7 refer to antibody titers in Group 9 measured by ELISA with S1 peptide (9-1), S2 peptide (9-2), S4 peptide (9-4), S6 peptide (9-6), and M1 peptide (9-7) as coating reagents. Groups 10-1 to 10-7 are identical to Group 9, but each peptide (S1, S2, S4, S6, and M1) was first conjugated to the mouse scaffold peptide to produce either HS1, HS2, HS4, HS6, or HM1. These were then mixed in equal □g quantities at the stated dose prior to immunization. The controls include the mouse scaffold alone and PBSS1, PBS-S2, PBS-S3, PBS-S4, PBS-S5, and PBS-S6, which is the PBS+adjuvant sera incubated with S1, S2, S3, S4, S5, and S6 peptides coated on the ELISA plate.
Figure 3B:
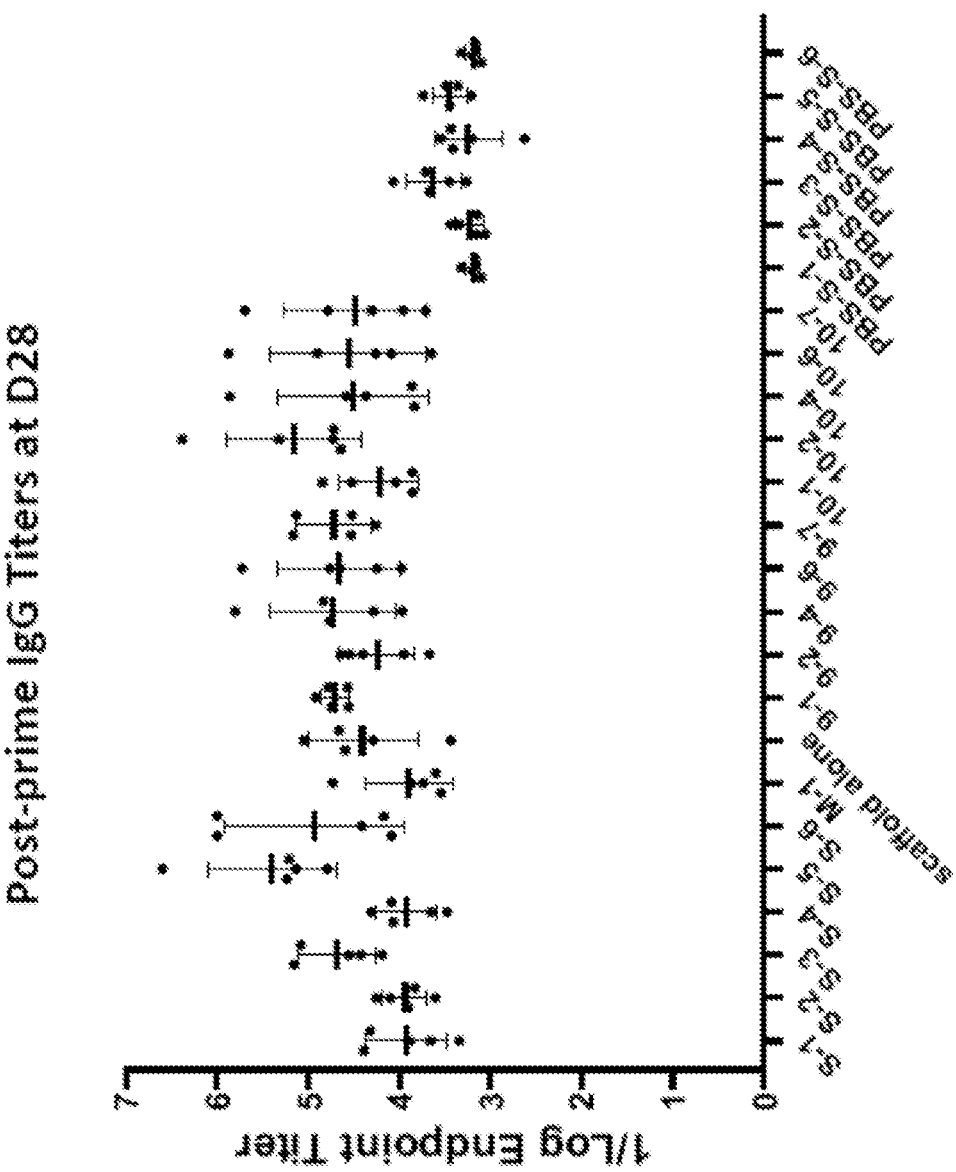
Figure 3C:
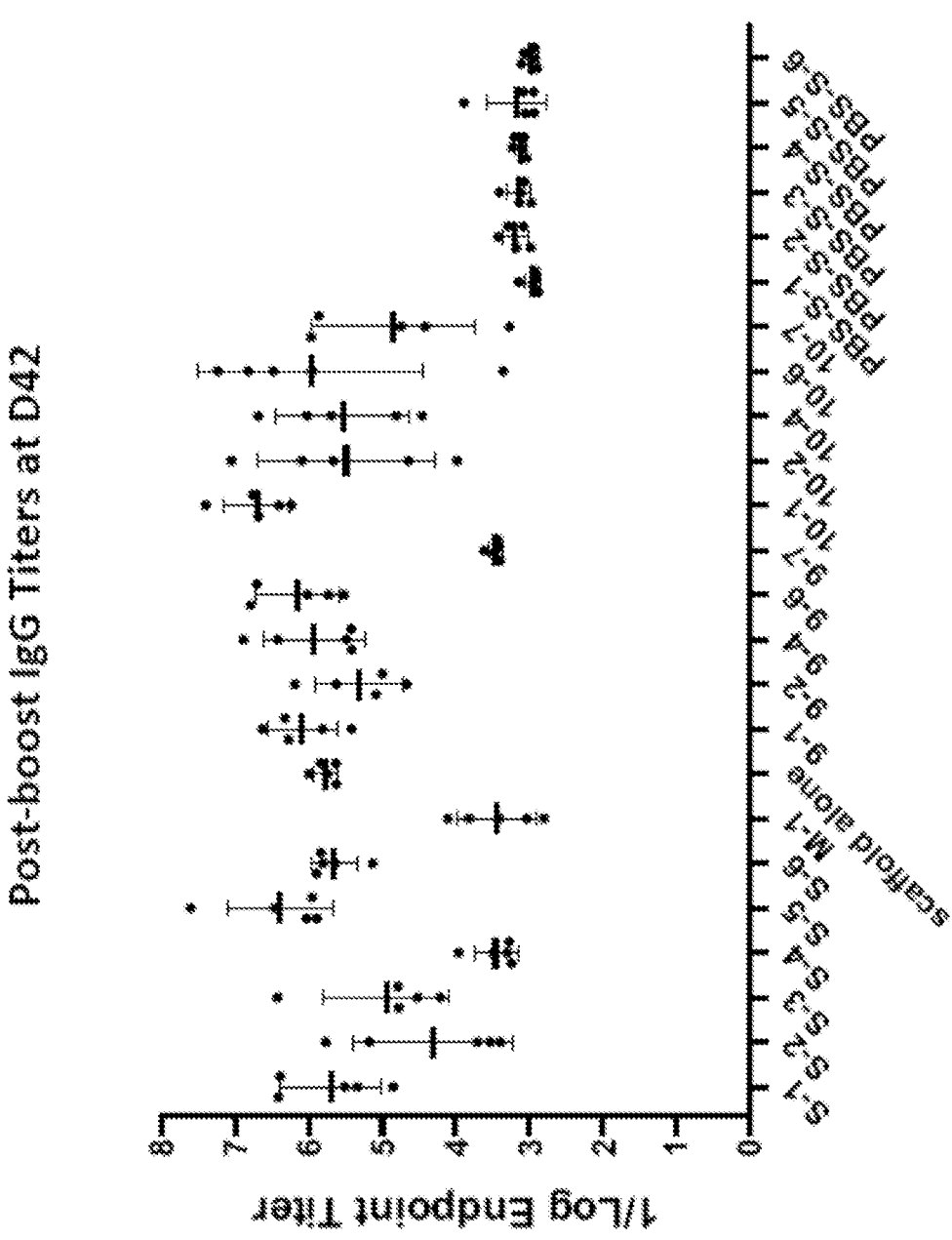
Figure 3D:
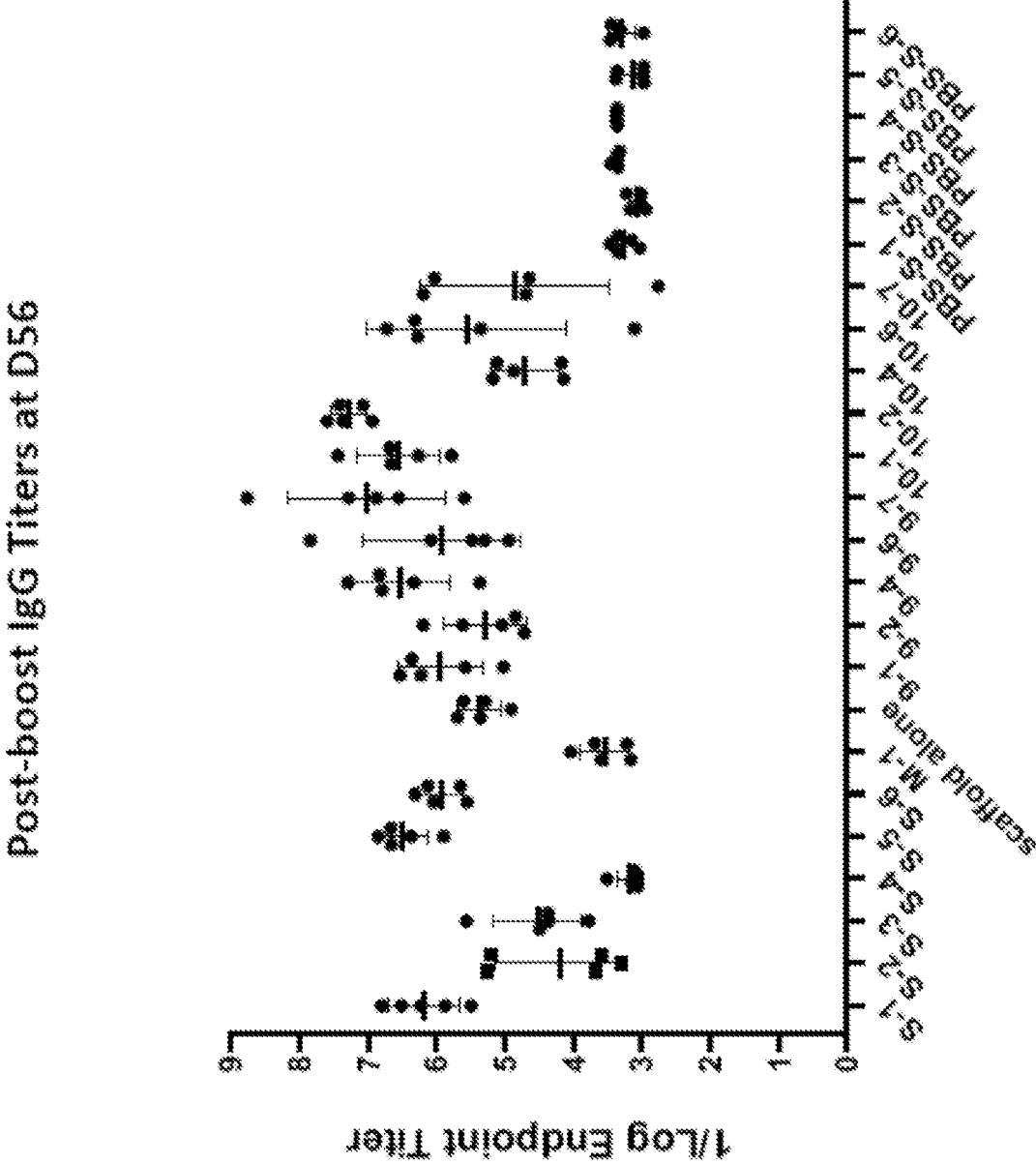
Figure 3E:
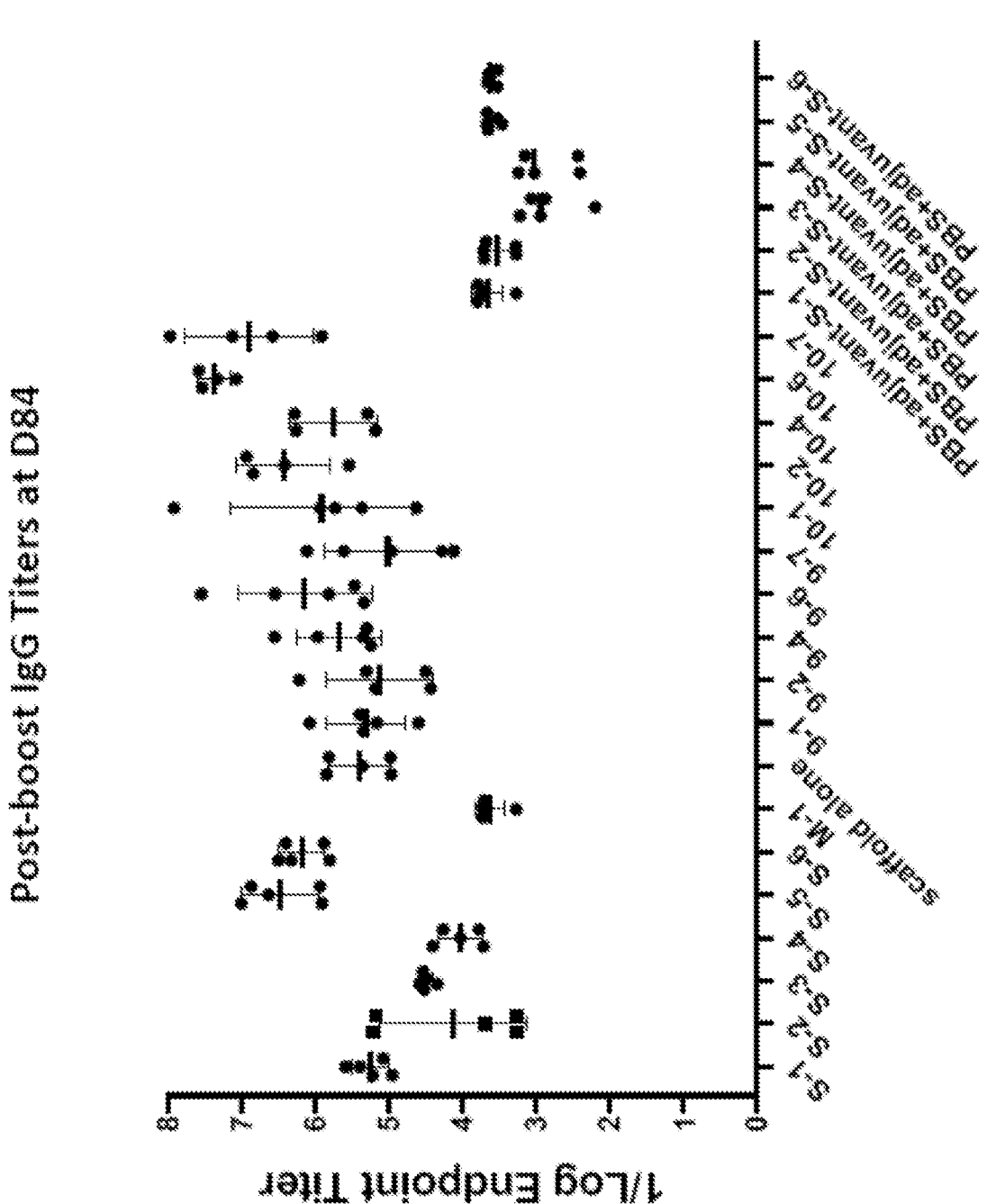
Figure 4A:
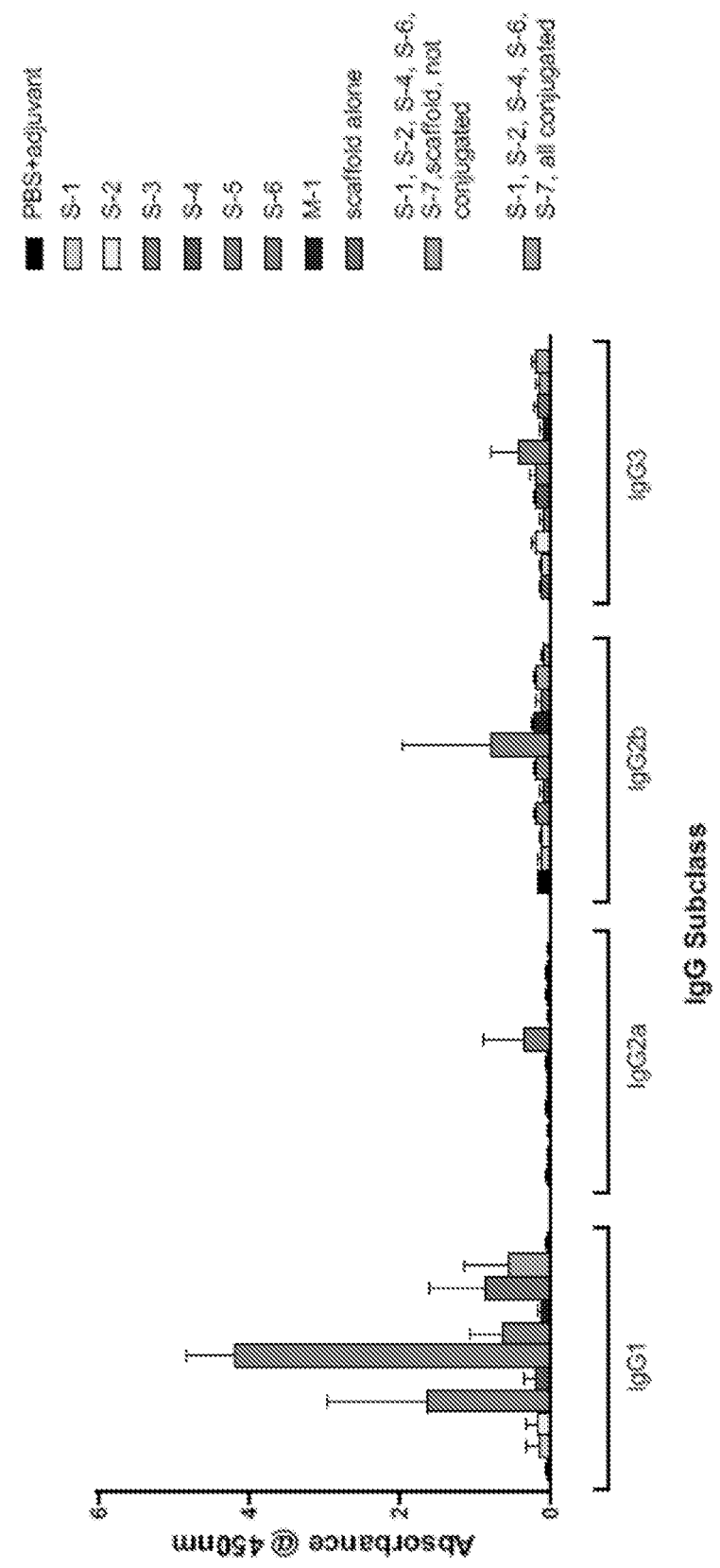
FIGS. 4A, 4B, 4C, and 4D show adjuvanted vaccines induced isotype switching on d14, d28, d42, and d84 and that the Th1/Th2 immune was balanced
Figure 4B:
Figure 4B:
Figure 4C:
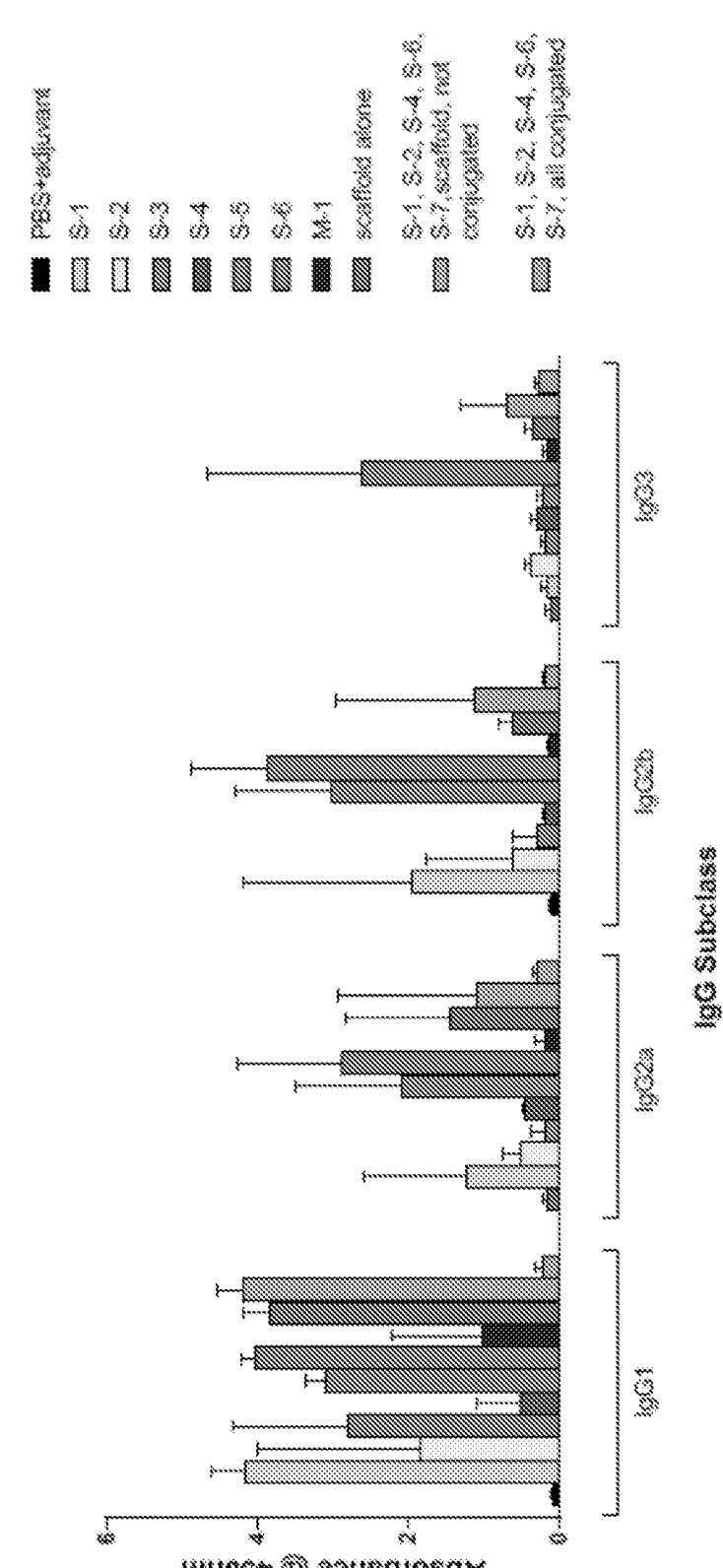
Figure 4D:
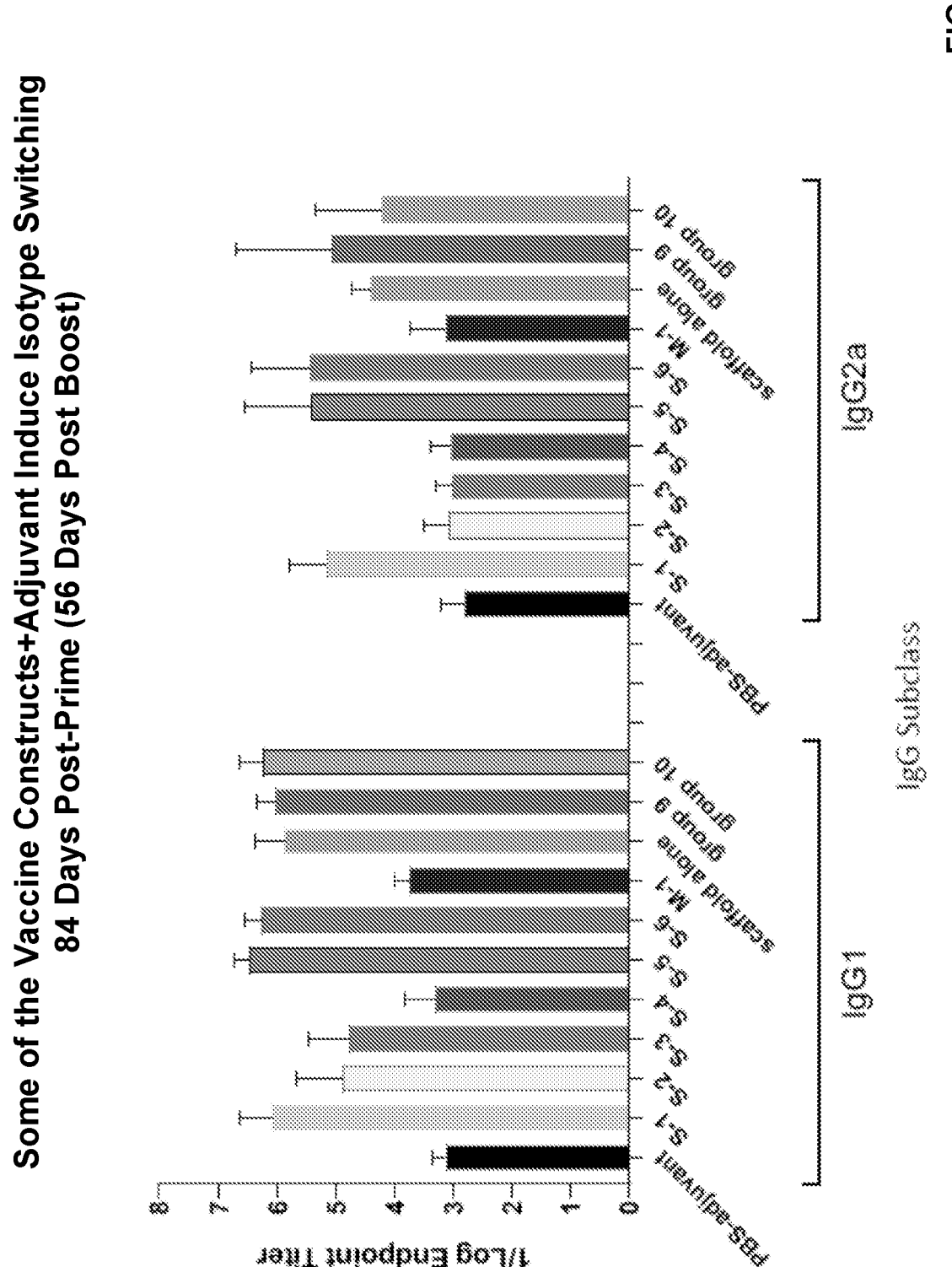

Covalent Coupling of Antigenic Peptides to the Scaffold Peptide: A heterobifunctional cross-linker was used to covalently couple the cysteinyl sulfhydryl groups of the antigenic peptides to the two lysine residues in the scaffold peptide. Each coupling reaction was performed separately. The scaffold peptide was incubated with 25 molar equivalents of sulfo-GMBS (N-γ-maleimidobutyryl-oxysulfosuccinimide ester) for 2 hours in the dark at room temperature in 50 mM potassium phosphate buffer, pH 6.0. The activated peptide was separated from excess (nonreacted) sulfo-GMBS by gel filtration through Sephadex G-10 resin equilibrated in 50 mM potassium phosphate buffer, pH 6.6. Antigenic peptides containing a C-terminal cysteine were incubated with 5 mM DTT for 30 min at room temperature in 50 potassium phosphate buffer, pH 6.6. DTT was separated from the peptides using gel filtration through Sephadex G-10 resin equilibrated in 50 mM potassium phosphate, pH 6.6. 2.5 molar equivalents of the reduced peptide were incubated with the sulfo-GMBS-activated scaffold for 16 hours at room temperature in the dark. Using these conditions, LC/MS/MS and SDS-PAGE experiments showed coupling of the peptides to the scaffold was nearly quantitative (i.e., the unconjugated scaffold was undetectable by LC/MS/MS; FIGS. 2A and 2B).

Mouse Immunizations: 60 male BALB/cJ mice (5 per group) were immunized (intramuscular) with 10 μg of adjuvanted scaffold-conjugated peptides (HS1 (51 peptide conjugated to hexamer (H) hC), HS2, HS3, HS4, HS5, HS6, and HM1) or two separate pooled mixtures: the first is a pooled mixture including the scaffold, 51, S2, S4, S6, and M1 peptides not conjugated to the scaffold, and mixed in equal μg quantities before immunization (Group 9). The second pool consists of mixing in equal μg quantities of HS1, HS2, HS4, HS6, and HM1 before immunization. The immunization schedule was a prime-boost-boost. Mice were immunized on d0 and boosted on d14 and d28. Blood was collected on d14, d28, d42, d56, and d84 for antibody titer determination and SARS-CoV-2 virus neutralization assays. Table 5 summarizes the immunization schedule.

TABLE 5

Immunization Schedule
Immunization Schedule: Prime-Boost Boost

| | | | Antigen | | Injections | |
| --- | --- | --- | --- | --- | --- | --- |
| Group | N | Name | Dose (mg) | Dose Conc. (mg/uL) | Volume (mL) | Route |
| 1 | 5 | HS1[1] | 10 | 0.1 | 2 × 50 | IM |
| 2 | 5 | HS2 | 10 | 0.1 | 2 × 50 | IM |
| 3 | 5 | HS3 | 10 | 0.1 | 2 × 50 | IM |
| 4 | 5 | HS4 | 10 | 0.1 | 2 × 50 | IM |
| 5 | 5 | HS5 | 10 | 0.1 | 2 × 50 | IM |
| 6 | 5 | HS6 | 10 | 0.1 | 2 × 50 | IM |
| 7 | 5 | HM1[2] | 10 | 0.1 | 2 × 50 | IM |
| 8 | 5 | Scaffold alone | 10 | 0.1 | 2 × 50 | IM |

TABLE 5-continued

Immunization Schedule
Immunization Schedule: Prime-Boost Boost

| | | | Antigen | | Injections | |
| --- | --- | --- | --- | --- | --- | --- |
| Group | N | Name | Dose (mg) | Dose Conc. (mg/uL) | Volume (mL) | Route |
| 9 | 5 | Scaffold, S1, S2, S4, S6, M1 not conjugated and pooled | 10 | 0.1 | 2 × 50 | IM |
| 10 | 5 | HS-1, 2, 4, 6, M1 conjugated and pooled | 10 | 0.1 | 2 × 50 | IM |
| 11 | 5 | PBS + adjuvant | N/A | N/A | 2 × 50 | IM |
| Total Mice | 60 | | | | | |

[1]HS1 is the S1 peptide covalently coupled to the Hexamer (H) hC. Likewise, HS2 is the S2 peptide coupled to the scaffold, and similarly for HS3 to HS6 and HM1

[2]HM1 is the M1 peptide coupled to the Hexamer (H) hC. M1 is an epitope belonging to the SARS-CoV-2 membrane glycoprotein and does not comprise any part of the S glycoprotein.

Antibody Titer Determinations: NUNC Maxisorp plates were coated with a capture reagent which included peptides in Table 3 covalently coupled to bovine serum albumin. 96-well plates were coated with 200 ng of BSA-conjugated peptides and incubated overnight at 4° C. in 50 mM potassium phosphate buffer, pH 7.4). Plates were washed twice with washing buffer (1× Tris-buffered Saline; 50 mM Tris-HCL, pH 8.0, 0.15M NaCl, 0.01% Tween20). Plates were blocked for 1 hour in blocking buffer (3% BSA+Tris-buffered Saline) and then washed as before.

An initial dilution of mouse serum was made (1:100 for d14 bleeds, 1:500 for all other bleeds) and 7 sequential 5-fold serial dilutions were made in 0.1 ml of blocking buffer. Diluted serum was transferred to the blocked ELISA plates and incubated for 1 hour with gentle shaking. Plates were washed four times with tris-buffered saline+0.01% Tween20 using an automated plate washer. Goat anti-mouse IgG-HRP was diluted 1:8,000 in blocking buffer and then added (0.1 ml per well) to the washed ELISA plates. After incubation for 1 hour with gentle shaking, the plates were washed as before followed by the addition of TMB substrate solution. Plates were developed for 30 min at room temp and then the reactions were quenched by adding 0.05 ml of 2M sulfuric acid. Absorbance at 450 nm was measured in all wells of the plate. Endpoint titer values were calculated as the dilution at which the ELISA signal in diluted serum was above the cutoff value. The cutoff value was calculated by diluting naïve mouse serum in the same way as the immunized sera were diluted and running these controls alongside the immunized sera. The mean absorbance of the naïve sera+(2*SD) was defined as the cutoff value.

Figures 5E, 5F, 5G, 5H:
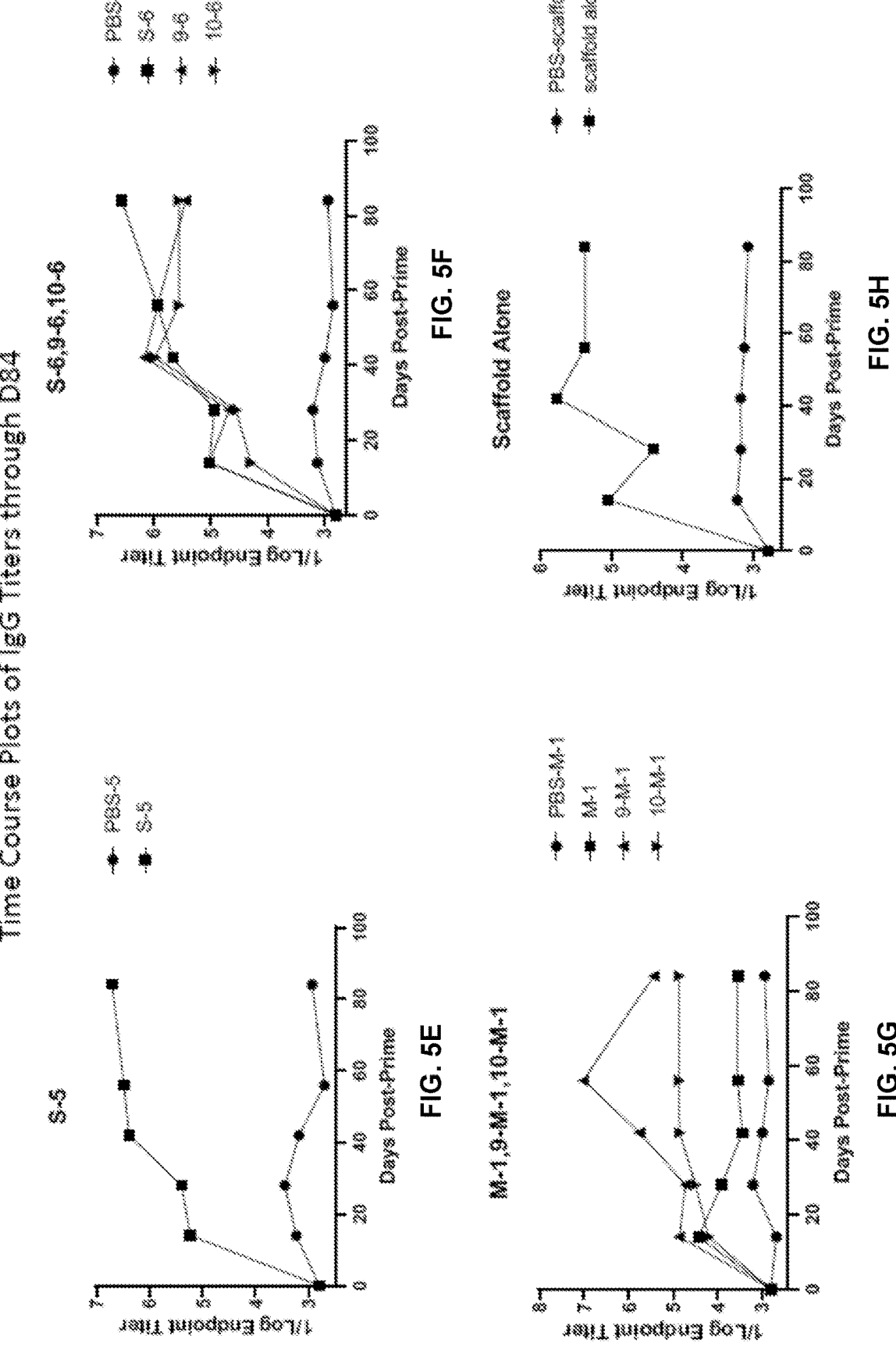
Figure 6:
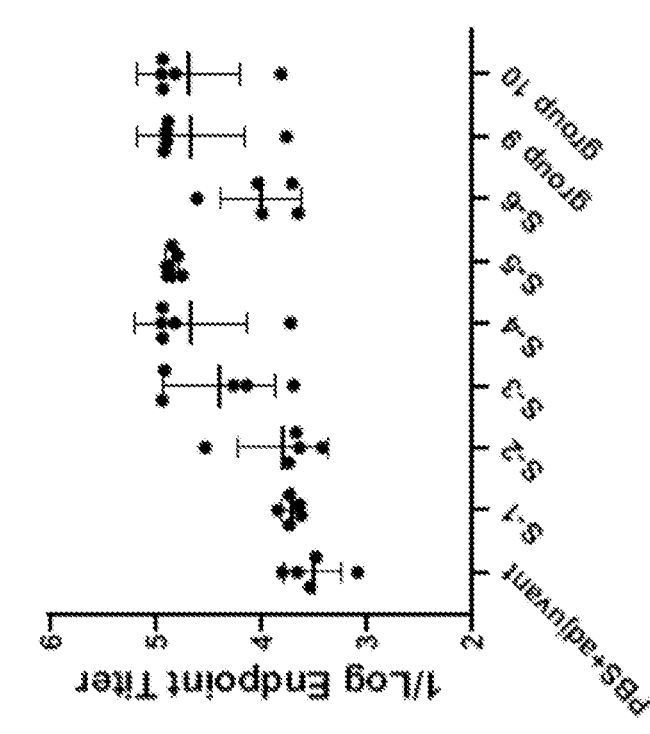
FIG. 6 shows d56 sera from mice immunized with HS1, HS2, HS3, HS4, HS5, HS6, or a pool of unconjugated (Group 9) or conjugated (Group 10) binding (to varying degrees) to the native S-glycoprotein produced in human cells. This shows that in addition to binding the antigenic peptides, antibodies in the sera are capable of binding to the native epitope in the S-protein.

The results are shown in FIGS. 3-5 indicate that the peptide immunogens conjugated to the hC (scaffold) have enhanced the IgG titers as compared to the controls.

Figure 7:
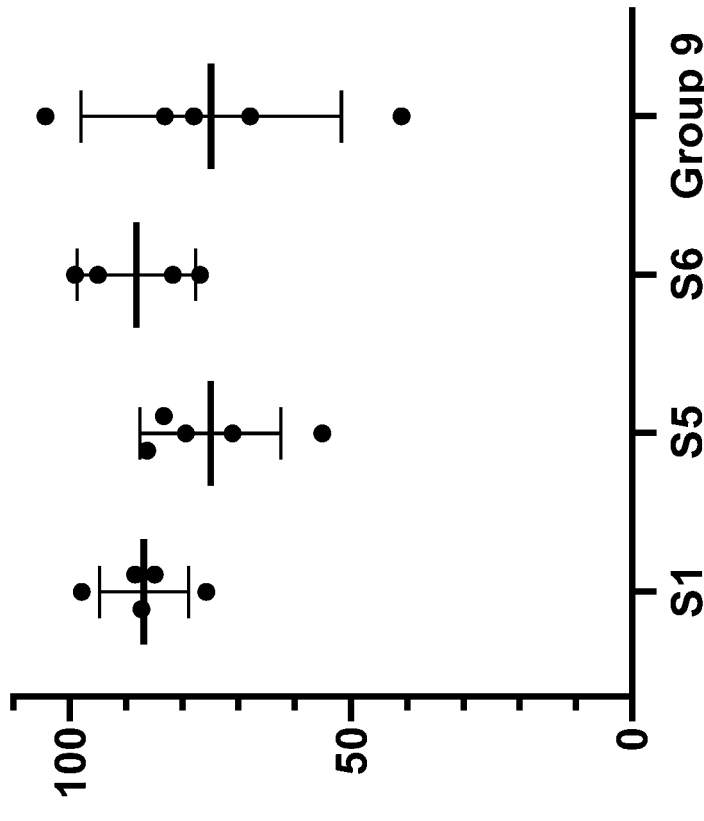
FIG. 7 shows inhibition of live SARS-CoV-2 virus entry into human cells by the vaccine (VP-HhC) at 1:400 serum dilution.

SARS-CoV-2 Virus Neutralization Assay: Sera from mice immunized with HS1, HS5, HS6, or pooled (HS1, HS2, HS4, HS6, and HM1) were diluted 1:400 in MEM media and incubated with $10^4$ SARS-CoV-2 virus particles for 30 min at room temperature. The virus+serum mix was then added to $10^4$ Vero-E6 human kidney cells (previously seeded into 96 well plates and grown overnight at 37° C.) and incubated for 48 hours at 37° C. Cells were fixed, permeabilized, and incubated with a fluorescent IgG specific to SARS-CoV-2 proteins. Viral infection was measured by reading fluorescence on a plate reader. Data were compared to 104 Vero-E6 cells incubated with 104 viral particles without any previous incubation with mouse sera and expressed as percent viral inhibition. FIG. 7 shows inhibition of live SARS-CoV-2 virus entry into human cells by VP-HhC at 1:400 serum dilution. VP of VP-HhC is 51, S5, or S6. Group 9 is a mix of 51, S2, S4, and S6 peptides and hC (mouse scaffold) without conjugation.

SARS-CoV-2 Plaque Assay: To measure the ability of the adjuvanted SARSCoV-2 peptide antigens to inhibit virus entry into human cells, replicating, and forming plaques (showing virus-induced cell lysis), sera from immunized mice in Groups 1, 5, and 6 (HS1, HS5, and HS6; Table 4) were mixed with $10^4$ live SARS-CoV-2 viral particles, incubated for 30 minutes, and then added to human Vero-E6 kidney cells grown in vitro (in triplicate). After 72 hours of incubation at 37° C., the number of plaques was quantified on each plate. Table 6 shows the number of plaques formed after incubation of sera from mice immunized with adjuvanted HS1, HS5, or HS6 vaccine and then added to human Vero-E6 kidney cells. The data shown in Table 6 are from triplicate repetitions.

TABLE 6

| Results of the Plaque Assay | | | | |
|---|---|---|---|---|
| | | Construct | | |
| Animal | PBS + adjuvant | HS1 | HS5 | HS6 |
| 19 Dec. 2020 | | | | |
| 1 | | 0 | 0 | 0 |
| 3 | | 0 | 0 | 0 |
| 5 | | 0 | 0 | 0 |
| 30 | | 0 | 0 | 0 |
| 50 | | 0 | 0 | 0 |
| 25 Feb. 2021 | | | | |
| 1 | 4 | 2 | | 16 |
| 3 | 10 | 0 | | 1 |
| 5 | 9 | 0 | | 3 |
| 30 | 5 | 0 | | 8 |
| 50 | 10 | 0 | | 5 |

In summary, antibodies generated in the vaccinated mouse studies were present in sera and these antibodies prevented live SARS-CoV-2 virus from entering human cells (as detected using fluorimetry) and prevented the live virus from forming plaques in human cells (a biological read-out). The results indicate that the peptide immunogens and scaffold peptides (hC), including the human scaffold peptide (Table 1), described herein are useful for treating and preventing diseases caused by viruses in subjects such as humans.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patents and patent applications cited in this specification are incorporated herein by reference in their entireties as if each individual publication, patent, or patent application were specifically and individually indicated to be incorporated by reference. While the foregoing has been described in terms of various embodiments, the skilled artisan will appreciate that various modifications, substitutions, omissions, and changes may be made without departing from the spirit thereof.

REFERENCES

Betakova, T., D. Svetlikova and M. Gocnik, 2013 Overview of measles and mumps vaccine: origin, present, and future of vaccine production. Acta Virol 57: 91-96.

Bill, R. M., 2015 Recombinant protein subunit vaccine synthesis in microbes: a role for yeast? J Pharm Pharmacol 67: 319-328.

Buckland, B. C., 2015 The development and manufacture of influenza vaccines. Hum Vaccin Immunother 11: 1357-1360.

Butler, M., and M. Spearman, 2014 The choice of mammalian cell host and possibilities for glycosylation engineering. Curr Opin Biotechnol 30: 107-112.

Chou, M. L., A. Bailey, T. Avory, J. Tanimoto and T. Burnouf, 2015 Removal of transmissible spongiform encephalopathy prion from large volumes of cell culture media supplemented with fetal bovine serum by using hollow fiber anion-exchange membrane chromatography. PLoS One 10: e0122300.

Ciabattini, A., E. Pettini, F. Fiorino, S. Lucchesi, G. Pastore et al., 2018 Heterologous Prime-Boost Combinations Highlight the Crucial Role of Adjuvant in Priming the Immune System. Front Immunol 9: 380.

Clark, T. G., and D. Cassidy-Hanley, 2005 Recombinant subunit vaccines: potentials and constraints. Dev Biol (Basel) 121: 153-163.

Corradin, G., N. Cespedes, A. Verdini, A. V. Kajava, M. Arevalo-Herrera et al., 2012 Malaria vaccine development using synthetic peptides as a technical platform. Adv Immunol 114: 107-149.

Corradin, G., A. V. Kajava and A. Verdini, 2010 Long synthetic peptides for the production of vaccines and drugs: a technological platform coming of age. Sci Transl Med 2: 50rv53.

Del Giudice, G., R. Rappuoli and A. M. Didierlaurent, 2018 Correlates of adjuvanticity: A review on adjuvants in licensed vaccines. Semin Immunol.

Evans, J. T., C. W. Cluff, D. A. Johnson, M. J. Lacy, D. H. Persing et al., 2003 Enhancement of antigen-specific immunity via the TLR4 ligands MPL adjuvant and Ribi.529. Expert Rev Vaccines 2: 219-229.

Fiorucci, S., and M. Zacharias, 2010 Prediction of protein-protein interaction sites using electrostatic desolvation profiles. Biophys J 98: 1921-1930.

Fiorucci, S., and M. Zacharias, 2014 Computational antigenic epitope prediction by calculating electrostatic desolvation penalties of protein surfaces. Methods Mol Biol 1184: 365-374.

Genzel, Y., 2015 Designing cell lines for viral vaccine production: Where do we stand? Biotechnol J 10: 728-740.

Grein, T. A., R. Michalsky and P. Czermak, 2014 Virus separation using membranes. Methods Mol Biol 1104: 459-491.

Haste Andersen, P., M. Nielsen and O. Lund, 2006 Prediction of residues in discontinuous B-cell epitopes using protein 3D structures. Protein Sci 15: 2558-2567.

Hermanson, G. T., 2013a Chapter 2—Functional Targets for Bioconjugation, pp. 127-228 in *Bioconjugate Techniques (Third Edition)*, edited by G. T. Hermanson. Academic Press, Boston.

Hermanson, G. T., 2013b Chapter 6—Heterobifunctional Crosslinkers, pp. 299-339 in *Bioconjugate Techniques (Third Edition)*, edited by G. T. Hermanson. Academic Press, Boston.

Hu, Y. C., 2005 Baculovirus as a highly efficient expression vector in insect and mammalian cells. Acta Pharmacol Sin 26: 405-416.

Hu, Y. C., K. Yao and T. Y. Wu, 2008 Baculovirus as an expression and/or delivery vehicle for vaccine antigens. Expert Rev Vaccines 7: 363-371.

Jespersen, M. C., B. Peters, M. Nielsen and P. Marcatili, 2017 BepiPred-2.0: improving sequence-based B-cell epitope prediction using conformational epitopes. Nucleic Acids Res 45: W24-W29.

Josefsberg, J. O., and B. Buckland, 2012 Vaccine process technology. Biotechnol Bioeng 109: 1443-1460.

Kawakami, K., and R. K. Puri, 2004 Regulatory expectations during product development for tumour vaccines. Dev Biol (Basel) 116: 53-59; discussion 69-76.

Khan, A., S. Datta, S. C. Das, T. Ramamurthy, J. Khanam et al., 2003 Shiga toxin producing *Escherichia coli* infection: current progress & future challenges. Indian J Med Res 118: 1-24.

Kim, H. J., and H. J. Kim, 2017 Yeast as an expression system for producing virus-like particles: what factors do we need to consider? Lett Appl Microbiol 64: 111-123.

Kost, T. A., and C. W. Kemp, 2016 Fundamentals of Baculovirus Expression and Applications. Adv Exp Med Biol 896: 187-197.

Legastelois, I., S. Buffin, I. Peubez, C. Mignon, R. Sodoyer et al., 2017 Non-conventional expression systems for the production of vaccine proteins and immunotherapeutic molecules. Hum Vaccin Immunother 13: 947-961.

Miller, K. D., R. Roque and C. H. Clegg, 2014 Novel Anti-Nicotine Vaccine Using a Trimeric Coiled-Coil Hapten Carrier. PLoS One 9: el 14366.

Nielsen, J., 2013 Production of biopharmaceutical proteins by yeast: advances through metabolic engineering. Bioengineered 4: 207-211.

Olugbile, S., C. Habel, C. Servis, F. Spertini, A. Verdini et al., 2010 Malaria vaccines—The long synthetic peptide approach: Technical and conceptual advancements. Curr Opin Mol Ther 12: 64-76.

Persing, D. H., R. N. Coler, M. J. Lacy, D. A. Johnson, J. R. Baldridge et al., 2002 Taking toll: lipid A mimetics as adjuvants and immunomodulators. Trends Microbiol 10: S32-37.

Pfaar, O., D. Cazan, L. Klimek, D. Larenas-Linnemann and M. A. Calderon, 2012 Adjuvants for immunotherapy. Curr Opin Allergy Clin Immunol 12: 648-657.

Ponomarenko, J., H. H. Bui, W. Li, N. Fusseder, P. E. Bourne et al., 2008 ElliPro: a new structure-based tool for the prediction of antibody epitopes. BMC Bioinformatics 9: 514.

Roohvand, F., M. Shokri, M. Abdollahpour-Alitappeh and P. Ehsani, 2017 Biomedical applications of yeast—a patent view, part one: yeasts as workhorses for the production of therapeutics and vaccines. Expert Opin Ther Pat 27: 929-951.

Rowland, S. S., R. L. Mayner and L. Barker, 2005 Advancing TB vaccines to Phase I clinical trials in the US: regulatory/manufacturing/licensing issues. Tuberculosis (Edinb) 85: 39-46.

Safdar, A., and M. M. Cox, 2007 Baculovirus-expressed influenza vaccine. A novel technology for safe and expeditious vaccine production for human use. Expert Opin Investig Drugs 16: 927-934.

Sari, D., K. Gupta, D. B. Thimiri Govinda Raj, A. Aubert, P. Drncova et al., 2016 The MultiBac Baculovirus/Insect Cell Expression Vector System for Producing Complex Protein Biologics. Adv Exp Med Biol 896: 199-215.

Seydoux, E., H. Liang, N. Dubois Cauwelaert, M. Archer, N. D. Rintala et al., 2018 Effective Combination Adjuvants Engage Both TLR and Inflammasome Pathways to Promote Potent Adaptive Immune Responses. J Immunol 201: 98-112.

Singh, M., and I. Srivastava, 2003 Advances in vaccine adjuvants for infectious diseases. Curr HIV Res 1: 309-320.

Smith, L. A., M. J. Jensen, V. A. Montgomery, D. R. Brown, S. A. Ahmed et al., 2004 Roads from vaccines to therapies. Mov Disord 19 Suppl 8: S48-52.

Tapia, F., I. Jordan, Y. Genzel and U. Reichl, 2017 Efficient and stable production of Modified Vaccinia Ankara virus in two-stage semi-continuous and in continuous stirred tank cultivation systems. PLoS One 12: e0182553.

Thomson, A. R., C. W. Wood, A. J. Burton, G. J. Bartlett, R. B. Sessions et al., 2014 Computational design of water-soluble alpha-helical barrels. Science 346: 485-488.

van Oers, M. M., 2006 Vaccines for viral and parasitic diseases produced with baculovirus vectors. Adv Virus Res 68: 193-253.

Vlak, J. M., and R. J. Keus, 1990 Baculovirus expression vector system for production of viral vaccines. Adv Biotechnol Processes 14: 91-128.

Warnock, J. N., and M. Al-Rubeai, 2006 Bioreactor systems for the production of biopharmaceuticals from animal cells. Biotechnol Appl Biochem 45: 1-12.

Wood, C. W., J. W. Heal, A. R. Thomson, G. J. Bartlett, A. A. Ibarra et al., 2017 ISAMBARD: an open-source computational environment for biomolecular analysis, modelling and design. Bioinformatics 33: 3043-3050.

Wood, C. W., and D. N. Woolfson, 2018 CCBuilder 2.0: Powerful and accessible coiled-coil modeling. Protein Sci 27: 103-111.

Wu, Y., and J. H. Collier, 2017 alpha-Helical coiled-coil peptide materials for biomedical applications. Wiley Interdiscip Rev Nanomed Nanobiotechnol 9.

Zaccai, N. R., B. Chi, A. R. Thomson, A. L. Boyle, G. J. Bartlett et al., 2011 A de novo peptide hexamer with a mutable channel. Nat Chem Biol 7: 935-941.

Geysen et al., *J. Immun. Meth.* 102:259-274 (1987)

Miranda et al., *Proc. Natl. Acad. Sci. USA* 96:1181-86 (1999)

Merrifield, *J. Am. Chem. Soc.* 85:2149-2154 (1963))

Altschul, S. F. et al., *J. Mol. Biol.* 215: 403-410 (1990)

Pearson and Lipman, *Proc. Natl. Acad. Sci. USA* 85; 2444-2448 (1988)

BLAST Manual, Altschul, S., et al., NCBI NLM NIH Bethesda, Md.)

The invention claimed is:

1. A viral peptide (VP) conjugate (VP-hC) or a VP oligomer (VPhC) comprising one or more viral peptides (VPs) covalently attached to a hapten carrier (hC), the hC comprising a monomeric peptide comprising SEQ ID NO: 19, 20, 21, 22, 23, 24, 25, 26, 27, 28, 29, 30, or 31.

2. The VP conjugate or VP oligomer of claim 1, wherein the monomeric peptide forms a dimer, trimer, tetramer, pentamer, hexamer, heptamer, octamer, nanomer, or decamer.

3. The VP conjugate or VP oligomer of claim 1, wherein the one or more VPs are obtained from a Coronavirus, an Influenza virus, a Respiratory Syncytial virus (RSV), Human Papillomavirus (HPV), Dengue virus, Yellow Fever virus (YFV), or West Nile virus (WNV) and optionally, wherein the one or more VPs are obtained from a SARS-COV-2 virus.

4. The VP conjugate or VP oligomer of claim 3, wherein the one or more VPs comprise one or more S peptides of the spike glycoprotein or the membrane protein (M) of a SARS-COV-2 virus, and optionally, wherein the one or more S peptides comprise S1, S2, S3, S4, S5, and/or S6, and the membrane peptide comprises M1.

5. The VP conjugate or VP oligomer of claim 4, wherein the one or more VPs comprise amino acid sequence SEQ ID NO: 136, 120, 132, 119, 118, 117, and/or 130.

6. The VP conjugate or VP oligomer of claim 1, wherein the one or more VPs comprise a modified VP, the modified VP comprising a modified amino acid sequence, and optionally, wherein one or more cysteines (C) are substituted with serine(S), or wherein the modified VP comprises amino acid sequence SEQ ID NO: 139 or 140.

7. The VP conjugate or VP oligomer of claim 5, wherein the one or more VPs comprise additional amino acids at its N- and/or C-terminus, the additional amino acids being V (valine) and/or DDEDC (SEQ ID NO: 116), and optionally, wherein the one or more VPs comprise amino acid sequence SEQ ID NO: 73, 57, 69, 115, 55, 54, and/or 67.

8. The VP conjugate or VP oligomer of claim 7, wherein the one or more VPs further comprise a protecting group at its N- and/or C-terminus, and optionally, wherein the protecting group comprises an acetyl group and/or an amide group.

9. The VP conjugate or VP oligomer of claim 1, wherein the VP conjugate or VP oligomer comprises two or more VPs from different sources or strains of SARS-COV-2.

10. The VP conjugate or VP oligomer of claim 1, wherein the one or more VPs are conjugated to the hC through lysine (K) on the monomeric peptide.

11. The VP conjugate or VP oligomer of claim 1, wherein the one or more VPs or the monomeric peptide further comprises one or more immunomodulators or additional haptens, one or more spacers or linkers between the hapten or immunomodulator and the monomeric peptide, and/or one or more residues for correct processing of the one or more T-cell epitopes.

12. The VP conjugate or VP oligomer of claim 11, wherein the one or more haptens or immunomodulators comprise one or more additional VPs, one or more T-cell epitopes, and/or one or more B-cell epitopes.

13. The VP conjugate or VP oligomer of claim 1, wherein the VP conjugate or VP oligomer comprises a hC comprising amino acid sequence SEQ ID NO: 112 or 113.

14. A pharmaceutical composition comprising the VP conjugate or VP oligomer of claim 1 and a pharmaceutically acceptable excipient, and optionally, wherein the excipient comprises MPL A.

15. A method of treating a subject having a viral disease or infection and/or preventing a subject from developing a viral disease or infection, wherein the method comprises administering to the subject, an effective amount of the composition of claim 14, wherein the VP induces an immune response in the subject, thereby treating the subject having the viral disease or infection or preventing the subject from developing the viral disease or infection, and optionally the viral disease or infection is caused by SARS-COV-2.

16. The method of claim 15, wherein the subject is a mammal, and optionally the mammal is a human.

17. A method of enhancing immunogenicity of a VP, wherein the method comprises:

(a) obtaining a monomeric peptide of the VP conjugate of claim 1, allowing the monomeric peptide to self-assemble into a hC, and conjugating a VP to the hC to obtain a VP-hC conjugate;

or (b) synthesizing a VP monomeric peptide (VPMP), wherein the VPMP comprises a monomeric peptide (MP) of the VP oligomer of claim 1 and a VP, and allowing the VPMP to self-assemble into a VPhC oligomer.

18. A method of preparing a VP therapeutic or vaccine, wherein the method comprises:

(a) obtaining a monomeric peptide of the VP conjugate or VP oligomer of claim 1, allowing the monomeric peptide to self-assemble into a hC, and conjugating a VP to the hC to obtain a VP-hC conjugate, thereby obtaining a VP therapeutic or vaccine;

or (b) synthesizing a VP monomeric peptide (VPMP), wherein the VPMP comprises a monomeric peptide of claim 1 and a VP of claim 1, and allowing the VPMP to self-assemble into a VPhC oligomer, thereby obtaining a VP therapeutic or vaccine.

19. The method of claim 17, wherein the method further comprises the monomeric peptide self-assembling into a hexameric hC.

20. A peptide immunogen comprising amino acid SEQ ID NO: 73, 57, 69, 115, 55, 54, or 67.

21. The peptide immunogen of claim 20, wherein the N-terminus and/or the C-terminus of the peptide immunogen comprise or comprises a protecting group, and optionally, wherein the protecting group of the N-terminus comprises an acetyl group and the protecting group of the C-terminus comprises an amide group.

22. A peptide scaffold comprising amino acid SEQ ID NO: 112 or 113.

23. The peptide scaffold of claim 22, wherein the N-terminus and/or the C-terminus of the peptide scaffold comprise or comprises a protecting group, and optionally, wherein the protecting group of the N-terminus comprises an acetyl group and the protecting group of the C-terminus comprises an amide group.

24. A composition comprising one or more peptide immunogens of claim 20 and a peptide scaffold comprising amino acid SEQ ID NO: 112 or 113.

25. The composition of claim 24, wherein the one or more peptide immunogens are attached to the peptide scaffold.

26. The composition of claim 24, wherein the one or more peptide immunogens are not attached to the peptide scaffold.

27. The method of claim 18, wherein the method further comprises the monomeric peptide self-assembling into a hexameric hC.

28. The peptide immunogen of claim 20, wherein the peptide immunogen comprises amino acid SEQ ID NO: 73, 55, or 54.

29. The VP-hC or a VPhC of claim 1, wherein the VP conjugate comprises one or more VPs conjugated to the hC; and wherein the VP oligomer comprises one or more VPs incorporated into the hC.

*    *    *    *    *